(12) United States Patent
Zhang et al.

(10) Patent No.: US 11,119,089 B2
(45) Date of Patent: Sep. 14, 2021

(54) NON-HYDROGEN-BONDING UNIVERSAL READER FOR DNA SEQUENCING

(71) Applicant: ARIZONA BOARD OF REGENTS ON BEHALF OF ARIZONA STATE UNIVERSITY, Scottsdale, AZ (US)

(72) Inventors: Peiming Zhang, Gilbert, AZ (US); Sovan Biswas, Tempe, AZ (US); Suman Sen, Tempe, AZ (US); Stuart Lindsay, Phoenix, AZ (US)

(73) Assignee: Arizona Board of Regents on behalf of Arizona, Scottsdale, AZ (US)

( * ) Notice: Subject to any disclaimer, the term of this patent is extended or adjusted under 35 U.S.C. 154(b) by 262 days.

(21) Appl. No.: 16/327,232

(22) PCT Filed: Aug. 21, 2017

(86) PCT No.: PCT/US2017/047818
§ 371 (c)(1),
(2) Date: Feb. 21, 2019

(87) PCT Pub. No.: WO2018/039129
PCT Pub. Date: Mar. 1, 2018

(65) Prior Publication Data
US 2019/0195856 A1    Jun. 27, 2019

Related U.S. Application Data

(60) Provisional application No. 62/378,033, filed on Aug. 22, 2016.

(51) Int. Cl.
*G01N 33/48* (2006.01)
*G01N 33/487* (2006.01)
(Continued)

(52) U.S. Cl.
CPC ..... *G01N 33/48721* (2013.01); *C07C 321/10* (2013.01); *C12Q 1/6869* (2013.01); *C07C 2603/50* (2017.05)

(58) Field of Classification Search
CPC ....... G01N 33/48721; G01N 33/48707; G01N 33/4833; G01N 33/483; G01N 33/48; C12Q 1/6869; C12Q 1/68
(Continued)

(56) References Cited

U.S. PATENT DOCUMENTS 8,628,649 B2   1/2014   Lindsay et al.
8,685,894 B2   4/2014   Chaput et al.
(Continued)

FOREIGN PATENT DOCUMENTS

WO   2006124089 A1   11/2006
WO   2007139849 A2   12/2007
(Continued)

OTHER PUBLICATIONS

Sen, S., "Identification of Biomolecular Building Blocks by Recognition Tunneling: Stride towards Nanopore Sequencing of Biomolecules", Arizona State University, Dissertation for the Degree Doctor of Philosophy, May 2016 [retrieved Jun. 26, 2019], 148 pages, retrieved from the internet: <https://pdfs.semanticscholar.org/4acd/466120a1d3e73579190f22c0d4c305975c.84.pdf?_ga=2.191749294.589475205.1561572351-864597407.1550179162>.
(Continued)

*Primary Examiner* — Christine T Mui
(74) *Attorney, Agent, or Firm* — Rodney J. Fuller; Booth Udall Fuller

(57) ABSTRACT

The present disclosure provides apparatus and methods for determining the sequence of a nucleic acid. The apparatus comprises electrodes that form a tunnel gap through which the nucleic acid can pass. The electrodes comprise a reagent
(Continued)

that is capable of selectively interacting with a nucleobase of the nucleic acid sequence. When the reagent interacts with a nucleobase, a detectable signal is produced and used to identify the nucleobase of the nucleic acid. Advantageously, the apparatus of this disclosure is specific to identifying nucleic acids.

13 Claims, 34 Drawing Sheets

(51) Int. Cl.
    *C12Q 1/6869*     (2018.01)
    *C07C 321/10*     (2006.01)
    *C12Q 1/68*     (2018.01)

(58) Field of Classification Search
    USPC .......................................... 436/86; 204/600
    See application file for complete search history.

(56) References Cited

U.S. PATENT DOCUMENTS

| | | | |
|---|---|---|---|
| 8,961,757 B2 | 2/2015 | Nuckolls et al. | |
| 8,968,540 B2* | 3/2015 | Reinhart | G01N 33/48721 204/452 |
| 9,140,682 B2 | 9/2015 | Lindsay et al. | |
| 9,395,352 B2 | 7/2016 | Lindsay et al. | |
| 9,593,372 B2 | 3/2017 | Lindsay et al. | |
| 9,701,784 B2* | 7/2017 | Rybtchinski | C08G 61/122 |
| 9,766,248 B2 | 9/2017 | Lindsay et al. | |
| 9,810,681 B2 | 11/2017 | Lindsay et al. | |
| 9,952,198 B2 | 4/2018 | Lindsay et al. | |
| 9,981,997 B2 | 5/2018 | Zhang et al. | |
| 10,139,417 B2 | 11/2018 | Lindsay et al. | |
| 10,145,846 B2 | 12/2018 | Lindsay et al. | |
| 10,267,785 B2 | 4/2019 | Lindsay et al. | |
| 10,287,257 B2 | 5/2019 | Zhang et al. | |
| 10,330,632 B2 | 6/2019 | Lindsay et al. | |
| 10,336,713 B2 | 7/2019 | Zhang et al. | |
| 10,379,102 B2 | 8/2019 | Lindsay et al. | |
| 10,422,787 B2 | 9/2019 | Lindsay et al. | |
| 10,442,771 B2 | 10/2019 | Lindsay et al. | |
| 10,444,220 B2 | 10/2019 | Lindsay et al. | |
| 2009/0018028 A1 | 1/2009 | Lindsay et al. | |
| 2011/0168562 A1 | 7/2011 | Nuckolls et al. | |
| 2012/0288948 A1* | 11/2012 | Lindsay | G01N 33/48721 436/94 |
| 2013/0302901 A1* | 11/2013 | Lindsay | G01N 33/48721 436/94 |
| 2014/0326604 A1* | 11/2014 | Han | G01N 33/48721 204/543 |
| 2015/0144506 A1 | 5/2015 | Lindsay et al. | |
| 2016/0108002 A1 | 4/2016 | Zhang et al. | |
| 2017/0343558 A1 | 11/2017 | Lindsay et al. | |
| 2019/0195884 A1 | 6/2019 | Lindsay et al. | |
| 2019/0242885 A1 | 8/2019 | Lindsay et al. | |
| 2019/0256616 A1 | 8/2019 | Zhang et al. | |
| 2019/0317040 A1 | 10/2019 | Lindsay et al. | |
| 2019/0353635 A1 | 11/2019 | Lindsay et al. | |
| 2020/0033320 A1 | 1/2020 | Lindsay et al. | |

FOREIGN PATENT DOCUMENTS

| | | |
|---|---|---|
| WO | 2008124706 A9 | 10/2008 |
| WO | 2009117517 A2 | 9/2009 |
| WO | 2009117522 A2 | 9/2009 |
| WO | 2010042514 A1 | 4/2010 |
| WO | 2011097171 A1 | 8/2011 |
| WO | 2013116509 A1 | 8/2013 |
| WO | 2013151756 A9 | 10/2013 |
| WO | 2013180819 A1 | 12/2013 |
| WO | 2014138253 A1 | 9/2014 |
| WO | 2014190299 A2 | 11/2014 |
| WO | 2014194246 A1 | 12/2014 |
| WO | 2015065985 A1 | 5/2015 |
| WO | 2015131073 A1 | 9/2015 |
| WO | 2015161119 A1 | 10/2015 |
| WO | 2015171930 A1 | 11/2015 |

OTHER PUBLICATIONS

Strauss, B., "The "A" rule revisited: polymerases as determinants of mutational specificity", DNA Repair, Feb. 2002 (available online Jan. 2002), vol. 1, No. 2, pp. 125-135 <DOI:10.1016/S1568-7864(01)00014-3>.
Swart, M. et al., "π-π stacking tackled with density functional theory", Journal of Molecular Modeling, Dec. 2007 (available online Sep. 2007), vol. 13, No. 12, pp. 1245-1257 <DOI:10.1007/s00894-007-0239-y>.
Szalay, T. et al., "De novo sequencing and variant calling with nanopores using PoreSeq", Nature Biotechnology, Oct. 2015 (available online Sep. 2015), vol. 33, No. 10, pp. 1087-1091 <DOI:10.1038/nbt.3360>.
The Cancer Genome Atlas Research Network., "Comprehensive genomic characterization of squamous cell lung cancers", Nature, Sep. 2012, vol. 489, pp. 519-525 <DOI:10.1038/nature11404>.
Treangen, T. et al., "Repetitive DNA and next-generation sequencing: computational challenges and solutions", Nature Reviews Genetics, Jan. 2012 (available online Nov. 2011), vol. 13, pp. 36-46 <DOI:10.1038/nrg3117>.
Tsutsui, M. et al., "Identifying single nucleotides by tunnelling current", Nature Nanotechnology, Apr. 2010 (available online Mar. 2010), vol. 5, No. 4, pp. 286-290 <DOI:10.1038/nnano.2010.42>.
Tuchband, M. et al., "Insulated gold scanning tunneling microscopy probes for recognition tunneling in an aqueous environment", Review of Scientific Instruments, Jan. 2012, vol. 83, article 015102, 5 pages <DOI:10.1063/1.3673640>.
Xu, B. et al., "Direct Conductance Measurement of Single DNA Molecules in Aqueous Solution", Nano Letters, May 2004, vol. 4, No. 6, pp. 1105-1108 <DOI:10.1021/nl0494295>.
Yakovchuck, P. et al., "Base-stacking and base-pairing contributions into thermal stability of the DNA double helix", Nucleic Acids Research, Jan. 2006, vol. 34, No. 2, pp. 564-574 <DOI:10.1093/nar/gkj454>.
Zhao, Y. et al., "Single-molecule spectroscopy of amino acids and peptides by recognition tunnelling", Nature Nanotechnology, Jun. 2014 (available online Apr. 2014), vol. 9, pp. 466-473 <DOI:10.1038/nnano.2014.54>.
Zwolak, M. et al., "Electronic Signature of DNA Nucleotides via Transverse Transport", Nano Letters, Feb. 2005 vol. 5, No. 3, pp. 421-424 <DOI:10.1021/nl048289w>.
Aradi, B. et al., "DFTB+, a Sparse Matrix-Based Implementation of the DFTB Method", The Journal of Physical Chemistry A, Jun. 2007, vol. 111, No. 26, pp. 5678-5684 <DOI:10.1021/jp070186p>.
Bang, F. et al., "Unraveling the complexity of the interactions of DNA nucleotides with gold by single molecule force spectroscopy", Nanoscale, Oct. 2015, vol. 7, No. 46, pp. 19528-19533 <DOI:10.1039/C5NR05695K>.
Chan, E., "Next-Generaion Sequencing Methods: Impact of Sequencing Accuracy on SNP discovery", In: Single Nucleotide Polymorphisms, Aug. 2009, pp. 95-111.
Chang, S. et al., "Chemical recognition and binding kinetics in a functionalized tunnel junction", Nanotechnology, May 2012, vol. 23, article 235101, 14 pages <DOI:10.1088/0957-4484/23/23/235101>.
Chang, S. et al., "Gap Distance and Interactions in a Molecular Tunnel Junction", Journal of the American Chemical Society, Aug. 2011, vol. 133, No. 36, pp. 14267-14269 <DOI:10.1021/ja2067737>.
Chang, S. et al., "Palladium electrodes for molecular tunnel junctions", Nanotechnology, Oct. 2012, vol. 23, No. 42, article 425202, 5 pages <DOI:10.1088/0957-4484/23/42/425202>.
Chaput, J. et al., "The Emerging World of Synthetic Genetics", Chemistry & Biology, Nov. 2012, vol. 19, No. 11, pp. 1360-1371 <DOI:10.1016/j.chembiol.2012.10.011>.

(56) References Cited

OTHER PUBLICATIONS

Datta, S. et al., "Electrical resistance: an atomistic view", Nanotechnology, May 2004, vol. 15, No. 7, pp. S433-S451 <DOI:10.1088/0957-4484/15/7/051>.
Di Carlo, A. et al., "Tight-binding DFT for molecular electronics (gDFTB) Introducing Molecular Electronics", Introducing Molecular Electronics (Springer), 2005, vol. 680, <DOI:10.1007/3-540-31514-4_6>.
Elstner, M. et al., "Self-consistent-charge density-functional tight-binding method for simulations of complex materials properties", Physical Review B, Sep. 1998, vol. 58, No. 11, pp. 7260-7268 <DOI:10.1103/PhysRevB.58.7260>.
Erdmann, M. et al., "Electrically induced bonding of DNA to gold", Nature Chemistry, Sep. 2010 (available online Jul. 2010), vol. 2, No. 9, pp. 745-749 <DOI:10.1038/nchem.722>.
Frampton, G. et al., "Development and validation of a clinical cancer genomic profiling test based on massively parallel DNA sequencing", Nature Biotechnology, Oct. 2013, vol. 31, No. 11, pp. 1023-1031 <DOI:10.1038/nbt.2696>.
GitHub., "SVM_DNA_TunnelVision" [online], GitHub, retrieved from the internet: <URL:https://github.com/ochensati/SVM_DNA_TunnelVision>, Jul. 29, 2015, 1 page.
Goodwin, S. et al., "Coming of age: ten years of next-generation sequencing technologies", Nature Review Genetics, Jun. 2016 (available online May 2016), vol. 17, pp. 333-351 <DOI:10.1038/nrg.2016.49>.
Grimme, S., "Do Special Noncovalent π-π Stacking Interactions Really Exist?", Angewandte Chemie, Apr. 2008 (available online Mar. 2008), vol. 47, No. 18, pp. 3430-3434 <DOI:10.1002/anie.200705157>.
Guckian, K. et al., "Factors Contributing to Aromatic Stacking in Water: Evaluation in the Context of DNA", Journal of the American Chemical Society, Feb. 2000, vol. 122, No. 10, pp. 2213-2222 <DOI:10.1021/ja9934854>.
Huang, H. et al., "Fidelity and Predominant Mutations Produced by Deep Vent Wild-Type and Exonuclease-Deficient DNA Polymerases During In Vitro DNA Amplification", DNA and Cell Biology, Jul. 1996 (available online Mar. 2009), vol. 15, No. 7, pp. 589-594 <DOI:10.1089/dna.1996.15.589>.
Huang, S. et al., "Identifying single bases in a DNA oligomer with electron tunnelling", Nature Nanotechnology, Dec. 2010 (available online Nov. 2010), vol. 5, pp. 868-873 <DOI:10.1038/nnano.2010.213>.
Im, J. et al., "Electronic single-molecule identification of carbohydrate isomers by recognition tunnelling", Nature Communications, Dec. 2016, vol. 7, article 13868, 7 pages <DOI:10.1038/ncomms13868>.
Jain, M. et al., "Improved data analysis for the MinION nanopore sequencer", Nature Methods, Apr. 2015 (available online Feb. 2015), vol. 12, No. 4, pp. 351-356 <DOI:10.1038/nmeth.3290>.
Jethava, V., "SVM-THETA Dense subgraph finding using SVM's" [online], GitHub, 2012, retrieved from the Internet: <URL:https://github.com/vjethava/svm-theta>.
Jünemann, S. et al., "Updating benchtop sequencing performance comparison", Nature Biotechnology, Apr. 2013, vol. 31, No. 4, pp. 294-296 <DOI:10.1038/nbt.2522>.
Kelley, S. et al., "Electron Transfer Between Bases in Double Helical DNA", Science, Jan. 1999, vol. 283, No. 5400, pp. 375-381 <DOI:10.1126/science.283.5400.375>.
Kimura-Suda, H. et al., "Base-Dependent Competitive Adsorption of Single-Stranded DNA on Gold", Journal of the American Chemical Society, Jul. 2003, vol. 125, No. 30, pp. 9014-9015 <DOI:10.1021/ja035756n>.
Lai, J. et al., "Fluorinated DNA Bases as Probes of Electrostatic Effects in DNA Base Stacking", Angewandte Chemie, Dec. 2003, vol. 42, No. 48, pp. 5973-5977 <DOI:10.1002/anie.200352531>.
Laszlo, A. et al., "Decoding long nanopore sequencing reads of natural DNA", Nature Biotechnology, Jun. 2014 (available online Aug. 2014), vol. 32, No. 8, pp. 829-833 <DOI:10.1038/nbt.2950>.
Laver, T. et al., "Assessing the performance of the Oxford Nanopore Technologies MinION", Biomolecular Detection and Quantification, Mar. 2015, vol. 3, pp. 1-8 <DOI:10.1016/j.bdq.2015.02.001>.
Li, Z. et al., "Synthesis of new derivatives of 8-oxoG-Clamp for better understanding the recognition mode and improvement of selective affinity", Bioorganic & Medicinal Chemistry, Jun. 2010 (available online Apr. 2010), vol. 18, No. 11, pp. 3992-3998 <DOI:10.1016/j.bmc.2010.04.025>.
Liang, F. et al., "Synthesis, Physicochemical Properties, and Hydrogen Bonding of 4(5)-Substituted 1-H-Imidazole-2-carboxamide, a Potential Universal Reader for DNA Sequencing by Recognition Tunneling", Chemistry A European Journal, May 2012, vol. 18, No. 19, pp. 5998-6007 <DOI:10.1002/chem.201103306>.
Lindsay, S., "The promises and challenges of solid-state sequencing", Nature Nanotechnology, Feb. 2016, vol. 11, No. 2, pp. 109-111 <DOI:10.1038/nnano.2016.9>.
Liu, L. et al., "Comparison of Next-Generation Sequencing Systems", Journal of Biomedicine and Biotechnology, Apr. 2012, vol. 2012, article 251364, 11 pages <DOI:10.1155/2012/251364>.
Madoui, M-A. et al., "Genome assembly using Nanopore-guided long and error-free DNA reads", BMC Genomics, Apr. 2015, vol. 16, No. 327, 11 pages <DOI:10.1186/s12864-015-1519-z>.
Manrao, E. et al., "Reading DNA at single-nucleotide resolution with a mutant MspA nanopore and phi29 DNA polymerase", Nature Biotechnology, Mar. 2012, vol. 30, No. 4, pp. 349-353 <DOI:10.1038/nbt.2171>.
Marincorena, I. et al., "Somatic mutation in cancer and normal cells", Science, Sep. 2015, vol. 349, No. 6255, pp. 1483-1489 <DOI:10.1126/science.aab4082>.
Mukhopadhyay, R., "DNA sequencers: the next generation", Analytical Chemistry, Mar. 2009 (available online Feb. 2009), vol. 81, No. 5, pp. 1736-1740 <DOI:10.1021/ac802712u>.
Ohshiro, T. et al., "Singlemolecule electrical random resequencing of DNA and RNA", Scientific Reports, Jul. 2012, vol. 2, No. 501, 7 pages <DOI:10.1038/srep00501>.
Paez, J. et al., "Genome coverage and sequence fidelity of phi29 polymerase-based multiple strand displacement whole genome amplification", Nucleic Acids Research, May 2004, vol. 32, No. 9, article e71, 11 pages <DOI:10.1093/nar/gnh069>.
Pang, P. et al., "Fixed-Gap Tunnel Junction for Reading DNA Nucleotides", ACS Nano, Nov. 2014, vol. 8, No. 12, pp. 11994-12003 <DOI:10.1021/nn505356g>.
Patent Cooperation Treaty, International Searching Authority, International Preliminary Report on Patentability for PCT/US2017/047818, 9 pages, dated Feb. 26, 2019, opinion mailed Jan. 18, 2018.
Patent Cooperation Treaty, International Searching Authority, International Search Report for PCT/US2017/047818, 3 pages, dated Jan. 18, 2018.
Patra, A. et al., "Structural and kinetic analysis of nucleoside triphosphate incorporation opposite an abasic site by human translesion DNA polymerase eta", The Journal of Biological Chemistry, Mar. 2015 (available online Feb. 2015), vol. 290, No. 13, pp. 8028-8038 <DOI:10.1074/jbc.M115.637561>.
Pecchia, A. et al., "Atomistic theory of transport in organic and inorganic nanostructures", Reports on Progress in Physics, Jul. 2004, vol. 67, No. 8, pp. 1497-1561 <DOI:10.1088/0034-4885/67/8/R04>.
Pecchia, A. et al., "Non-equilibrium Green's functions in density functional tight binding: method and applications", New Journal of Physics, Jun. 2008, vol. 10, article 065022, 17 pages <DOI:10.1088/1367-2630/10/6/065022>.
Petersheim, M. et al., "Base-stacking and base-pairing contributions to helix stability: thermodynamics of double-helix formation with CCGG, CCGGp, CCGGAp, ACCGGp, CCGGUp, and ACCGGUp", Biochemistry, Jan. 1983 (available online May 2002), vol. 22, No. 2, pp. 256-263 <DOI:10.1021/bi00271a004>.
Porezag, D. et al., "Construction of tight-binding-like potentials on the basis of density-functional theory: Application to carbon", Physical Review B, May 1995, vol. 51, No. 19, pp. 12947-12957 <DOI:10.1103/PhysRevB.51.12947>.

(56) References Cited

OTHER PUBLICATIONS

Qi, Y. et al., "Reproducibility of Variant Calls in Replicate Next Generation Sequencing Experiments", PLoS One, Jul. 2015, vol. 10, No. 7, article e119230, 16 pages <DOI:10.1371/journal.pone.0119230>.

Riley, K. et al., "On the Importance and Origin of Aromatic Interactions in Chemistry and Biodisciplines", Accounts of Chemical Research, 2013 (available online Aug. 2012), vol. 46, No. 4, pp. 927-936 <DOI:10.1021/ar300083h>.

Robasky, K. et al., "The role of replicates for error mitigation in next-generation sequencing", Nature Reviews Genetics, Jan. 2014 (available online Dec. 2013), vol. 15, No. 1, pp. 56-62 <DOI:10.1038/nrg3655>.

Ross, J. et al., "Comprehensive genomic profiling of 295 cases of clinically advanced urothelial carcinoma of the urinary bladder reveals a high frequency of clinically relevant genomic alterations", Cancer, Mar. 2016 (available online Dec. 2015), vol. 122, No. 5, pp. 702-711 <DOI:10.1002/cncr.29826>.

Ross, J. et al., "Comprehensive Genomic Profiling of Carcinoma of Unknown Primary Site: New Routes to Targeted Therapies", JAMA Oncology, Apr. 2015 (available online Feb. 2015), vol. 1, No. 1, pp. 40-49 <DOI:10.1001/jamaoncol.2014.216>.

Lindsay, Stuart et al., U.S. Appl. No. 16/597,837, filed Oct. 9, 2019.

\* cited by examiner

FIG. 11A
FIG. 11B
FIG. 11C
Iz
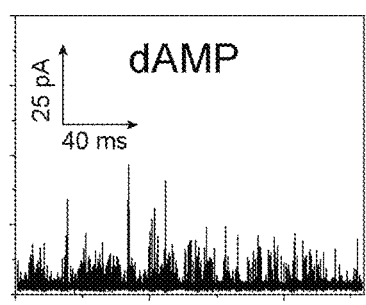
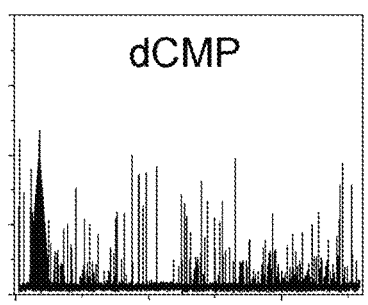
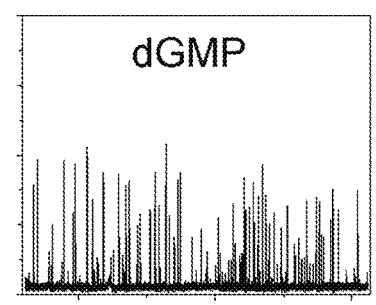
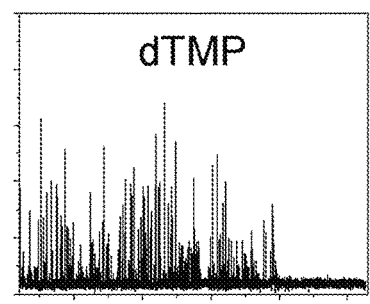
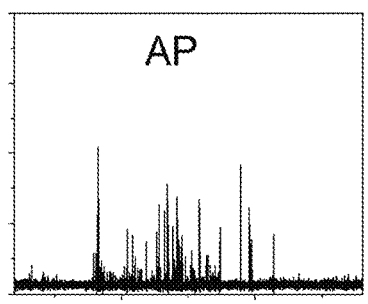
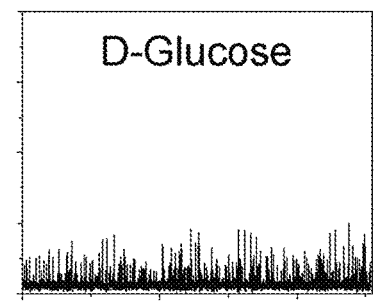
FIG. 11D
FIG. 11E
FIG. 11F FIG. 11G
FIG. 11H
FIG. 11I
Py
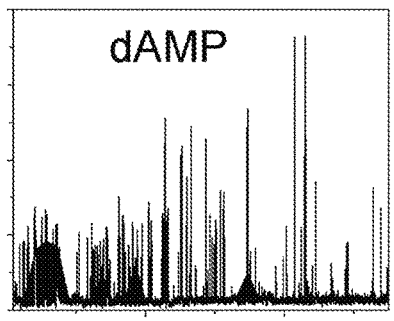
dAMP
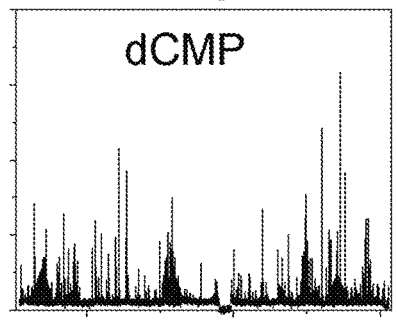
dCMP
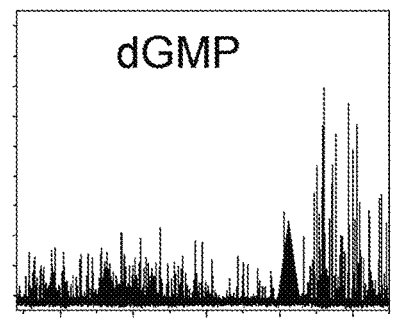
dGMP
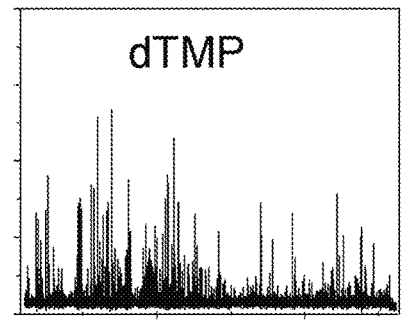
dTMP
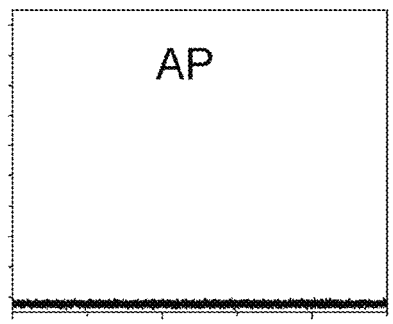
AP
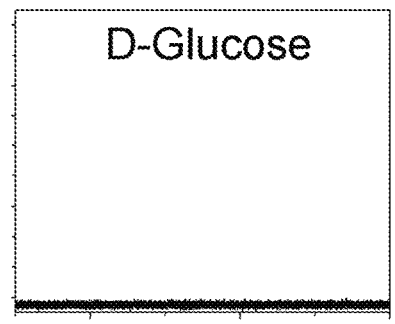
D-Glucose
FIG. 11J
FIG. 11K
FIG. 11L

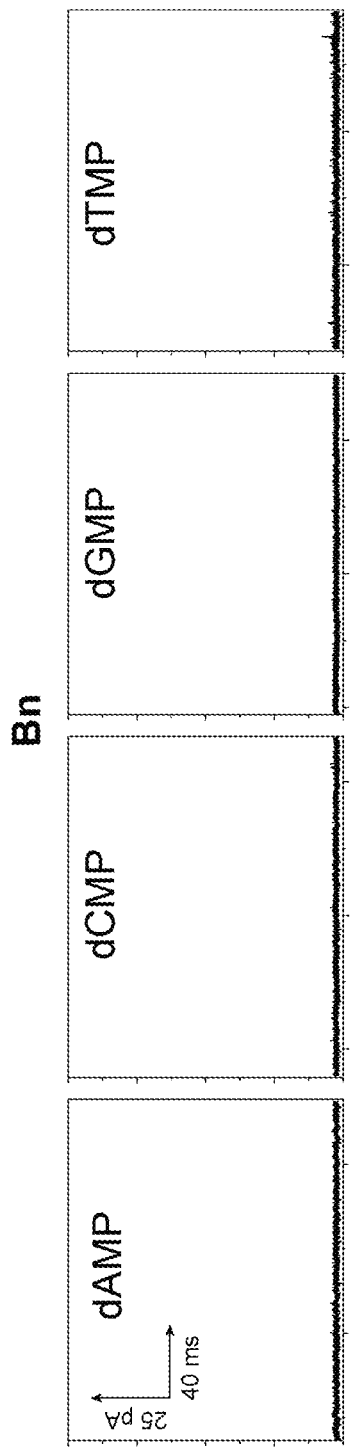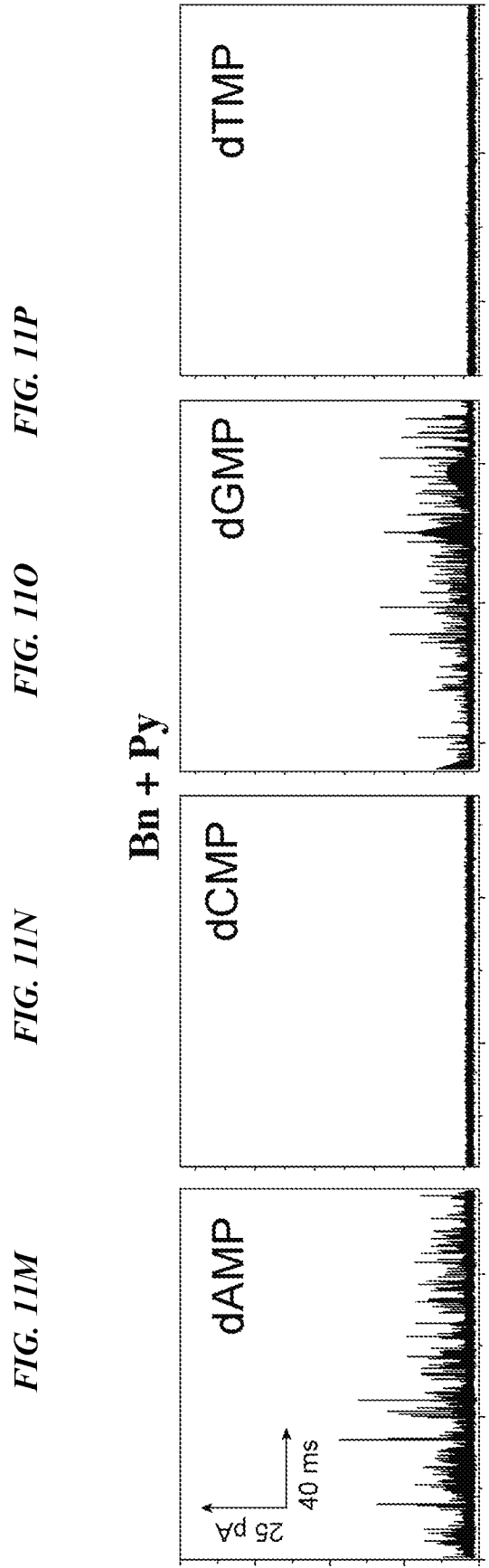

NON-HYDROGEN-BONDING UNIVERSAL READER FOR DNA SEQUENCING

CROSS REFERENCE TO RELATED APPLICATION

This application is a U.S. National Stage Application under 35 USC 371 of International Application PCT/US2017/047818, filed Aug. 21, 2017, which claims the priority benefit of the earlier filing date of U.S. Provisional Application No. 62/378,033 filed Aug. 22, 2016, which is hereby incorporated by reference in its entirety.

FEDERALLY SPONSORED RESEARCH OR DEVELOPMENT

This invention was made with government support under R01 HG006323 awarded by the National Institutes for Health. The government has certain rights in the invention.

BACKGROUND

DNA sequencing, particularly Next Generation Sequencing (NGS),[1] is the most powerful technology in genomic analysis at the present. NGS can sequence an individual human genome in a few days at a cost of ~$1000. Compared to conventional Sanger sequencing, however, NGS has lower read accuracy and shorter read length.[2] A recent study has warned that the reproducibility of single nucleotide variants (SNVs) calls was only around 80% even using the highest stringency of QC metrics with SOLiD sequencing, a NGS technology that has sequencing accuracy higher than others.[3] NGS also faces another great challenge of determining long repetitive regions in a genome. Although single molecule real time (SMRT) sequencing provides a long-read solution for the issue (see the world wide web (www) at pacb.com), it produces sequences at a much higher error rate per base than NGS does. Currently, DNA sequencing by synthesis is a dominated technology, and its accuracy is limited by the fidelity of polymerases, the error rates of which are on the order of $10^{-5}$ to $10^{-7}$ per base pair from commercially available products.[4, 5] Given that the somatic mutation rate in human B and T lymphocytes and in fibroblasts are on the order of 2 to 10 mutations per diploid genome per cell division,[6] an ideal DNA sequencer should have an error rate lower than the mutation rate of ~$10^{-9}$ per base. Moreover, since approximately 50% of the human genome is comprised of repeats with their lengths in a range of 2 to 100,000 bp,[7] the sequencer should have a read length of >100 kbp, and ideally be able to read a chromosome from one end to another. For use in clinics, it should have a single molecule sensitivity for rare genetic variants, be able to sequence a human genome for less than $100, and simple to operate.[8]

Sequencing by protein nanopores has proven that a DNA sequence can directly be read out based on physical properties of nucleobases. As an example, MinION—the commercial version of a protein nanopore sequencer—can currently achieve a read-length 98 kb[9] while the theoretical read length is unlimited. However, the nanopore sequencing has a high error rate per base read (~15%). In addition to stochastic motions of the single DNA molecule in the pore, the error rate is due to the overlapped ionic current levels, as five nucleotides contribute to a current blockade in the nanopore,[10] which results in $4^5$ or 1054 possible 5-mers needed to be assigned, let alone the existence of modified bases in genome. Although improved data analysis has increased the accuracy of MinION significantly,[11] a technology breakthrough is essential to improve the spatial resolution of nanopores to a single nucleotide so that the assignment will be reduced to distinguishing among the four naturally occurring nucleobases plus their various modified forms. Thinner nanopores have been studied to improve the resolution of DNA sequencing. For example, it has been demonstrated that a Mycobacterium smegmatis porin A (MspA) pore reads DNA by a block of four nucleotides (quadromer) at a time, better than the α-hemolysin pore of the MinION.[12] The MspA nanopore has a funnel shape with a constriction region of 1.2 nm in diameter and 0.6 nm in length,[13] smaller than α-hemolysin that has a constriction site of 1.4 nm in diameter, followed by a β-barrel of about 5 nm long and 2 nm wide. Since an ionic blockade is sensitive to the DNA bases lying in the outsides of a nanopore as well,[14] it is unlikely for the ionic measurement to achieve a single nucleotide resolution ever in an atomically thin nanopore (such as a graphene nanopore).

Electron tunneling in a nanogap offers an alternative readout to improve the accuracy of nanopore sequencing. Zwolak and DiVentra first proposed to sequence DNA using changes in tunnel current flowing transverse to the DNA axis.[15] Taniguchi and Kawai et al. have demonstrated that nucleoside and deoxynucleoside monophosphates can generate characteristic tunneling currents through bare gold gaps of 0.8 to 1.0 nanometer wide.[16, 17] This is too small for a gap size to pass an intact single stranded DNA. A second problem with bare gold electrodes lies in strong chemisorption of adenine[18, 19, 20] and rapid contamination on their surfaces.

U.S. Pat. No. 8,628,649 discloses a Recognition Tunneling (RT) technique to read nucleobases using recognition molecules covalently attached to two electrodes that interspace a nanogap (~2.5 nm wide). The recognition molecule is able to effectively interact with each individual nucleobase to generate distinguishable electrical signals, so-called a universal reader. Since each nucleobase contains multiple hydrogen bonding sites, Liang et al.'s universal reader, 4(5)-(2-mercaptoethyl)-1H-imidazole-2-carboxamide (Iz) was designed to bear multiple hydrogen bond donors and acceptors.[21] Iz is extremely versatile and its interaction goes beyond nucleobases, such as with amino acids, peptides, and carbohydrates.[23, 24] Thus, there remains a need for a highly selective universal reader that only recognizes nucleobases.

Citation of any reference in this section is not to be construed as an admission that such reference is prior art to the present disclosure.

SUMMARY

The present disclosure provides an apparatus and a method for determining the sequence of a nucleic acid. The apparatus comprises electrodes that form a tunnel gap through which the nucleic acid can pass. The electrodes comprise a reagent that is capable of selectively interacting with a nucleobase of the nucleic acid sequence. When the reagent interacts with a nucleobase, a detectable signal is produced and used to identify the nucleobase of the nucleic acid. Advantageously, the apparatus of this disclosure is specific to identifying nucleic acids.

The present disclosure also provides compounds that can be used as reagents for attaching to electrodes used in the apparatus of the disclosure. The compound has formula (I):

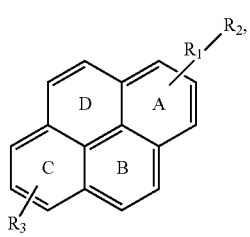
(I)

wherein $R_1$ is $(C_1-C_6)$ alkyl or $(C_1-C_6)$ alkoxy;
$R_2$ is selected from the group consisting of thiol, disulfide, and amine; and
$R_3$ is H, an electron withdrawing group or an electron donating group;
ring A or ring B is substituted with $R_1-R_2$; and
ring C or ring D is substituted with $R_3$;
provided that (i) when ring A is substituted with $R_1-R_2$, ring C is substituted with $R_3$; and (ii) when ring B is substituted with $R_1-R_2$, ring D is substituted with $R_3$.

BRIEF DESCRIPTION OF THE FIGURES

FIG. 9A shows primary parameters in the time domain. FIG. 9B shows secondary features in frequency domain. FIG. 9C shows secondary features in cepstrum domain.

FIG. 11A-FIG. 11T show RT spectra generated with: Iz functionalized tip and substrate at a set point of 4 pA and 0.5 V (FIG. 11A-FIG. 11F); Py functionalized tip and substrate at a set point of 2 pA and 0.5 V (FIG. 11G-FIG. 11L); Bn functionalized tip and substrate at a set point of 2 pA and 0.5 V (FIG. 11M-FIG. 11P); Bn functionalized tip and Py substrate at a set point of 2 pA and 0.5 V (FIG. 11Q-FIG. 11T).

DETAILED DESCRIPTION

Figure 1A:
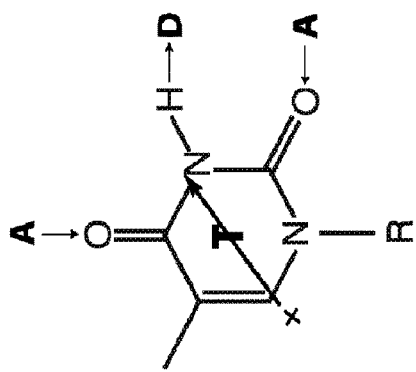
FIG. 1A shows hydrogen bonding sites (D: hydrogen bonding donor; A: hydrogen bonding acceptor) and dipole moments (R=CH$_3$) of DNA bases.
Figure 1A:
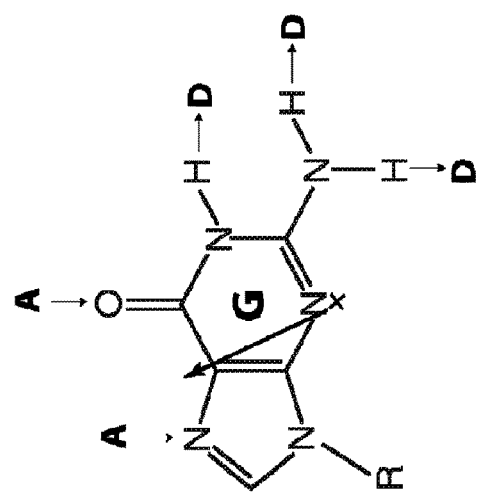
Figure 1A:
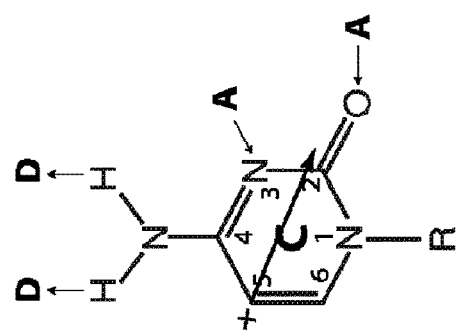
Figure 1A:
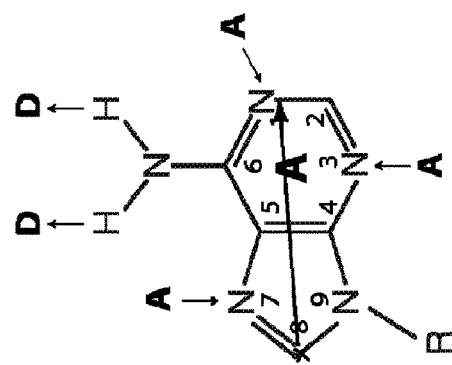
Figure 1B:
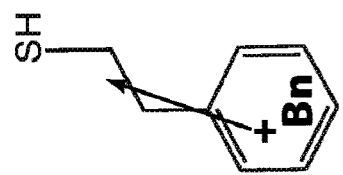
FIG. 1B shows the chemical structures of reader molecules Iz (imidazole-2-carboxamide), Py (pyrene), and Bn (benzene)
Figure 1B:
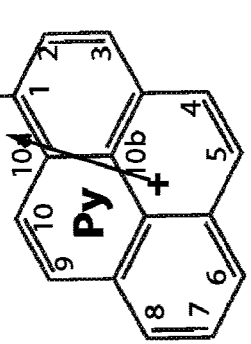
Figure 1B:
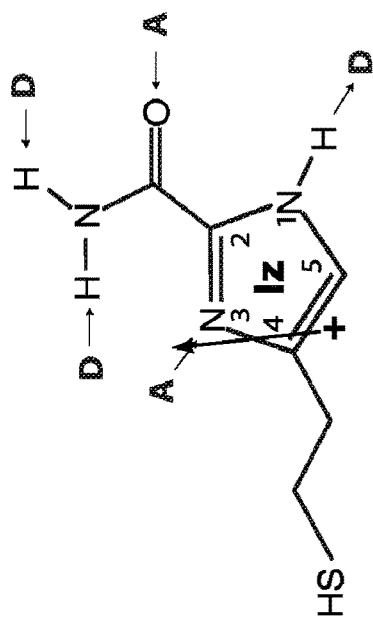
Figure 1C:
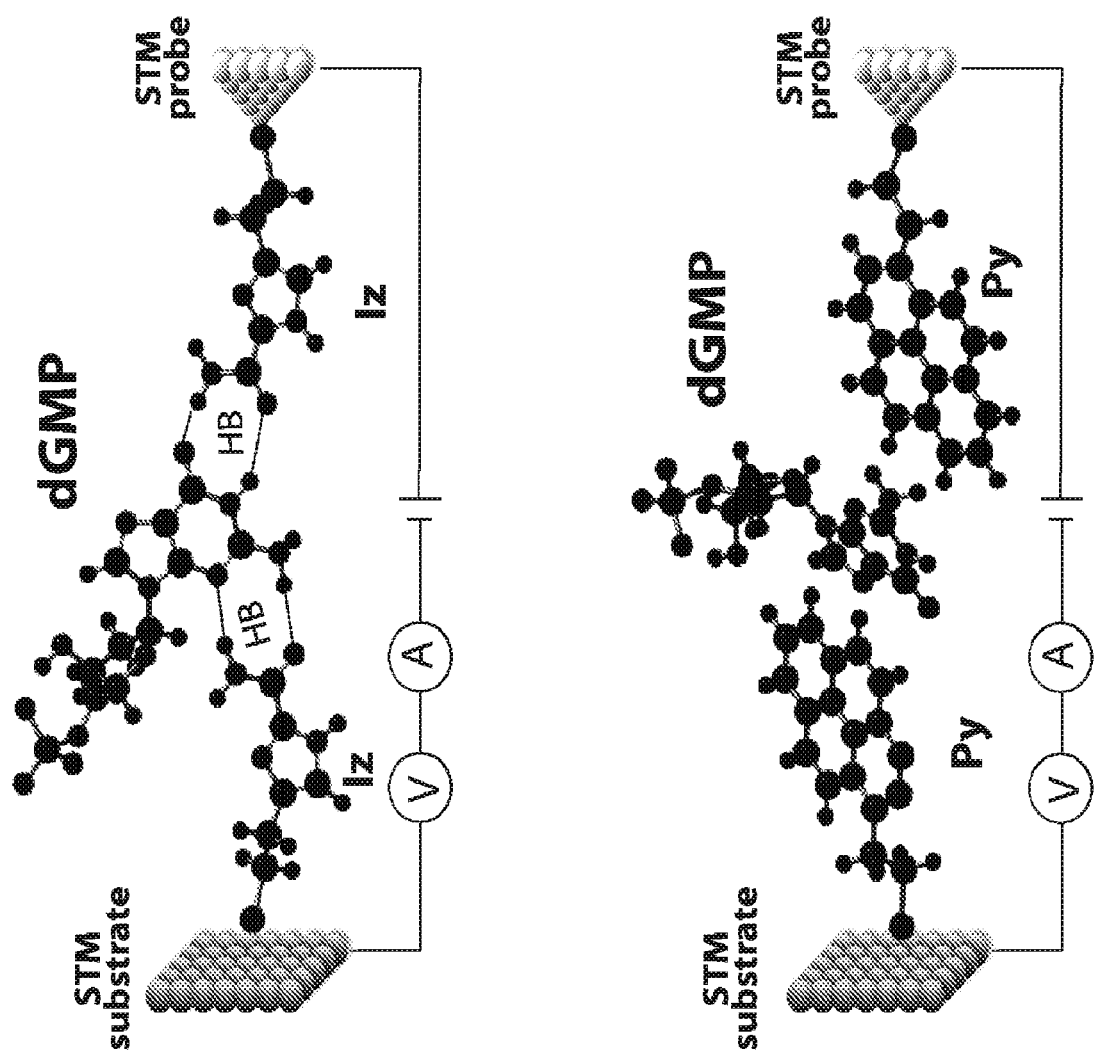
FIG. 1C shows computer modeling on reader molecules interacting with deoxyguanosine monophosphate (dGMP) in tunneling gaps created by fixing the distance between two sulfur atoms and then carrying out the energy minimization in software Spartan '14.

The invention includes the following:
(1.) An apparatus for analyzing a nucleic acid sequence in a sample, the apparatus comprising a chamber, wherein the chamber comprises:
 (a) a first and a second electrode that form a tunnel gap through which the nucleic acid sequence can pass;
 (b) a first reagent attached to the first electrode and a second reagent attached to the second electrode, wherein the first and the second reagent are capable of selectively interacting with a nucleobase of the nucleic acid sequence, wherein a detectable signal is produced when the nucleobase interacts with the first and second reagent.
(2.) An apparatus for selectively analyzing a nucleic acid sequence in a sample, the apparatus comprising a chamber, wherein the chamber comprises
 (a) a first and a second electrode that form a tunnel gap through which the nucleic sequence can pass;
 (b) a first reagent attached to the first electrode and a second reagent attached to the second electrode, wherein the first and the second reagent comprise an aromatic compound,
 wherein a detectable signal is produced when the nucleobase of the nucleic acid sequence interacts with the first and second reagent.
(3.) The apparatus according to the above (1.) or (2.), wherein the first and/or second electrode comprise a metal selected from the group consisting of palladium, gold, grapheme, carbon nanotube, and molybdenum disulphide.
(4.) The apparatus according to the above (1.) or (2.), wherein the first and/or second electrode comprise palladium.
(5.) The apparatus according to any one of the above (1.) to (4.), wherein the first and second reagent are the same.
(6.) The apparatus according to any one of the above (1.), (3.) or (4.), wherein the first and/or second reagent is an aromatic compound.
(7.) The apparatus according to the above (2.) or (6.), wherein the aromatic compound is selected from the group consisting of pyrene, benzene, anthracene, benzo[e]pyrene, 2-(phenylethynyl)pyrene, 2-phenyl pyrene, 3-nitro-1H-pyrrole and 5-nitro-1H-indole, wherein the polycyclic aromatic compound is unsubstituted or substituted with a substituent selected from nitro, phenyl, $(C_1-C_6)$alkyl substituted with phenyl, $(C_2-C_6)$alkenyl substituted with phenyl and $(C_2-C_6)$alkynyl substituted with phenyl.
(8.) The apparatus according to the above (7.), wherein the aromatic compound is selected from the group consisting of pyrene, 1-(2-mercaptoethyl)pyrene, nitrobenzene, 2-nitroanthracene, benzo[e]pyrene, 2-(phenylethynyl)pyrene, 2-phenyl pyrene, 3-nitro-1H-pyrrole and 5-nitro-1H-indole.

(9.) The apparatus according to the above (7.), wherein the aromatic compound is a pyrene.

(10.) The apparatus according to the above (9.), wherein the aromatic compound is a pyrene substituted with ($C_1$-$C_6$) mercaptoalkyl.

(11.) The apparatus according to any one of the above (1.) to (10.), wherein the aromatic compound is 1-(2-mercaptoethyl)pyrene.

(12.) The apparatus according to any one of the above (1.) to (4.), wherein the aromatic compound comprises a thiol, disulfide or amine.

(13.) The apparatus according to the above (12.), wherein the aromatic compound comprises a thiol.

(14.) The apparatus according to any one of the above (1.) to (13.), wherein the tunnel gap has a width of about 1.0 nm to about 5.0 nm.

(15.) The apparatus according to any one of the above (1.) to (14.), further comprising a detector for measuring the detectable signal.

(16.) The apparatus according to any one of the above (1.) to (15.), further comprising a system for introducing and removing buffer and the sample into the chamber.

(17.) The apparatus according to any one of the above (1.) to (16.), further comprising a system for analyzing the detectable signal.

(18.) The apparatus according to any one of the above (1.) to (17.), wherein the sample is a biological sample.

(19.) The apparatus according to any one of the above (1.) to (18.), wherein the nucleic acid is DNA.

(20.) The apparatus according to any one of the above (1.) to (18.), wherein the nucleic acid is RNA.

(21.) The apparatus according to any one of the above (1.) to (18.), wherein the nucleic acid is PNA (22.) The apparatus according to any one of the above (1.) to (18.), wherein the nucleic acid is XNA (23.) The apparatus according to any one of the above (1.) to (18.), wherein the nucleic acid comprises unnatural bases.

(24.) A compound of formula (I):

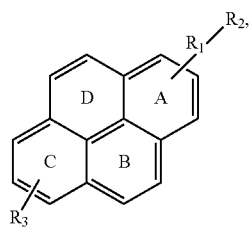

(I)

wherein $R_1$ is ($C_1$-$C_6$) alkyl or ($C_1$-$C_6$) alkoxy;
$R_2$ is selected from the group consisting of thiol, disulfide, and amine; and
$R_3$ is H, an electron withdrawing group or an electron donating group;
ring A or ring B is substituted with $R_1$-$R_2$; and
ring C or ring D is substituted with $R_3$;
provided that (i) when ring A is substituted with $R_1$-$R_2$, ring C is substituted with $R_3$; and (ii) when ring B is substituted with $R_1$-$R_2$, ring D is substituted with $R_3$.

(25.) The compound of the above (24.), wherein $R_1$ is ($C_1$-$C_6$) alkyl.

(26.) The compound of the above (24.), wherein $R_1$ is ($C_1$-$C_3$) alkyl.

(27.) The compound of the above (24.), wherein $R_1$ is ethyl.

(28.) The compound of any one of the above (24.) through (27.), wherein $R_2$ is thiol.

(29.) The compound of any one of the above (24.) through (28.), wherein $R_3$ is H, —$NO_2$ or $CH_3$.

(30.) The compound of any one of the above (24.) through 25, wherein $R_3$ is H.

(31.) The compound of the above (24.), wherein said compound is formula (Ia):

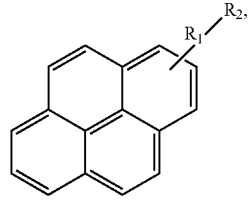

(Ia)

wherein $R_1$ is ($C_1$-$C_6$) alkyl or ($C_1$-$C_6$) alkoxy; and
$R_2$ is selected from the group consisting of thiol, disulfide, and amine.

(32.) The compound of the above (31.), wherein $R_1$ is ($C_1$-$C_6$) alkyl.

(33.) The compound of the above (31.), wherein $R_1$ is ($C_1$-$C_3$) alkyl.

(34.) The compound of the above (31.), wherein $R_1$ is ethyl.

(35.) The compound of any one of the above (31.) through (34.), wherein $R_2$ is thiol.

(36.) A method of determining the sequence of a nucleic acid, the method comprising
　(a) providing an apparatus according to any one of the above (1.) to (23.);
　(b) passing a nucleic acid through the tunnel gap;
　(c) detecting the signal produced when a nucleobase of the nucleic acid interacts with the first and second reagent;
　(d) from the signal detected in (c), identifying the nucleobase of the nucleic acid; and
　(e) repeating steps (b) through (d);
　(f) from the nucleobases identified in (d), determining the sequence of the nucleic acid.

(37.) The method of the above (36.), wherein step (c) comprises detecting an electrical current.

Definitions

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The term "($C_1$-$C_6$) alkyl" refers to saturated linear or branched hydrocarbon structures having 1, 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl, and "butyl" includes n-butyl, sec-butyl, iso-butyl and tert-butyl. Examples of "($C_1$-$C_6$) alkyl" include methyl, ethyl, n-propyl, iso-propyl, n-butyl, tert-butyl, n-pentyl, n-hexyl, and the like.

The term "($C_1$-$C_3$) alkyl" refers to saturated linear or branched hydrocarbon structures having 1, 2 or 3 carbon atoms. When an alkyl residue having a specific number of carbons is named, all geometric isomers having that number of carbons are intended to be encompassed; thus, for example, "propyl" includes n-propyl and iso-propyl. Examples of "($C_1$-$C_3$) alkyl" include methyl, ethyl, n-propyl and iso-propyl.

The term "($C_2$-$C_6$) alkenyl" refers to a straight-chain or branched unsaturated hydrocarbon radical having 2, 3, 4, 5 or 6 carbon atoms and a double bond in any position, e.g., ethenyl, 1-propenyl, 2-propenyl (allyl), 1-butenyl, 2-butenyl, 3-butenyl, 1-methylethenyl, 1-methyl-1 propenyl, 2-methyl-2-propenyl, 2-methyl-1-propenyl, 1-methyl-2-propenyl, 1-hexenyl, 2-hexenyl, 3-hexenyl, 2-methyl-2-pentenyl, 4-methyl-2-pentenyl, 4-methyl-1-pentenyl, 3-methyl-1-pentenyl, and the like.

The term "($C_2$-$C_6$)alkynyl" refers to a straight chain or branched hydrocarbon having 2, 3, 4, 5 or 6 carbon atoms and including at least one carbon-carbon triple bond. Examples of "($C_2$-$C_6$)alkynyl" include ethynyl, propynyl, 1-butynyl, 2-butynyl, 1-pentynyl, 2-pentynyl, 1-hexynyl, 2-hexynyl, 3-hexynyl, 4-methyl-2-pentynyl and the like.

The term "($C_1$-$C_6$)alkoxy" refers to —O—($C_1$-$C_6$)alkyl. Examples of "($C_1$-$C_6$)alkoxy" include methoxy, ethoxy, propoxy, n-propoxy, iso-propoxy, butoxy, n-butoxy, sec-butoxy, tert-butoxy, pentoxy, hexyloxy, and the like.

The term "($C_1$-$C_3$)alkoxy" refers to —O—($C_1$-$C_3$)alkyl. Examples of "($C_1$-$C_6$)alkoxy" include methoxy, ethoxy, propoxy, n-propoxy and iso-propoxy.

The term "electron withdrawing group" refers to an atom or group that draws electron density from neighboring atoms towards itself. Examples of "electron withdrawing groups" include halo, —CN, —$CF_3$, —$NO_2$, —SH, —C(O)H, —C(O)—($C_1$-$C_6$)alkyl, —C(O)O—($C_1$-$C_6$)alkyl, —C(O)OH, —C(O)—$C_1$, —$SO_2$OH, —S(O)$_2$NHOH, —$NH_3$, —N(($C_1$-$C_6$)alkyl)$_3$ and the like.

The term "electron donating group" refers to an atom or a group that donates some of its electron density to neighboring atoms. Examples of "electron donating groups" include —OH, —$NH_2$, —N(($C_1$-$C_6$)alkyl)$_2$, NHC(O)($C_1$-$C_6$)alkyl), —OC(O)($C_1$-$C_6$)alkyl), ($C_1$-$C_6$)alkyl), phenyl, —CH=C(($C_1$-$C_6$)alkyl))$_2$ and the like.

The term "Peptide Nucleic Acid" or "PNA" is a non-naturally occurring polymer comprising a polyamide backbone, and purine and pyrimidine bases linked thereto.

The term "Xeno Nucleic Acid" or "XNA" is a non-naturally occurring polymer in which the deoxyribose or ribose groups of DNA and RNA have been replaced. Examples of XNA include, but are not limited to, 1,5-anhydrohexitol nucleic acid (HNA), cyclohexene nucleic acid (CeNA), threose nucleic acid (TNA), glycol nucleic acid (GNA), locked nucleic acid (LNA), and peptide nucleic acid (PNA).

The term "unnatural base" refers to a non-naturally occurring molecule that is incorporated into a nucleic acid and can form a base pair with a natural base or another unnatural base. Unnatural bases are known in the art and examples include, but are not limited to, substituted or unsubstituted 2-aminopurine, substituted or unsubstituted imidazo[4,5-b]pyridine, substituted or unsubstituted pyrrolo[2,3-b]pyridine, substituted or unsubstituted pyridin-2-one, substituted or unsubstituted pyrrole-2-carbaldehyde, and substituted or unsubstituted 2-nitropyrrole, isoguanine, isocytosine, xanthosine, 2,4-diaminopyrimidine, 4-methylbenzimidazole, difluorotoluene, propynyl isocarbostyril, 7-azaindole, and 3-fluorobenzene.

The abbreviation "Py" refers to 1-(2-mercaptoethyl) pyrene.

The abbreviation "Iz" refers to 4(5)-(2-mercaptoethyl)-1H-imidazole-2-carboxamide.

The abbreviation "Bn" refers to (2-mercaptoethyl)benzene.

The abbreviation "RT" refers to Recognition Tunneling.

The abbreviation "AP" refers to abasic 5'-monophosphate.

Apparatus

The present disclosure provides an apparatus for selectively analyzing a nucleic acid sequence in a sample. The sample may be a biological sample and comprises DNA in one embodiment and RNA in a second embodiment. In one embodiment, the sample comprises DNA derived from a patient. The apparatus comprises a chamber, which, in turn comprises two electrodes. The two electrodes form a tunnel gap through which the sample of nucleic acid sequence can pass.

The electrodes may be made of any suitable material that can be functionalized with a reagent capable of interacting with a nucleobase. In one embodiment, the electrode is made from a metal. Suitable metals include palladium, gold, graphene, carbon nanotube, and molybdenum disulphide.

In one embodiment, the electrodes comprise a reagent that is capable of selectively interacting with a nucleobase of the nucleic acid sequence. In another embodiment, the electrodes comprise an aromatic compound that is capable of selectively interacting with a nucleobase of the nucleic acid sequence. The electrodes may be functionalized with the same reagent in one embodiment, a combination of reagents in a second embodiment, or individually functionalized with different reagents in a third embodiment.

In one embodiment, the reagent comprises a functional group that selectively attaches to the electrode surface. Suitable functional groups include a thiol, disulfide or amine. The selection of a functional group will depend on the electrode used. For example, when the electrode is made from gold or palladium, a reagent comprising a thiol may be used. When the electrode is made from graphene or carbon nanotubes, a reagent comprising an amine may be used.

In embodiments in which the electrode comprises an aromatic compound, the aromatic compound is selected from the group consisting of pyrene, benzene, anthracene, benzo[e]pyrene, 2-(phenylethynyl)pyrene, 2-phenyl pyrene, 3-nitro-1H-pyrrole and 5-nitro-1H-indole, wherein the aromatic compound is unsubstituted or substituted with a substituent selected from the group consisting of nitro, phenyl, ($C_1$-$C_6$)alkyl substituted with phenyl, ($C_2$-$C_6$)alkenyl substituted with phenyl and $(C_2-C_6)$alkynyl substituted with phenyl. In one embodiment, the aromatic compound is selected from the group consisting of pyrene, 1-(2-mercaptoethyl)pyrene, nitrobenzene, 2-nitroanthracene, benzo[e]pyrene, 2-(phenylethynyl)pyrene, 2-phenyl pyrene, 3-nitro-1H-pyrrole and 5-nitro-1H-indole. In another embodiment, the aromatic compound is a pyrene. In another embodiment, the aromatic compound is a pyrene substituted with $(C_1-C_6)$ mercaptoalkyl. In another embodiment, the aromatic compound is 1-(2-mercaptoethyl)pyrene. In another embodiment, the aromatic compound is a compound of formula (I), as disclosed herein.

The tunnel gap comprises the space between the two electrodes and can be adjusted to a width such that the nucleic acid fits into the gap. The gap width will vary depending on the reagent used and the nucleic acid to be analyzed. The gap may have a width from about 1 nm to about 5 nm, from about 1.5 nm to about 4.5 nm, from about 2 nm to about 4 nm, from about 2 nm to about 3.5 nm, from about 2 nm to about 3 nm, or from about 2 nm to about 2.5 nm.

Methods for determining suitable gap widths are known in the art. For example, U.S. Pat. No. 9,140,682 provides that suitable gap widths may be determined by using a device capable of a dynamically adjusting the gap. In some embodiments, a dynamically adjustable device may be used to analyze target units. In either case, the gap width may be determined or set as follows: The electrodes are approached together until a chosen tunnel current is achieved at a particular bias. For example, a current of 6 pA at 0.5V bias corresponds to a gap of 2.5 nm when tunneling in 1,2,4-trichlorobenzene. The gap is maintained by applying active servo control as is well known in the art for scanning tunneling microscopy.

When the nucleobase is passed through the tunnel gap, it interacts with the first and second reagent via π-π interactions. The interaction between the nucleobase and the reagent produce a detectable signal. The apparatus of this disclosure is highly specific to nucleobases.

In one embodiment, the apparatus further comprises one or more of the following: a detector for measuring the detectable signal, a system for introducing and removing buffer and the sample into the chamber, and a system for analyzing the detectable signal.

Compounds of Formula (I)

The present disclosure provides a compound of formula (I):

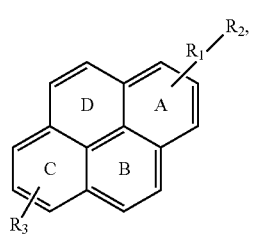

(I)

wherein $R_1$ is $(C_1-C_6)$ alkyl or $(C_1-C_6)$ alkoxy;
$R_2$ is selected from the group consisting of thiol, disulfide, and amine; and
$R_3$ is H, an electron withdrawing group or an electron donating group;
ring A or ring B is substituted with $R_1-R_2$; and
ring C or ring D is substituted with $R_3$;

provided that (i) when ring A is substituted with $R_1-R_2$, ring C is substituted with $R_3$; and (ii) when ring B is substituted with $R_1-R_2$, ring D is substituted with $R_3$.

In one embodiment, $R_1$ is $(C_1-C_3)$ alkyl or $(C_1-C_3)$ alkoxy. In another embodiment, $R_1$ is $(C_1-C_6)$ alkyl. In another embodiment, $R_1$ is $(C_1-C_6)$ alkoxy. In another embodiment, $R_1$ is $(C_1-C_3)$ alkyl. In another embodiment, $R_1$ is $(C_1-C_3)$ alkoxy. In another embodiment, $R_1$ is methyl or ethyl. In another embodiment, $R_1$ is methyl. In another embodiment, $R_1$ is ethyl. In another embodiment, $R_1$ is methoxy or ethoxy. In another embodiment, $R_1$ is methoxy. In another embodiment, $R_1$ is ethoxy.

In one embodiment, $R_2$ is thiol or disulfide. In another embodiment, $R_2$ is thiol or amine. In another embodiment, $R_2$ is disulfide or amine. In another embodiment, $R_2$ is thiol. In another embodiment, $R_2$ is disulfide. In another embodiment, $R_2$ is amine.

In one embodiment, $R_3$ is H or an electron withdrawing group. In another embodiment, $R_3$ is H or an electron donating group. In another embodiment, $R_3$ is an electron withdrawing group or an electron donating group. In another embodiment, $R_3$ is H. In another embodiment, $R_3$ is an electron withdrawing group. In another embodiment, $R_3$ is an electron donating group. In another embodiment, $R_3$ is H, —$NO_2$, or —$CH_3$. In another embodiment, $R_3$ is H or —$NO_2$. In another embodiment, $R_3$ is H or —$CH_3$. In another embodiment, $R_3$ is —$NO_2$ or —$CH_3$. In another embodiment, $R_3$ is —$NO_2$. In another embodiment, $R_3$ is —$CH_3$.

In one embodiment, $R_1$ is $(C_1-C_3)$ alkyl and $R_2$ is thiol. In another embodiment, $R_1$ is $(C_1-C_3)$ alkyl and $R_2$ is disulfide. In another embodiment, $R_1$ is $(C_1-C_3)$ alkyl and $R_2$ is amine. In another embodiment, $R_1$ is methyl and $R_2$ is thiol. In another embodiment, $R_1$ is methyl and $R_2$ is disulfide. In another embodiment, $R_1$ is methyl and $R_2$ is amine. In another embodiment, $R_1$ is ethyl and $R_2$ is thiol. In another embodiment, $R_1$ is ethyl and $R_2$ is disulfide. In another embodiment, $R_1$ is ethyl and $R_2$ is amine.

In one embodiment, $R_1$ is $(C_1-C_3)$ alkoxy and $R_2$ is thiol. In another embodiment, $R_1$ is $(C_1-C_3)$ alkoxy and $R_2$ is disulfide. In another embodiment, $R_1$ is $(C_1-C_3)$ alkoxy and $R_2$ is amine. In another embodiment, $R_1$ is methoxy and $R_2$ is thiol. In another embodiment, $R_1$ is methoxy and $R_2$ is disulfide. In another embodiment, $R_1$ is methoxy and $R_2$ is amine. In another embodiment, $R_1$ is ethoxy and $R_2$ is thiol. In another embodiment, $R_1$ is ethoxy and $R_2$ is disulfide. In another embodiment, $R_1$ is ethoxy and $R_2$ is amine.

The present disclosure also provides a compound of formula (Ia):

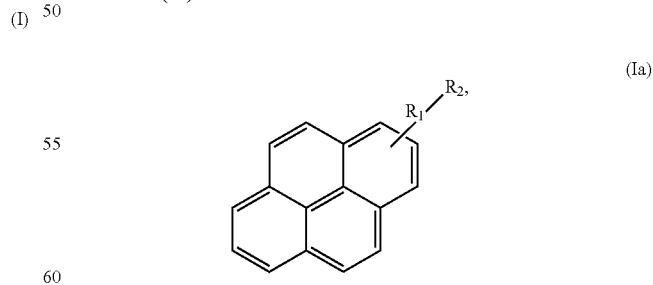

(Ia)

wherein $R_1$ is $(C_1-C_6)$ alkyl or $(C_1-C_6)$ alkoxy; and
$R_2$ is selected from the group consisting of thiol, disulfide, and amine.

In one embodiment, $R_1$ is $(C_1-C_3)$ alkyl or $(C_1-C_3)$ alkoxy. In another embodiment, $R_1$ is $(C_1-C_6)$ alkyl. In another embodiment, $R_1$ is $(C_1-C_6)$ alkoxy. In another embodiment, $R_1$ is ($C_1$-$C_3$) alkyl. In another embodiment, $R_1$ is ($C_1$-$C_3$) alkoxy. In another embodiment, $R_1$ is methyl or ethyl. In another embodiment, $R_1$ is methyl. In another embodiment, $R_1$ is ethyl. In another embodiment, $R_1$ is methoxy or ethoxy. In another embodiment, $R_1$ is methoxy. In another embodiment, $R_1$ is ethoxy.

In one embodiment, $R_2$ is thiol or disulfide. In another embodiment, $R_2$ is thiol or amine. In another embodiment, $R_2$ is disulfide or amine. In another embodiment, $R_2$ is thiol. In another embodiment, $R_2$ is disulfide. In another embodiment, $R_2$ is amine.

In one embodiment, $R_1$ is ($C_1$-$C_3$) alkyl and $R_2$ is thiol. In another embodiment, $R_1$ is ($C_1$-$C_3$) alkyl and $R_2$ is disulfide. In another embodiment, $R_1$ is ($C_1$-$C_3$) alkyl and $R_2$ is amine. In another embodiment, $R_1$ is methyl and $R_2$ is thiol. In another embodiment, $R_1$ is methyl and $R_2$ is disulfide. In another embodiment, $R_1$ is methyl and $R_2$ is amine. In another embodiment, $R_1$ is ethyl and $R_2$ is thiol. In another embodiment, $R_1$ is ethyl and $R_2$ is disulfide. In another embodiment, $R_1$ is ethyl and $R_2$ is amine.

In one embodiment, $R_1$ is ($C_1$-$C_3$) alkoxy and $R_2$ is thiol. In another embodiment, $R_1$ is ($C_1$-$C_3$) alkoxy and $R_2$ is disulfide. In another embodiment, $R_1$ is ($C_1$-$C_3$) alkoxy and $R_2$ is amine. In another embodiment, $R_1$ is methoxy and $R_2$ is thiol. In another embodiment, $R_1$ is methoxy and $R_2$ is disulfide. In another embodiment, $R_1$ is methoxy and $R_2$ is amine. In another embodiment, $R_1$ is ethoxy and $R_2$ is thiol. In another embodiment, $R_1$ is ethoxy and $R_2$ is disulfide. In another embodiment, $R_1$ is ethoxy and $R_2$ is amine.

In one embodiment, the compound of formula (Ia) is a 1-pyrene, 2-pyrene or 4-pyrene. In another embodiment, the compound of formula (Ia) is 1-pyrene or 2-pyrene. In another embodiment, the compound of formula (Ia) is 1-pyrene or 4-pyrene. In another embodiment, the compound of formula (Ia) is 2-pyrene or 4-pyrene. In another embodiment, the compound of formula (Ia) is 1-pyrene. In another embodiment, the compound of formula (Ia) is 2-pyrene. In another embodiment, the compound of formula (Ia) is 4-pyrene.

Methods of Use

The present disclosure also provides a method of determining the sequence of a nucleic acid. The method comprises providing an apparatus as disclosed herein. A sample comprising a nucleic acid is passed through the tunnel gap either by diffusion or through electrophoresis. When a nucleobase of the nucleic acid passes through the tunnel gap it interacts with the first and second reagent. This interaction is due to π-π stacking between the first and second reagent (e.g., the aromatic compound) and the nucleobase. The π-π stacking interaction causes a detectable signal. The signal so produced can be detected, e.g., by detecting an electrical current. From the detectable signal, the nucleobase is identified. These steps are repeated until the sequence of the nucleic acid is determined. The nucleic acid is DNA in one embodiment and RNA in a second embodiment.

In one embodiment, the method of determining the sequence of a nucleic acid further comprises providing a second apparatus comprising a third and a fourth electrode that form a tunnel gap through which the nucleic acid sequence can pass, wherein the third and the fourth reagents are each capable of forming a transient bond to a nucleobase of the nucleic acid, the third and fourth reagents being independently selected from the group consisting of mercaptobenzoic acid, 4-mercaptobenzcarbamide, imidazole-2-carboxide, and 4-carbamonylphenyldithiocarbamate. A sample comprising a nucleic acid is passed through the tunnel gap either by diffusion or through electrophoresis. When the transient bond between the third and fourth reagent and the nucleobase forms, a detectable signal is produced. From this detected signal, the nucleobase is identified. These steps are repeated until the sequence of the nucleic acid is determined. The nucleic acid is DNA in one embodiment and RNA in a second embodiment.

In embodiments in which the nucleic acid is sequenced using two apparatus, the first and second reagent are as defined in herein and the third and fourth reagent is 4(5)-(2-mercaptoethyl)-1H-imidazole-2-carboxamide (Iz). In one embodiment, the first and second reagent is 1-(2-mercaptoethyl)pyrene (Py) and the third and fourth reagent is 4(5)-(2-mercaptoethyl)-1H-imidazole-2-carboxamide (Iz).

The two apparatus sequencing method provides comprehensive information on genome sequences, for example, damages of DNA bases, which is lost in NGS due to the use of polymerases that can incorporate dAMP into the opposite of an abasic site ("A rule"[38]) or cause a frameshift.[39]

In order that this invention be more fully understood, the following examples are set forth. These examples are for the purpose of illustration only and are not to be construed as limiting the scope of the invention in any way.

EXAMPLES

Example 1—Computer Modeling

Figure 2:
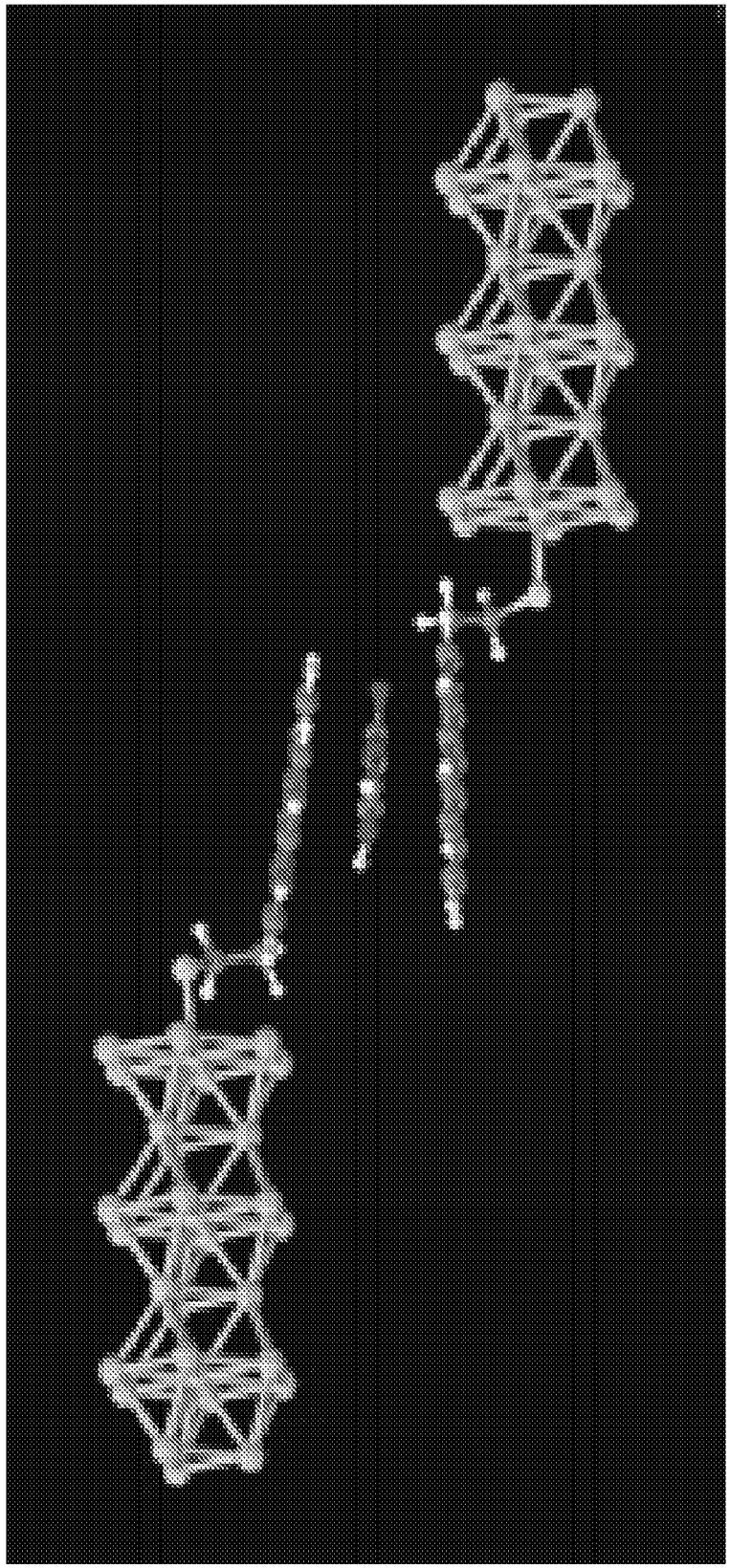
FIG. 2 shows an energy-minimized structure of a π-π stacked complex between two pyrene rings (attached to gold electrodes) and a guanine.
Figure 3:
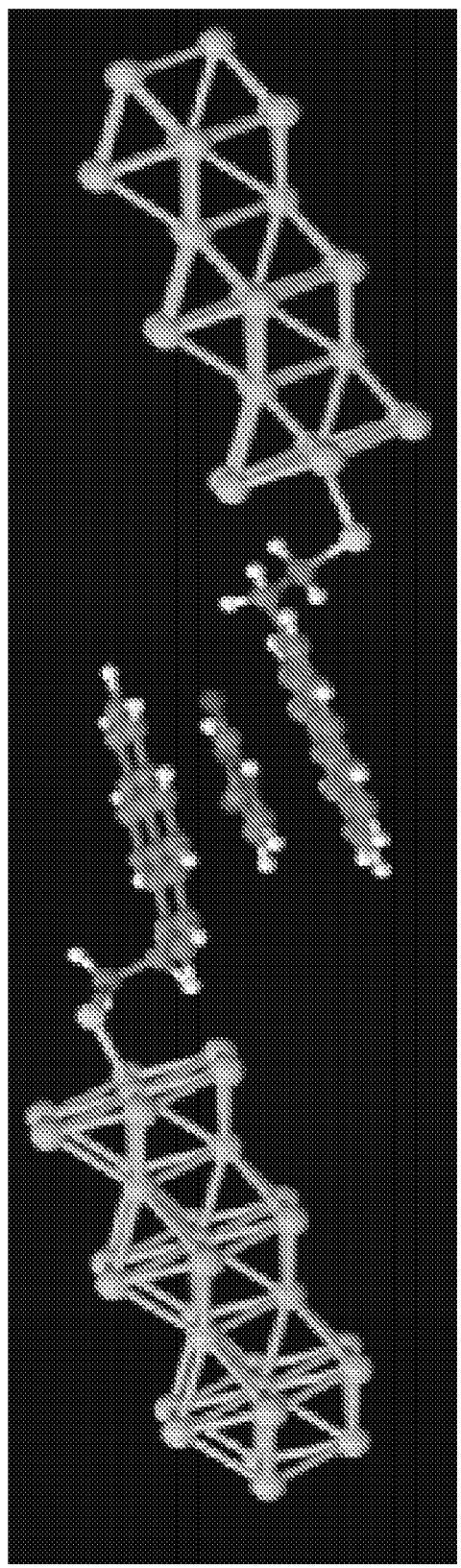
FIG. 3 shows an energy optimized structure of the π-π stacked complex between two pyrene rings (attached to gold electrodes/metal slabs) and a uracil.

To demonstrate the feasibility to distinguish between two DNA bases via the π-π, a computer model comprising two gold electrodes each carrying a Py molecule through a S—Au bond, which sandwiches a uracil base (FIG. 2) or a guanine base (FIG. 3) was built. With the gold atoms fixed, the system geometry is optimized to the minimum energy using Self-Consistent Charge-Tight-Binding DFT (SCC-DFTB) (Aradi B et al., *J. Phys. Chem. A* 2007, 111: 5678-5684; Elstner M, et al. *Physical Review B* 1998, 58(11): 7260-7268; and Porezag D, et al. *Physical Review B* 1995, 51(19): 12947-12957). Using first-principles quantum transport simulations, based on the nonequilibrium Green function formalism (Datta S. *Nanotechnology* 2004, 15(7): S433-S451) combined with tight-binding density functional theory (NEGF+DFTB) (Pecchia A, Carlo AD. Reports on Progress in Physics 2004, 67(8): 1497-1561; Pecchia A, et al., New Journal of Physics 2008, 10(6): 065022; and Carlo A D et al., In: Cuniberti G, Fagas G, Richter K (eds). Introducing Molecular Electronics: Lecture Notes in Physics vol. 680. Springer: Berlin, 2005, pp 153-184), changes in the total electronic currents through the system were examined with the voltage bias U applied between the gold electrodes in a range of 0.01 V to 1 V.

Figure 4:
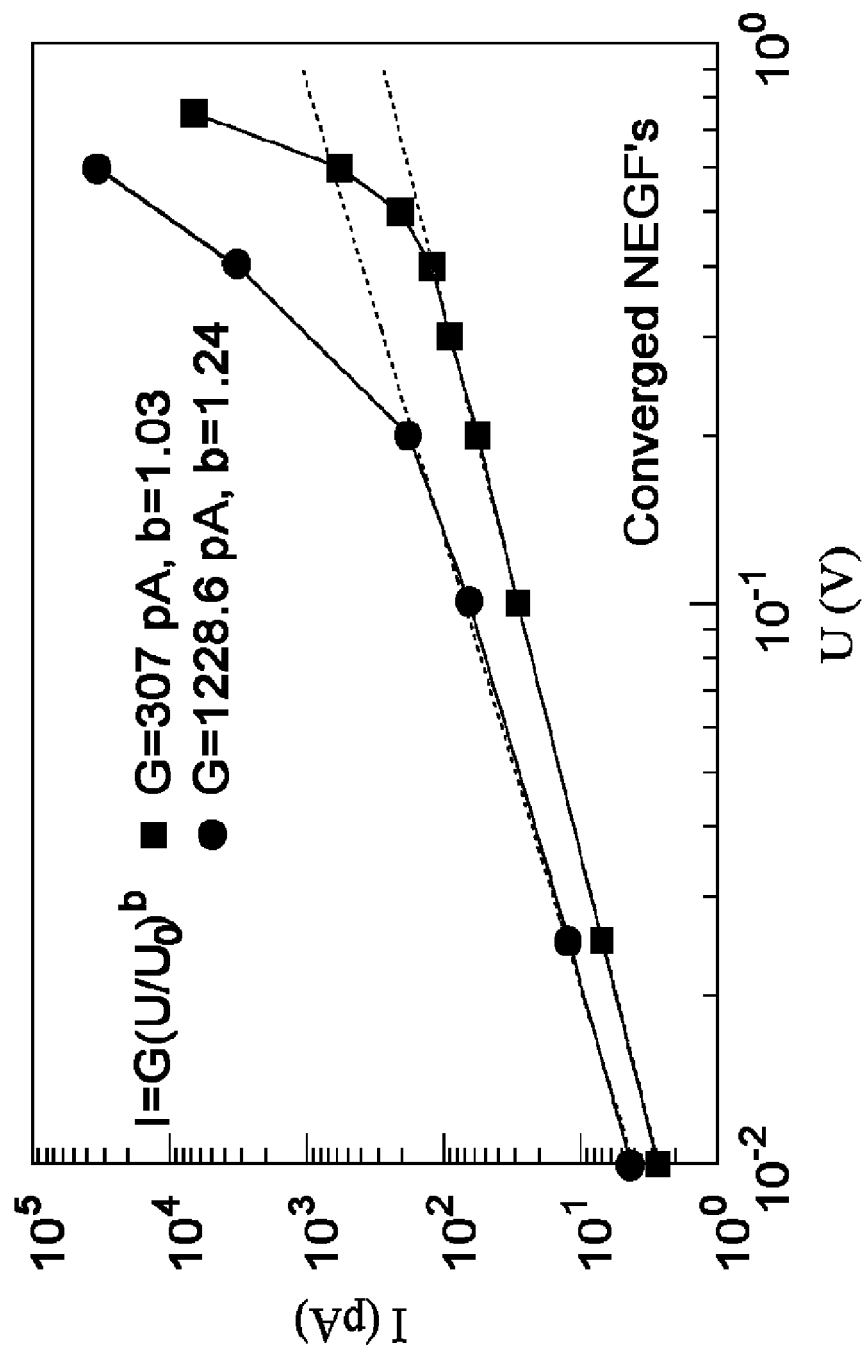
FIG. 4 shows a graph of calculated current vs bias. The top line with round dots is for the complex from FIG. 2 and the bottom line with square dots is the complex from FIG. 3.

As shown in FIG. 4, at lower bias the current response is a weak power dependence on the voltage (up to ~0.2 V for guanine, and to ~0.4 V for uracil), which can be fit to an analytic form $I=G(U/U_0)^b$, where for uracil G=307 pA, b=1.03 and for guanine G=1.228.6, b=1.24. In both cases $U_0$=1 V. This example shows that a sandwiched complex of pyrene with a purine (guanine) ring is more conductive than with the pyrimidine (uracil) in a nanogap when they are optimally stacked without steric hindrance.

Example 2—Synthesis

General Information.

Reagents and solvents were purchased from commercial suppliers (Sigma-Aldrich, Alfa Aesar, Fluka, TCI America) and used as received unless otherwise noted. All experiments requiring anhydrous conditions were performed in flame-dried glassware under nitrogen atmosphere. Reactions were monitored by thin layer chromatography (TLC) using glass plates pre-coated with silica gel (EMD Chemicals Inc.). Flash chromatography was performed in an automated flash chromatography system (CombiFlash R$_f$, Teledyne Isco, Inc.) with silica gel columns (60-120 mesh). Purchased 1-bromopyrene (95% purity) was further purified by silica gel flash chromatography eluting with hexane, dried at 40° C. overnight, and stored over drierite under vacuum. THF was freshly distilled over sodium prior to use. Nitrogen was flowed through drierite before it went into the reaction vessel. Ethylene oxide (1.2 M solution in dichloromethane) was stored over molecular sieves for two days before use. $^1$H NMR and $^{13}$C NMR spectra were recorded on Varian NOVA 400 (400 MHz) and Varian INOVA 500 (500 MHz) spectrometers at 25° C. at the Magnetic Resonance Research Center at Arizona State University. Chemical shifts (δ) are given in parts per million (ppm) and are referenced to the residual solvent peak (CDCl$_3$: $\delta_H$=7.26 ppm, CD$_3$OD: $\delta_H$=3.31 ppm, DMSO-d$_6$: $\delta_H$=2.50 ppm). Coupling constants (J) are expressed in hertz (Hz) and the values are rounded to the nearest 0.1 Hz. Splitting patterns are reported as follows: br, broad; s, singlet; d, doublet; dd, doublet of doublets; t, triplet; dt, doublet of triplets; q, quartet and m, multiplet. High resolution mass spectra (HRMS) are acquired at the Arizona State University CLAS High Resolution Mass Spectrometry Facility.

2.1—1-(2-mercaptoethyl)pyrene (Py)

1-(2-mercaptoethyl)pyrene (Py) can be synthesized according to Scheme 1.

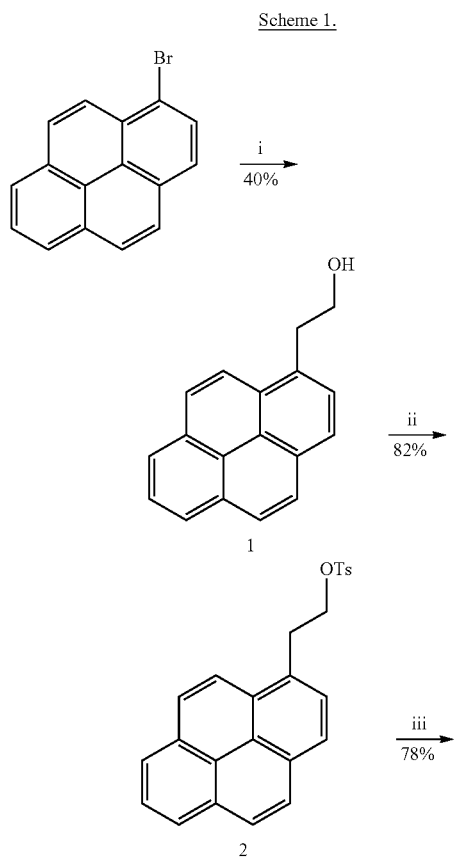

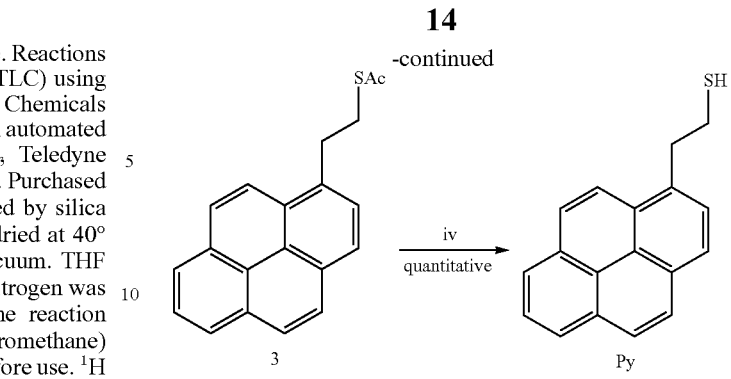

Reagents and Conditions:
(i) Mg in THF, and ethylene oxide; (ii) Tosyl chloride, ET$_3$N, CH$_2$Cl$_2$, 16 h at rt; (iii) Potassium thioacetate, DMF, 16 h at rt; (iv).

2-(pyren-1-yl)ethanol (1)

A solution of 1-bromopyrene (0.4 g, 1.42 mmol in 12 mL THF) was added onto magnesium turnings (0.1 g, 4.27 mmol) in a flame-dried Schlenk flask. It was refluxed at 70° C. while the solution turned into dark brown color and continued to reflux for another 2 h. The resulting solution was cooled in an ice bath followed by addition of ethylene oxide solution (3.6 mL, 4.27 mmol in 6 mL THF). The mixture was allowed to warm to room temperature and stirred for 12 h. It was cooled in an ice bath then hydrolyzed by careful addition of HCl (5 mL 10%), and extracted with ethyl acetate (20 mL×2). The combined organic layers were washed with brine (40 mL), dried over MgSO$_4$, filtered and evaporated to dryness by rotary evaporator. The product was separated through a silica gel column by flash chromatography using a gradient of ethyl acetate (0-20% for 3 h) in hexane. Compound 1 was obtained as yellow solid (0.14 g, 40%). $^1$H NMR (500 MHz, CDCl$_3$): δ 8.29 (d, J=9.0 Hz, 1H, ArH), 8.18 (d, J=8.0 Hz, 2H, ArH), 8.10-8.13 (m, 2H, ArH), 7.99-8.04 (m, 3H, ArH), 7.90 (d, J=8.0 Hz, 1H, ArH), 5.29 (s, br, 1H, OH), 4.09 (t, J=6.5 Hz, 2H, CH$_2$CH$_2$OH), 3.61 ppm (t, J=6.5 Hz, 2H, CH$_2$CH$_2$OH); $^{13}$C NMR (125 MHz, CDCl$_3$): δ 132.53, 131.52, 130.98, 130.42, 129.36, 128.07, 127.68, 127.57, 127.09, 126.06, 125.24, 125.19, 125.00, 124.97, 123.30, 63.95, 36.78, 29.85 ppm; HRMS (FAB+): found m/z 247.1129; calculated for C$_{18}$H$_{14}$O+H: 247.1123.

2-(Pyren-1-yl)ethyl 4-methylbenzenesulfonate (2)

Triethyl amine (0.08 mL, 0.55 mmol) was added into a solution of compound 1 (45 mg, 0.18 mmol) and tosyl chloride (52 mg, 0.28 mmol) in dichloromethane (1.5 mL) at room temperature. The resulting solution was stirred for 16 h, followed by addition of saturated sodium bicarbonate solution (5 mL), extracted with dichloromethane (3×10 mL). The combined organic phase was washed with brine (30 mL), dried over MgSO$_4$, filtered and evaporated to dryness by rotary evaporator. The residue was separated by flash chromatography through a silica gel column using a gradient of ethyl acetate (0-20% over a period of 3 h) in hexane. Compound 2 was obtained as a white solid (60 mg, 82%). $^1$H NMR (500 MHz, CDCl$_3$): δ 8.17 (q, J=7.5 Hz, 2H, ArH), 7.95-8.05 (m, 6H, ArH), 7.76 (d, J=7.5 Hz, 1H, ArH), 7.33 (d, J=8.5 Hz, 2H, Tosyl-ArH), 6.68 (d, J=8.5 Hz, 2H, Tosyl-ArH), 4.44 (t, J=7.0 Hz, 2H, CH$_2$CH$_2$OTs), 3.64 (t, J=7.0 Hz, 2H, CH$_2$CH$_2$OTs), 1.85 ppm (s, 3H, CH$_3$); $^{13}$C NMR (125 MHz, CDCl$_3$): δ 144.28, 132.23, 131.37, 130.73, 130.65, 129.96, 129.17, 128.87, 128.28, 127.80, 127.47, 127.40, 127.23, 126.08, 125.32, 125.13, 125.06, 124.80, 124.79, 122.52, 70.41, 33.06, 21.05 ppm; HRMS (FAB+): found m/z 401.1213; calculated for $C_{25}H_{20}O_3S$+H 401.1211.

S-(2-(pyren-1-yl)ethyl) ethanethioate (3)

Potassium thioacetate (24 mg, 0.206 mmol) was added to a solution of 2 (55 mg, 0.138 mmol) in DMF (1.5 mL). The resulting mixture was stirred for 16 h at room temperature. Brine (10 mL) was added into the reaction mixture, extracted with dichloromethane (2×10 mL). The combined organic phase was dried over $MgSO_4$, filtered and evaporated to dryness by rotary evaporator. The residue was separated by flash chromatography through a silica gel column using a gradient of ethyl acetate (0-5% over 3 h) in hexane. Compound 3 was obtained as a white solid (32 mg, 78%). $^1$H NMR (500 MHz, $CDCl_3$): δ 8.42 (d, J=9.5 Hz, 1H, ArH), 8.15-8.20 (m, 3H, ArH), 8.12 (d, J=8.0 Hz, 1H, ArH), 7.99-8.04 (m, 3H, ArH), 7.89 (d, J=8.0 Hz, 1H, ArH), 3.60 (t, J=8.0 Hz, 2H, CH$_2$CH$_2$S), 3.32 (t, J=8.0 Hz, 2H, CH$_2$C H$_2$S), 2.41 ppm (s, 3H, CH$_3$); $^{13}$C NMR (125 MHz, $CDCl_3$): δ 196.17, 134.14, 131.49, 131.00, 130.47, 129.01, 127.86, 127.56, 127.10, 126.02, 125.18, 125.17, 125.06, 125.03, 124.96, 123.30, 33.95, 30.87 ppm (two carbons were not identified); HRMS (FAB+): found m/z 305.1001; calculated for $C_{20}H_{16}OS$+H: 305.1000.

1-(2-Mercaptoethyl)pyrene (Py)

Pyrrolidine (2 µL, 24.6 µmol) was added into a solution of 3 (5 mg, 16.4 µmol) in ethanol (1 mL) and stirred for 30 min at room temperature. Solvent was evaporated to dryness by rotary evaporator to obtain Py (4.3 mg, 100%). $R_f$ on TLC: 0.18 (9:1 hexane/ethyl acetate). HRMS (APCI+): found m/z 263.0886; calculated for $C_{18}H_{14}S$+H: 263.0894.

Example 3—Monolayers on Palladium Substrates 3.1 Fabrication of Palladium Substrate Palladium substrates were made in ASU CSSER cleanroom using Lesker PVD75 Electron Beam Evaporator (Lesker #3). Pure (99.99%) palladium and titanium metal targets were bought from Kurt J. Lesker Company and circular silicon wafers (10 cm diameter) were purchased from Silicon Quest International. Prior to use, silicon wafers were cleaned with hydrofluoric acid, washed with isopropanol and nanopure water, and then blow-dried with a nitrogen flow. Over the silicon wafer a thin titanium adhesive layer (10 nm thick) was deposited, and then a palladium layer (200 nm thick) was deposited over titanium film. Small squares of 1×1 cm² were cut prior to use.

3.2 Monolayer Formation and Characterization 3.2.1 Rp Monolayer

Figure 5:
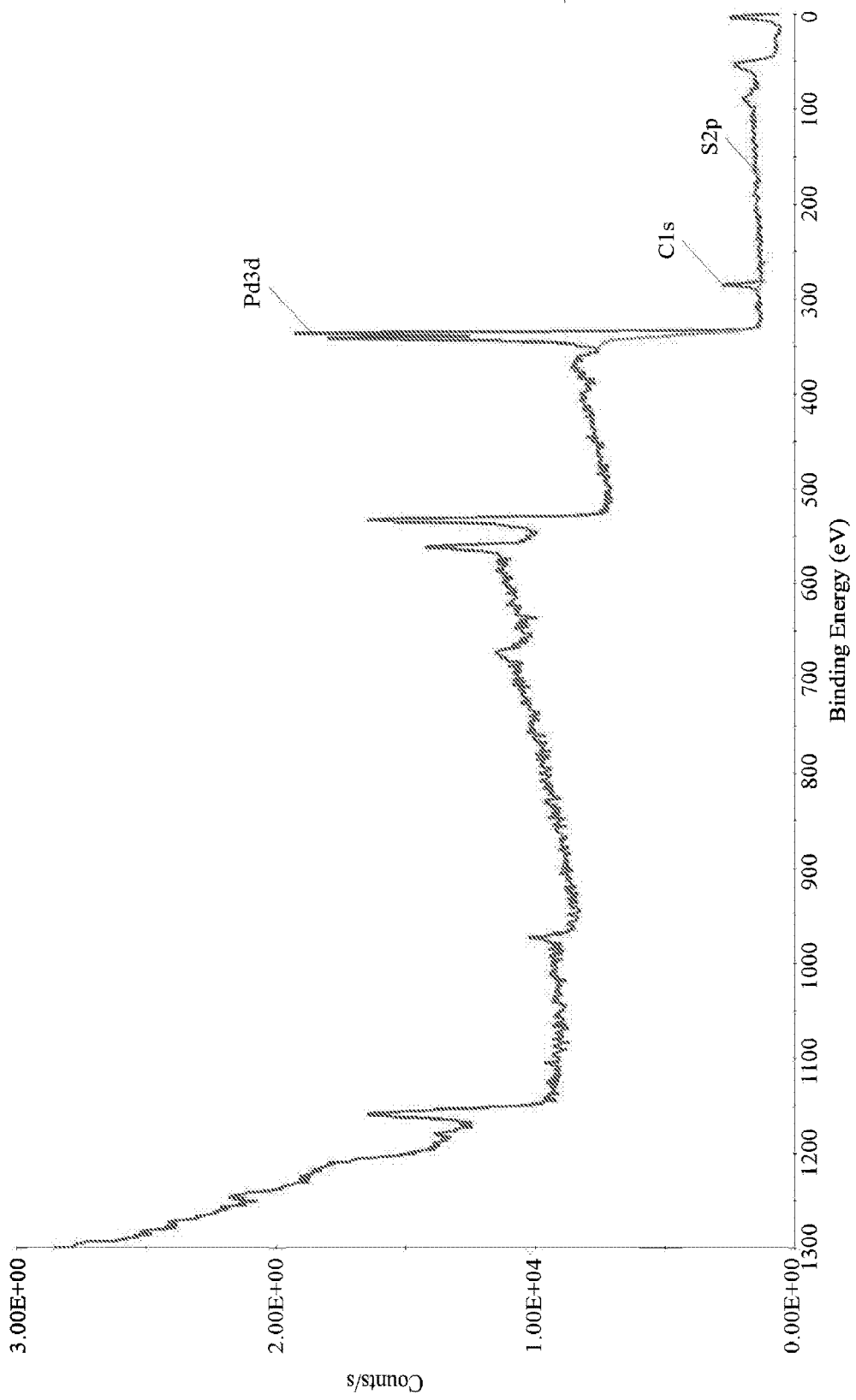
FIG. 5 show an XPS spectrum of Py SAM on Palladium.
Figure 6A:
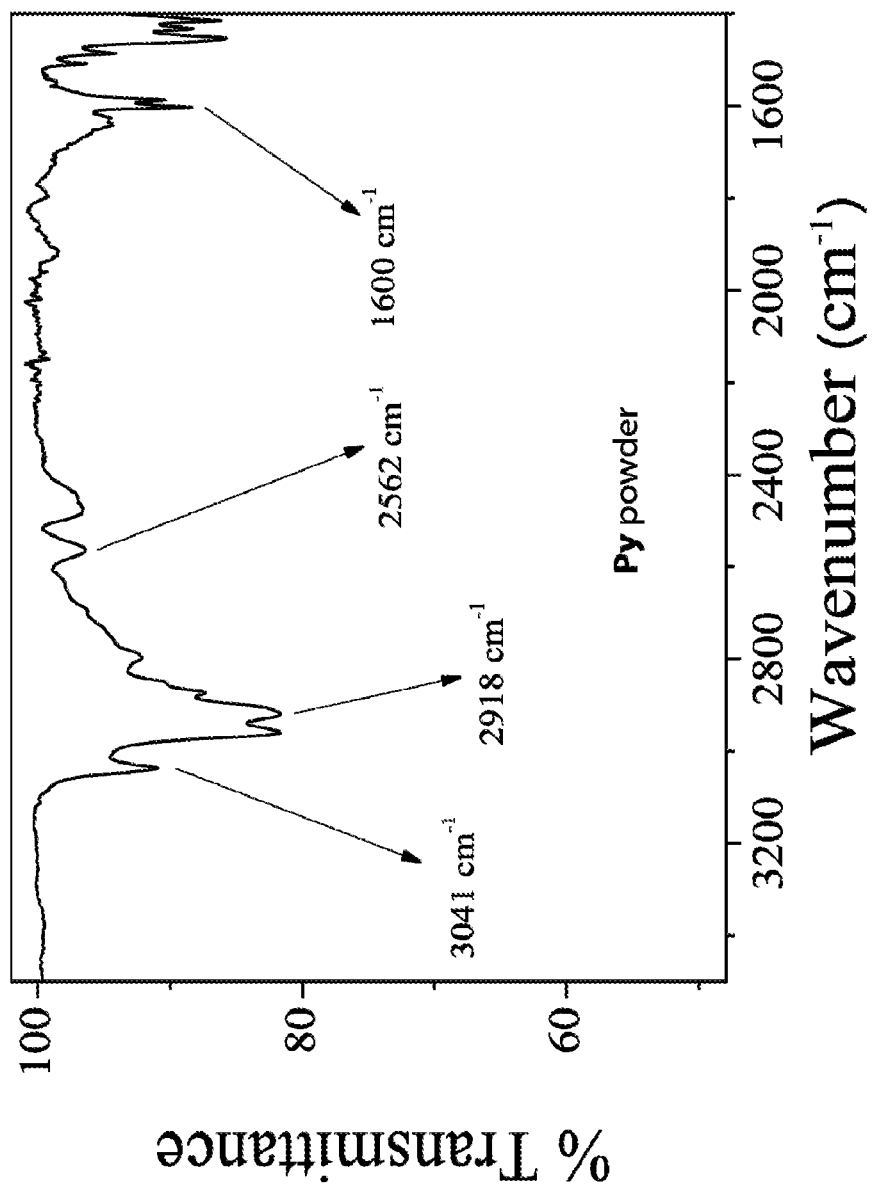
FIG. 6A and FIG. 6B show the FT-IR spectra of Py powder (FIG. 6A) and Py SAM on palladium (FIG. 6B).
Figure 6B:
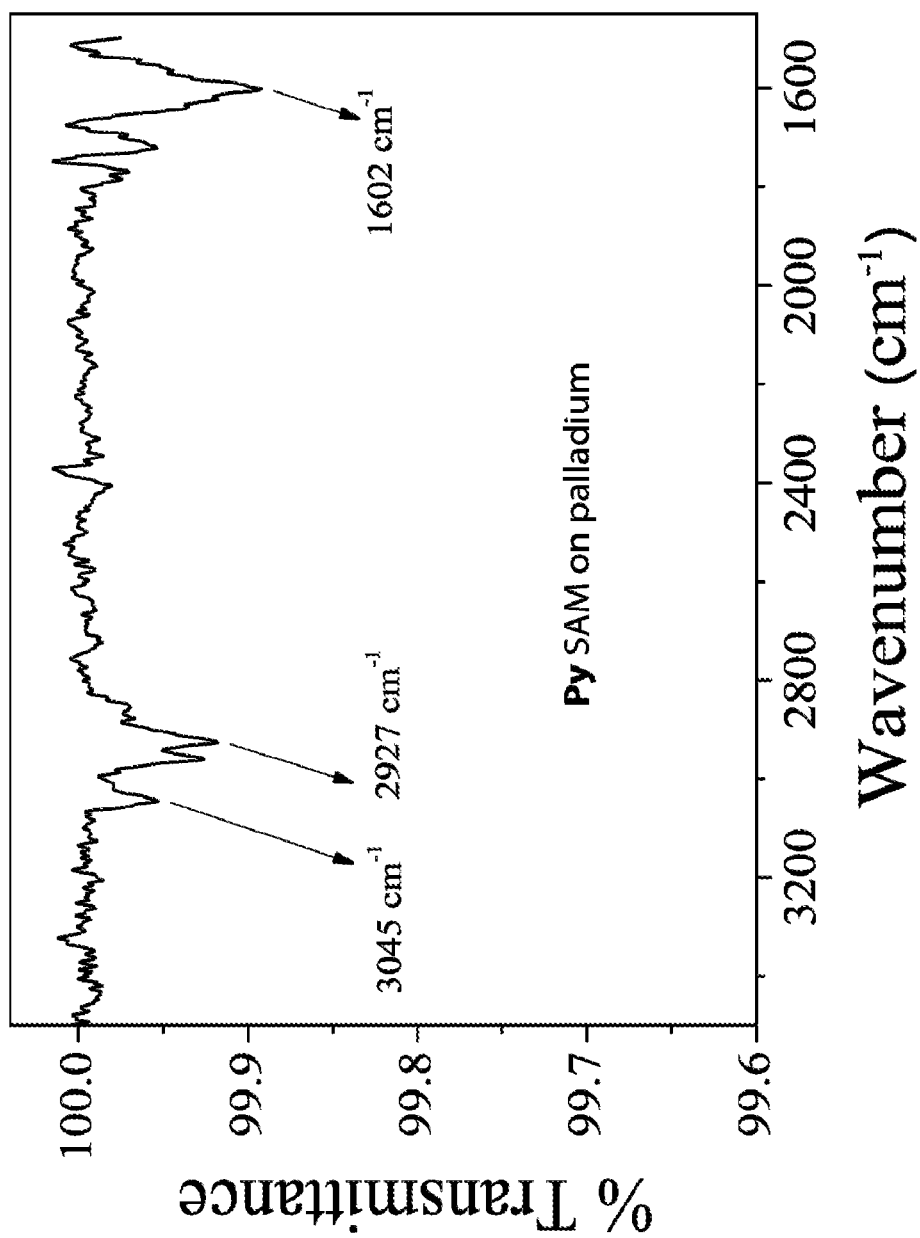

A solution of compound 3 (100 µM) and pyrrolidine (1 mM) in degassed ethanol was prepared. After 30 min, a palladium substrate was immersed into the solution for 8 h, washed thoroughly with ethanol, dried with a nitrogen flow, used immediately for the RT measurement. The Py monolayer was characterized with elliposometry and contact angle (Table 1), XPS (FIG. 5), and FTIR (FIG. 6A and FIG. 6B).

TABLE 1

Thickness* and contact angle** of Py SAM on palladium

| Thickness by Ellipsometry (Å) | Contact Angle (°) |
|---|---|
| 8.6 ± 0.6 | 67.8 ± 4.5 |

*Thickness of self-assembled monolayers were measured using LSE STOKES Ellipsometer with HeNelaser (632.8 nm wavelength) and 70° incident angle of measuring laser beam. Prior to functionalization, ellipsometric parameters of bare clean palladium substrates were measured and used for determination of the thickness of the functionalized substrates. Refractive index value for organic film was set as 1.46.
**Easydrop was used to measure water contact angle of SAM on palladium substrate. The data reported is an average of five measurements taken on each sample with a water droplet volume of 1 µL.

For the XPS experiments, X-ray photoelectron spectra were obtained using Al-Kα radiation (15 keV) at 6×10-10 mbar base pressure on VG ESCALAB 220i-XL photoelectron spectrometer. Wide scan spectra were recorded at 150 eV pass energy and high resolution spectra for C(1s), Pd(3d) and S(2p) were obtained at 20 eV pass energy. Elemental ratio of the SAM was calculated from area under the peaks of corresponding elements using CasaXPS software package. Table 2 shows the calculated elemental ratio and experimental elemental ratio.

TABLE 2

| Calculated Elemental Ratio for S:C | Found Elemental Ratio for S:C (from XPS) |
|---|---|
| 1:18 | 1:13.5 ± 1.5 |

For the FTIR experiments, the spectrum of powder sample was acquired with smart orbit (attenuated total reflection) and SAM spectra with SAGA (Specular Aperture Grazing Angle) accessory on Thermo Nicolet A Nicolet 6700 FT-IR (Thermo Electron CoPyoration) instrument equipped with a MCT detector. A background spectrum was recorded before recording the FT-IR of powder sample and a bare palladium substrate in case of monolayer sample. All the FT-IR data were subjected to baseline correction using the built-in spectrum program. The vibration around 3040 cm$^{-1}$ is assigned to aromatic C—H stretching, 1600 cm$^{-1}$ aromatic C—C stretching, 2925 cm$^{-1}$ aliphatic C—H stretching from methylene group, and 2564 cm$^{-1}$ s-h stretching, which is absent in SAM spectrum.

3.2.2 Bn Monolayer

Figure 7A:
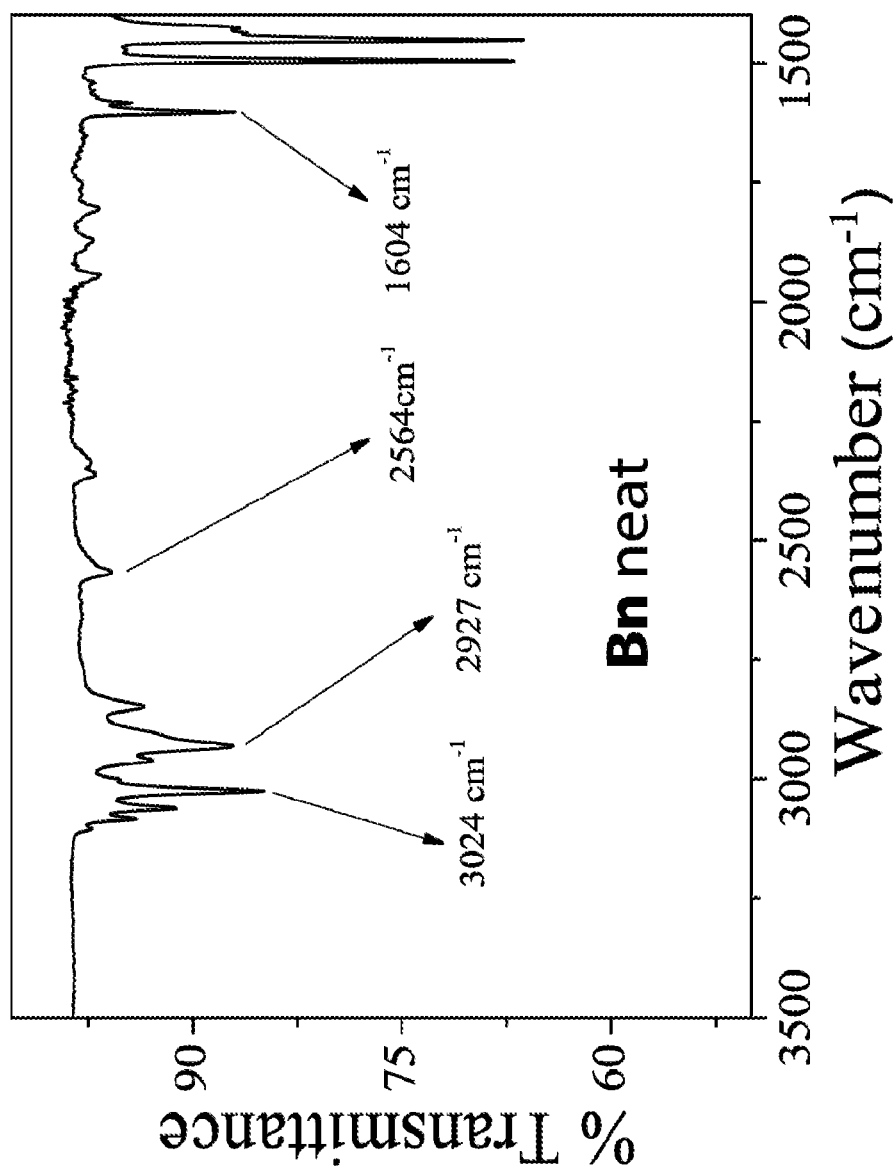
FIG. 7A and FIG. 7B show the FT-IR spectra of Bn neat (FIG. 7A) and Bn SAM on palladium (FIG. 7B).
Figure 7B:
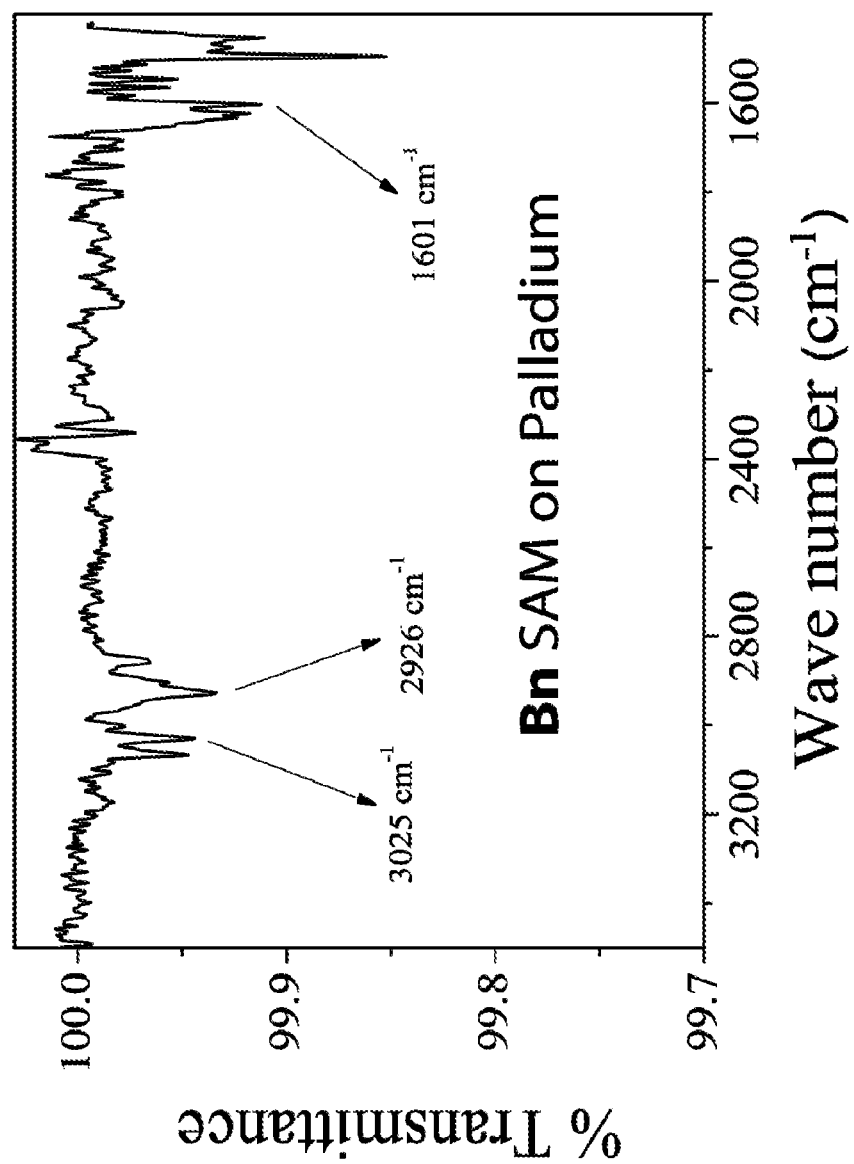

A palladium substrate was immersed in an ethanolic (degassed) solution of Bn (50 µM) for 2.5 h, washed thoroughly with ethanol, dried with a nitrogen flow, and used immediately. The Bn monolayer was characterized with elliposometry and contact angle following the protocol of Example 3.2.1 (Table 3), and FTIR (FIG. 7A and FIG. 7B)

TABLE 3

Thickness and contact angle of Bn SAM on palladium

| Thickness by Ellipsometry (Å) | Contact Angle (°) |
|---|---|
| 5.6 ± 0.9 | 79.5 ± 4.1 |

For the FTIR experiments, the spectrum of neat sample was acquired with SMART ORBIT (Attenuated Total Reflection) and SAM spectra with SAGA (Specular Aperture Grazing Angle) accessory on Thermo Nicolet A Nicolet 6700 FT-IR (Thermo Electron CoPyoration) instrument equipped with a MCT detector. A background spectrum was recorded before recording the FTIR of powder sample and a bare Palladium substrate in case of monolayer sample. All the FTIR data were subjected to baseline correction using the built-in SPECTRUM program. The vibration around 3020 cm$^{-1}$ is assigned to aromatic C—H stretching, ~1600 cm$^{-1}$ aromatic C—C stretching, ~2930 cm$^{-1}$ aliphatic C—H stretching from methylene group, and 2568 cm$^{-1}$ S—H stretching, which is absent in the SAM spectrum.

3.2.3 Iz Monolayer.

A palladium substrate was immersed in a degassed ethanolic solution of Iz (500 μM) for 16 h, washed thoroughly with ethanol, dried with a nitrogen flow, and used immediately (Chang S, et al. *Nanotechnology* 23, 425202 (2012).

This example confirms by contact angle measurements, elliposometry, FTIR and XPS that both Py and Bn could form monolayers on the Pd substrate.

Example 4—Surface Plasmon Resonance (SPR)

Figure 8:
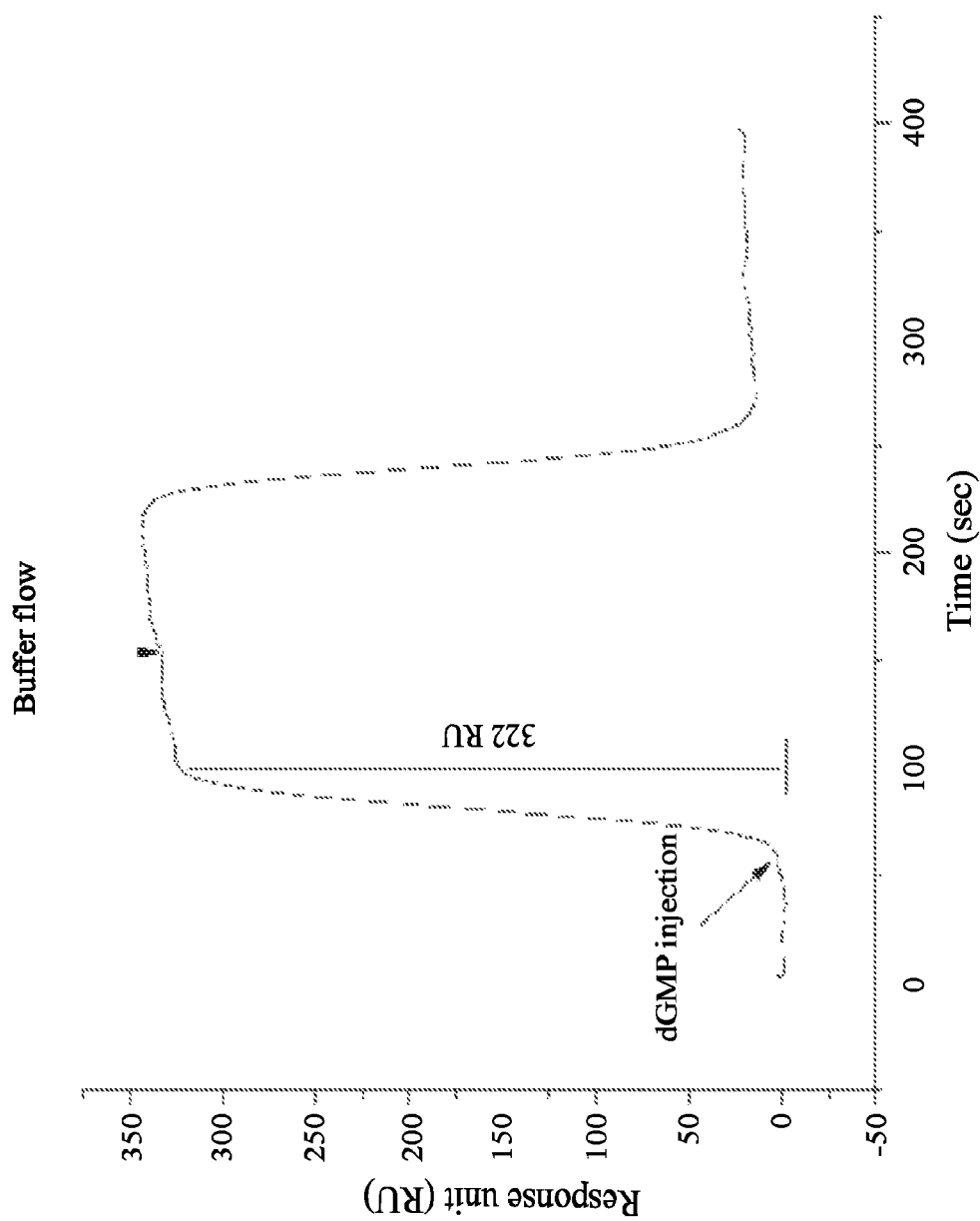
FIG. 8 shows a surface plasmon resonance sensorgram illustrating the response of a gold chip derivatized according to the present disclosure to dGMP.

A gold chip was immersed into an absolute ethanol solution of Py (100 μM) for 24 h, followed by rinsing with absolute ethanol and drying with a nitrogen flow, and used immediately. The instrument Bi 2000 from Biosensing Instrument was used for SPR measurements. The Py modified gold chip was mounted on the instrument and calibrated with 1% ethanol in a phosphate buffer, pH 7.4. A solution of dGMP (500 M) was flowed onto the chip at a rate of 50 ul/min over a period of 1.5 min, followed by flowing the PBS buffer (FIG. 8). Association ($k_{on}$) and dissociation rate constants ($k_{off}$) were determined using built-in Biosensing Instrument SPR data analysis software version 2.4.6 (Table 4).

TABLE 4

Kinetic parameters of dGMP on the pyrene monolayer[1]

| dGMP | $k_{on}$ (M$^{-1}$s$^{-1}$) | $k_{off}$ (s$^{-1}$) | $K_d^2$ (mM) | Res · sd |
|---|---|---|---|---|
| 500 uM | 41.60 ± 2.50 | 0.09 ± 0.01 | 2.46 ± 0.12 | 10.2 ± 1.4 |

[1]Each datum listed is an average of three measurements.
[2]$K_d = k_{off}/k_{on}$ This example shows that DNA nucleotides, such as dGMP, can be absorbed on the Py monolayer with an affinity of $K_d$=2.46 mM in aqueous solution.

Example 5—Recognition Tunneling Using Scanning Tunneling Microscope

In this example, Scanning Tunneling Microscope (STM) was used to create the tunnel nanogaps between a Pd probe and a Pd substrate, which were functionalized with Py, Iz, or a (2-mercaptoethyl)benzene control (Bn) prior to use.

5.1 DNA Monophosphate Solution

All of analytes were purchased from Sigma Aldrich with purity of ≥98% except AP (≥95%). Ultrapure water with specific resistance ~18 MΩ and organic carbon particle ~4 ppb from MilliQ system was used for solution preparation. Each analyte solution was prepared with a concentration of 100 μM in 1.0 mM phosphate buffer pH 7.4.

5.2 Functionalization of Palladium Probes

Probe preparation followed a known method.[10] A batch of 4 STM Probes were made by electrochemically etching palladium wires with 0.25 mm diameter (from California Fine Wires) in a mixed solution of con. hydrochloric acid (36% w) and ethanol (1:1), followed by insulation with high density polyethylene, which left the apexes open. Any probes with leakage current>1 pA were discarded and the rest were functionalized with reader molecules in the same procedure as described above for preparation of the monolayer, and used immediately for RT measurements.

5.3 Data Collection

The measurements were carried out in PicoSPM instrument (Agilent Technologies), interfaced with a customized Labview program. The sampling rate for tunnel current was 50 kHz. Prior to the experiment, the STM teflon cell was cleaned with piranha followed by vigorous rinsing with Milli-Q water and ethanol. After adding ~150 μL of phosphate buffer (1.0 mM, pH 7.4 to the STM cell, the functionalized palladium probe (with leakage current<1 pA; prepare in Example 5.2) and Pd-substrate were installed to the scanner. The probe was approached to the functionalized surface with a set value of 1.0 for integral and proportional gain at 2 pA current set-point and −500 mV bias (substrate negative). Then a few images were scanned to ensure that the probe was perfectly oriented over the substrate and the Pd crystal grains can be seen clearly. After that, the probe was withdrawn for 10 μm for 2 hours to ensure that there was no drift and minimal mechanical noise. Then the probe was engaged again and control data was recorded with a reduced value of integral and proportional gain (0.1). Once the tunnel junction was stabilized, the phosphate buffer was discarded and an analyte solution was introduced (typically 100 μM in 1.0 mM phosphate buffer, pH 7.4) to the liquid cell, and current recordings were collected under a predefined tip-substrate bias. Four naturally occurring DNA nucleoside monophosphates (dAMP, dCMP, dGMP and dTMP) and two sugar molecules (abasic 5'-monophosphate, designated as AP, and D-glucose) were used as analytes (prepared in Section 5.1). For each analyte, four data sets were collected separately with freshly made probes, substrates, and samples.

5.4 Data Analysis

5.4.1 Analysis of RT Raw Data

Data recorded in the time domain was characterized by peak height, averaged amplitude, peak width, and so on (FIG. 9A) using Matlab. First, the baseline tunneling current was shifted to zero and a threshold was set at 15 pA for the tunneling spikes. The peak height, averaged amplitude, peak width data were exported to OriginPro 2016 for the analysis and the curve fitting was performed using the built-in Levenberg-Marquardt algorithm. The results are listed in Table 5.

TABLE 5

| | | Py | | | | |
|---|---|---|---|---|---|---|
| | | dAMP | dCMP | dGMP | dTMP | Average |
| Peak height (pA) | Median | 9.74 ± 0.06 | 8.29 ± 0.03 | 8.92 ± 0.04 | 8.97 ± 0.03 | 8.98 ± 0.02 |
| | Mean | 10.34 ± 0.07 | 8.52 ± 0.03 | 9.28 ± 0.05 | 9.33 ± 0.04 | 9.36 ± 0.02 |
| | Sigma (σ) | 3.67 ± 0.08 | 2.03 ± 0.04 | 2.65 ± 0.05 | 2.67 ± 0.04 | 2.76 ± 0.03 |
| Averaged amplitude (pA) | Median | 4.64 ± 0.02 | 4.87 ± 0.01 | 4.41 ± 0.01 | 3.62 ± 0.01 | 4.39 ± 0.01 |
| | Mean | 4.91 ± 0.02 | 5.02 ± 0.01 | 4.62 ± 0.02 | 3.89 ± 0.01 | 4.61 ± 0.01 |
| | Sigma (σ) | 1.68 ± 0.02 | 1.26 ± 0.01 | 1.45 ± 0.02 | 1.52 ± 0.01 | 1.48 ± 0.01 |
| Peak width (ms) | Median | 0.378 ± 0.002 | 0.413 ± 0.001 | 0.395 ± 0.002 | 0.349 ± 0.001 | 0.384 ± 0.001 |
| | Mean | 0.397 ± 0.002 | 0.430 ± 0.001 | 0.412 ± 0.003 | 0.360 ± 0.001 | 0.400 ± 0.001 |
| | Sigma (σ) | 0.126 ± 0.002 | 0.125 ± 0.001 | 0.124 ± 0.003 | 0.090 ± 0.001 | 0.116 ± 0.001 |
| Spike Frequency | | 7.5 ± 2.2 | 8.1 ± 2.2 | 8.1 ± 4.7 | 12.4 ± 3.0 | 9.0 ± 1.7 |

| | | Iz | | | | |
|---|---|---|---|---|---|---|
| | | dAMP | dCMP | dGMP | dTMP | Average |
| Peak height (pA) | Median | 8.46 ± 0.03 | 8.88 ± 0.03 | 8.81 ± 0.03 | 8.75 ± 0.03 | 8.72 ± 0.02 |
| | Mean | 8.69 ± 0.03 | 9.16 ± 0.04 | 9.10 ± 0.03 | 9.02 ± 0.03 | 8.99 ± 0.02 |
| | Sigma (σ) | 2.03 ± 0.03 | 2.35 ± 0.04 | 2.35 ± 0.04 | 2.29 ± 0.03 | 2.26 ± 0.02 |
| Averaged amplitude (pA) | Median | 4.38 ± 0.01 | 4.45 ± 0.01 | 4.32 ± 0.01 | 4.33 ± 0.01 | 4.37 ± 0.01 |
| | Mean | 4.57 ± 0.01 | 4.67 ± 0.01 | 4.54 ± 0.01 | 4.54 ± 0.01 | 4.58 ± 0.01 |
| | Sigma (σ) | 1.37 ± 0.01 | 1.48 ± 0.01 | 1.45 ± 0.01 | 1.43 ± 0.01 | 1.43 ± 0.01 |
| Peak width (ms) | Median | 0.404 ± 0.002 | 0.404 ± 0.002 | 0.398 ± 0.003 | 0.404 ± 0.002 | 0.403 ± 0.001 |
| | Mean | 0.421 ± 0.003 | 0.421 ± 0.003 | 0.414 ± 0.003 | 0.420 ± 0.003 | 0.419 ± 0.002 |
| | Sigma (σ) | 0.123 ± 0.003 | 0.125 ± 0.003 | 0.119 ± 0.003 | 0.120 ± 0.003 | 0.122 ± 0.002 |
| Spike Frequency | | 6.9 ± 2.5 | 8.4 ± 6.4 | 8.9 ± 3.3 | 6.2 ± 0.8 | 7.6 ± 1.9 |

5.4.2 Extraction of Features from RT Data

RT spectrum were analyzed by defining two types of event signals, spikes and clusters. The spike is an individual single RT spectrum and the cluster is a subset of close spikes. To define a cluster, a Gaussian window (4096 data points and one-unit height) was applied to the center of each spike. Spike that lie within a region where the sum of the Gaussian windows continuously exceeds 0.1 were identified as belonging to a cluster. Although each independent tunneling spike was identified by having amplitude above 15 pA, the cluster includes all the spikes within the defined region. Table 6 lists features used to describe an individual spike.

TABLE 6

| | Feature Name | Feature Description |
|---|---|---|
| Primary Features | P_max Amplitude | Maximum amplitude of the peak |
| | P_average Amplitude | Average current of the peak |
| | P_top Average | Average of the peak above half maximum |
| | P_peakWidth | Full width at half maximum |
| | P_roughness | Standard deviation of the peak above half maximum height |
| | P_frequency | Number of peaks per millisecond over a window of 4096 |
| | C_peaksInCluster | Number of peaks in the cluster |
| | C_frequency | Number of peaks in cluster divided by millisecond length of cluster |
| | C_average Amplitude | Average amplitude of all cluster peaks |
| | C_top Average | Average amplitude of all peaks above half maximum |
| | C_cluster Width | Cluster time length in millisecond |
| | C_roughness | Standard deviation of whole cluster signal |
| | C_max Amplitude | Average of the max of all the peaks in cluster |
| Secondary Features | P_totalPower | Square root of the sum of power spectrum |
| | P_iFFTLow | Average of the first three frequency bands |
| | P_iFFTMedium | Average of the middle three frequency bands |
| | P_iFFTHigh | Average of the highest three frequency bands |
| | P_peakFFT1~10 | Downsampled FFT spectrum |
| | P_highLow_Ratio | Ratio of P_iFFTLow to P_iFFTHigh |
| | P_Odd_FFT | Sum of all odd frequencies from the non-downsampled FFT |

TABLE 6-continued

| Feature Name | Feature Description |
| --- | --- |
| P_Even_FFT | Sum of all even frequencies from the non-downsampled FFT |
| P_OddEvenRatio | Ratio of the odd to the even FFT sums |
| P_peakFFT_Whole1~51 | Downsampled FFT spectrum into various bandwidths. (Lower frequency range, smaller bandwidth size) |
| C_totalPower | Square root of the sum of the power spectrum |
| C_iFFTLow | Average of the first three frequency bands |
| C_iFFTMedium | Average of the middle three frequency bands |
| C_iFFTHigh | Average of the highest three frequency bands |
| C_clusterFFT1~61 | Downsampled FFT spectrum of cluster |
| C_highLow | Ratio of the odd to the even FFT sums of cluster |
| C_freq_Maximum_Peak1~4 | Frequency of the four dominant peaks in the spectrum, ordered by the height of the peaks |
| C_clusterCepstrum1~61 | Spectrum of the power spectrum of the cluster, downsampled to 61 points |
| C_clusterFFT Whole1~51 | Downsampled FFT spectrum into various bandwidths. (Lower frequency range, smaller bandwidth size) |

Figures 9A, 9B, 9C:
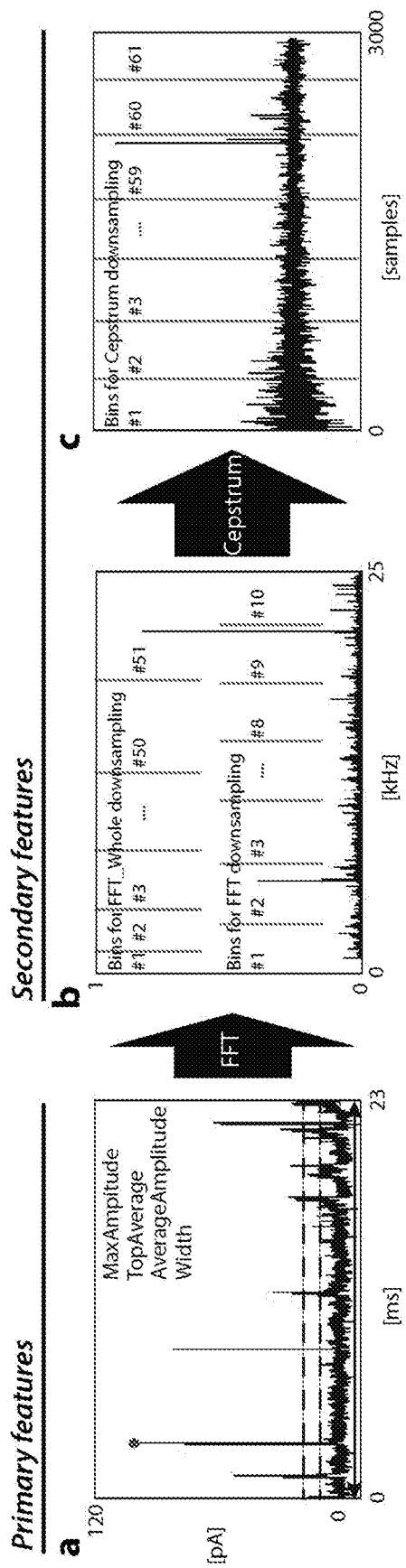
FIG. 9A-FIG. 9C show analysis of RT raw data.

Spikes and clusters in a RT spectrum were Fourier transformed into a 25 kHz window that is the Nyquist frequency of amplifier, and then the whole frequency range was downsampled to small windows. As shown in FIG. 9B, peakFFT and clusterFFT denote features that have the same sampling window size (marked in red), and peakFFT_Whole and clusterFFT_Whole denote features with varied window size (marked in green), of which those with lower frequencies have smaller sampling window sizes (only six windows are shown for the simplicity in the figure). Furthermore, logarithm of the Fourier transformed spectrum was subjected to the inverse Fourier transform, which generated a new spectrum, referred to as cepstrum (FIG. 9C). The cepstrum was also down sampled into the even size of windows for sampling. Once all the features were determined, they were normalized and scaled to make standard deviation to 1. In this way, features of large numeric values were prevented from dominating those that have small numeric values.

5.4.3 Feature Selection

Randomly selected 10% data were used to construct support vectors (hyper plane to separate analyte data points) to train the SVM, and then tested the rest 90% of data to determine the calling accuracy for each DNA nucleotide. There are totally 264 features in Table 6. Some of them are strongly correlated with one another so they were removed through the normalized correlation calculation between feature pairs with coefficient larger than 0.7. A feature variation between the repeated experiments and different analytes are calculated by comparing histograms of a feature in a single measurement with the accumulated measurements. The difference between the repeated runs histogram and the accumulated histogram of an analyte is assigned as 'in-group' fluctuation (variation of the repeats). The difference of a feature between the normalized histogram of a pairs of analytes is 'out-group' fluctuation (variation of the analytes). The features were ranked by the ratio between the in-group fluctuation and the out-group fluctuation, and the low ranked features were dropped. The survived features were further optimized to get the maximum true positive accuracy.

5.4.4 SVM Analysis

The kernel-mode SVM available from the world wide web (www) at github.com/vjethava/svm-theta was used. The SVM running parameters C and gamma were optimized through cross-validation of randomly selected sub data set. Full details of the SVM (written in Matlab) can be found on the world wide web (www) at github.com/ochensati/SVM_DNA_TunnelVision.

5.5 RT of AP

RT spectra of AP were collected in the same way as we collected those of the DNA nucleotides. A solution (100 µM) of AP (purchased from Sigma Aldrich) was prepared in phosphate buffer, pH 7.4. The RT measurements with Py were carried out at a set point of 2 pA current and 500 mV probe bias, and those with Iz at a set-point of 4 pA current and 500 mV probe bias, always following a clean baseline achieved with pure phosphate buffer.

While RT signals were generated with Iz and four sets of data were recorded for SVM analysis, no AP signal was obtained from the RT experiments with Py as expected. The SVM could not separate the AP signals from those of DNA nucleotides generated by Iz. However, the AP signals appear to be much different from the DNA nucleotide signals generated with Py. As a result, all five analytes (dAMP, dCMP, dGMP, dTMP & AP) were classified with high accuracy (Table 7).

TABLE 7

| | dAMP (Py) | dCMP (Py) | dGMP (Py) | dTMP (Py) | AP (Iz) | Average |
| --- | --- | --- | --- | --- | --- | --- |
| Accuracy | 98.4 | 98.7 | 97.9 | 97.0 | 97.2 | 97.8 |

5.6 Results

It was first determined that at the set point of 4 pA and 0.5 V the tunneling gap functionalized with Iz presented a clean baseline. Under these conditions, the gap distance was estimated to be ~2.4 nm.[35] As expected, Iz produced RT signals (spikes) with all of the analytes we measured (FIG. 11A-FIG. 11F). On changing the set-point to 2 pA and 0.5 V, corresponding to a larger gap size, Iz still read the analytes, but less frequently than at 4 pA (data not shown). In contrast, Py presented a cleaner baseline at 2 pA, 0.5 V than at 4 pA, 0.5 V, and it generated RT signals with all the four naturally occurring DNA nucleoside monophosphates, but not with the AP and sugar molecules (FIG. 11G-FIG. 11L). The results may be best explained as a consequence of the formation of sandwiched structures between pyrenes and DNA bases.[36] Under the same set point of 2 pA and 0.5 V, the Bn control didn't generate any tunneling signals from these nucleotides (FIG. 11M-FIG. 11P). When the tip was functionalized with Bn and the substrate with Py, interestingly, the purine nucleotides dAMP and dGMP gave tunneling signals, but the pyrimidine nucleotides did not (FIG. 11Q-FIG. 11T). This indicates that the stacking interactions in the tunneling gap are driven by the size of reader molecules, given that Bn is smaller than Py in size, but more polar and hydrophobic. These data show that Py can distinguish DNA nucleotides from other species more effectively than Iz.

RT data were typically collected in the time domain. Each spike in RT spectra was characterized by peak height (in picoamps, pA), averaged amplitude (pA)—an average of all individual current points constituting a spike, and peak width (in milliseconds, ms). The distributions of these parameters for DNA nucleotides acquired using both Py and Iz are plotted in histograms along with their fitting curves respectively (FIG. 12A-FIG. 12F, see Example 5.4.1, for details on analysis of RT raw data). These data were well fit into a Log-Normal function (adjusted $R^2$>94%), from which mean, median and sigma (o) of those parameters were derived (Table 5). The results show that the tunnel gap functionalized with Py has a marginally higher tunneling current (9.4 pA) with the DNA nucleotides than the one with Iz (9.0 pA) on average for the four nucleotides although the former had a smaller set-point current (2 pA) than the latter (4 pA), but their averaged heights for both Py and Iz are about same (see FIG. 12A-FIG. 12F and Table 5 for the averaged amplitude). The residence time of peaks for Iz with a mean value of 0.42 ms is distributed among the nucleotides more uniformly than those for Py with a mean value of 0.40 ms (FIG. 12A-FIG. 12F and Table 5), an indication that the hydrogen bonding reader is less discriminatory to the nucleobases than the stacking reader. The most important is that the Py reader resolves the four DNA nucleotides with distinguishable modes (FIG. 12A-FIG. 12F) although significant overlaps remain in the distributions. Also, Py can generate tunneling spikes as frequently as Iz with dAMP, dMP and dGMP, and much more frequently with dTMP than Iz (Table 5). This suggests that the π-π stacking is as efficient as the hydrogen bonding for reading DNA bases. However, none of these parameters alone are sufficient to identify the DNA nucleotides.

Figure 10A:
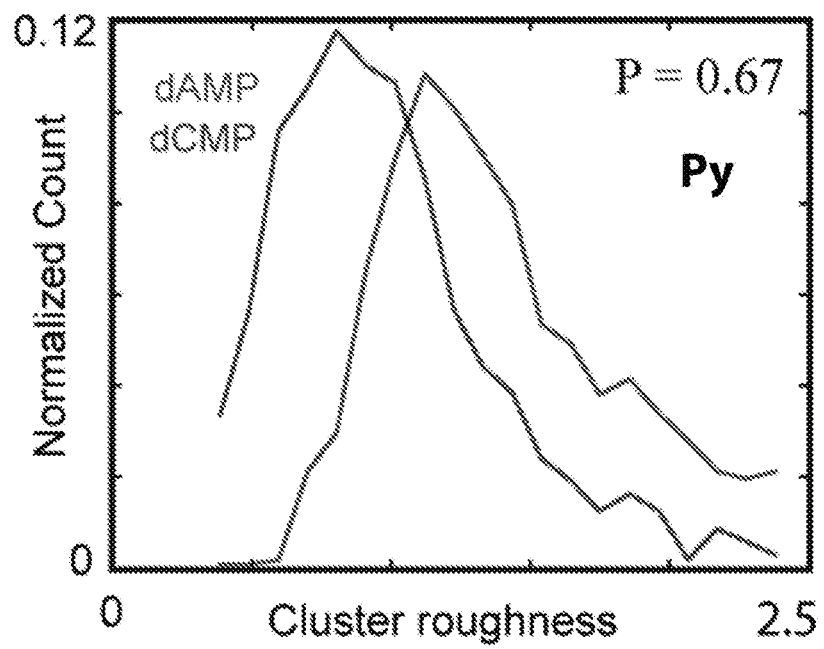
FIG. 10A-FIG. 10X show plots to display distributions of the same feature from two different DNA nucleotides using a single feature data that can only be assigned to one analyte with a probability only marginally above random, or equal to P=0.5 in the most cases.
Figure 10B:
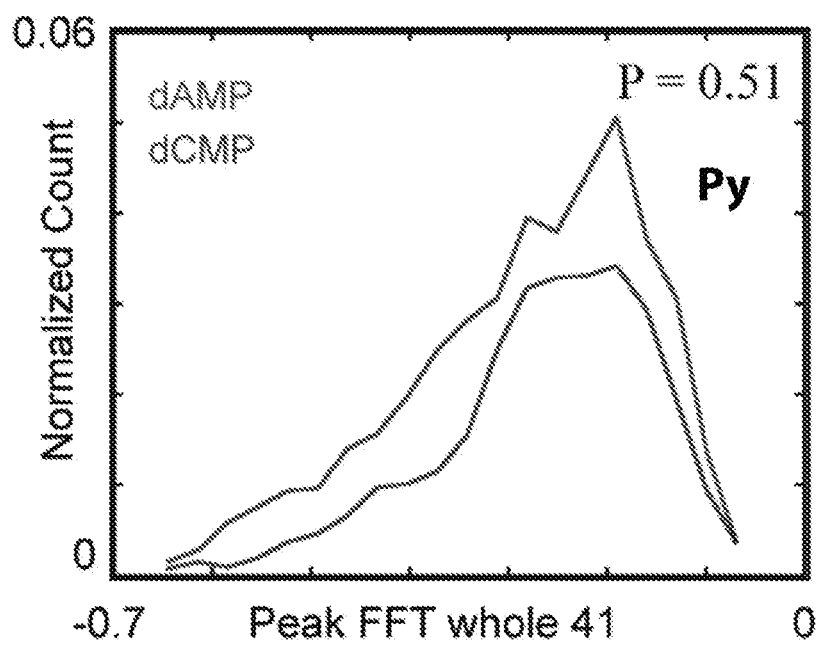
Figure 10C:
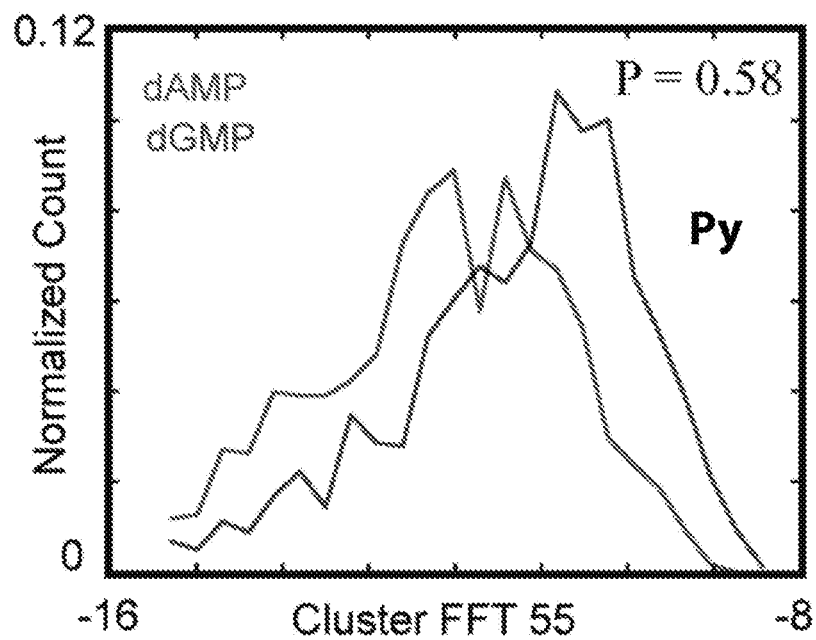
Figure 10D:
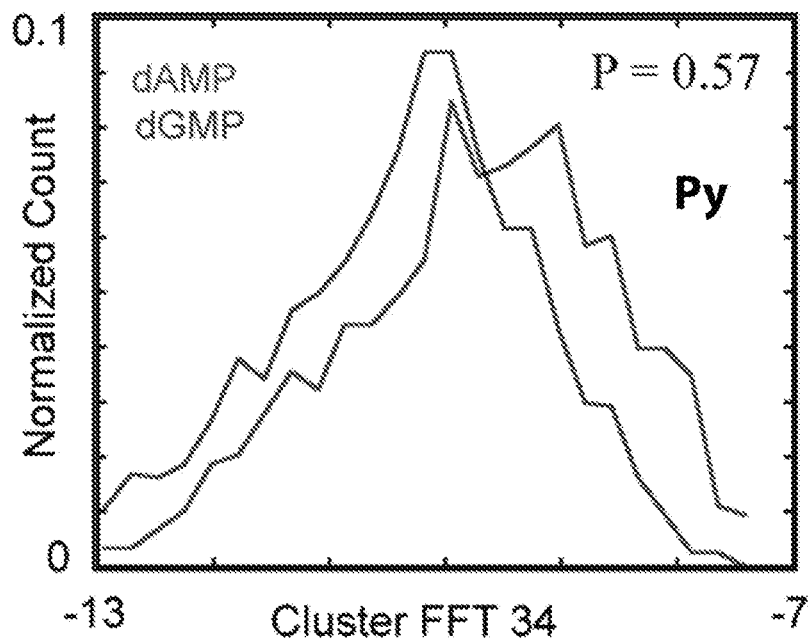
Figure 10E:
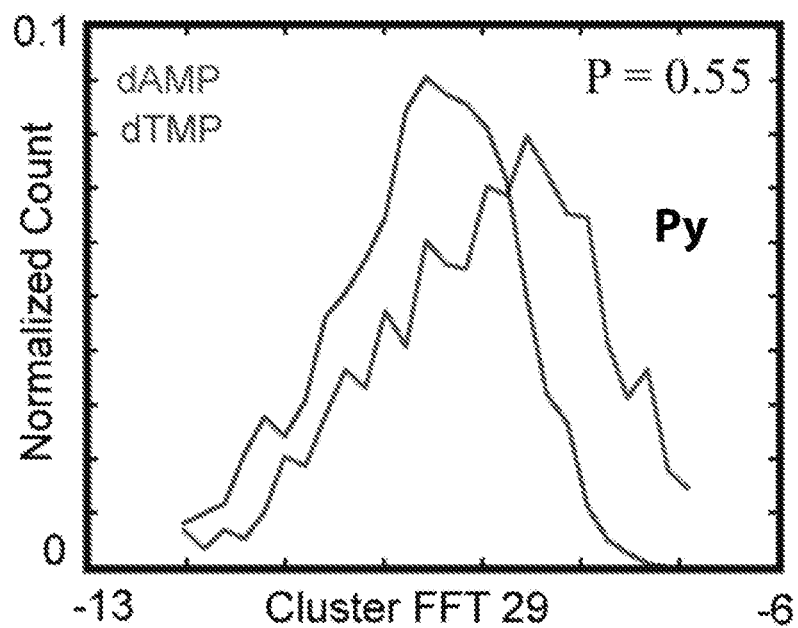
Figure 10F:
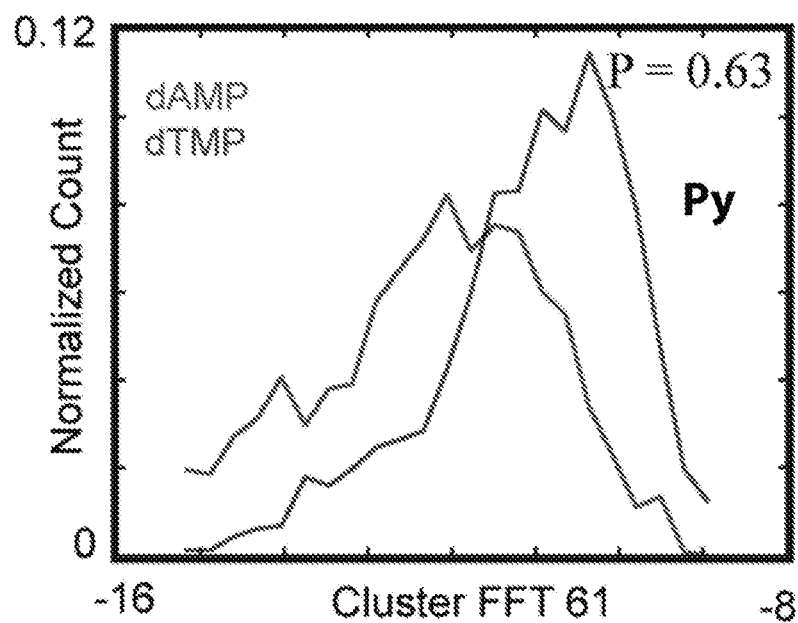
Figure 10G:
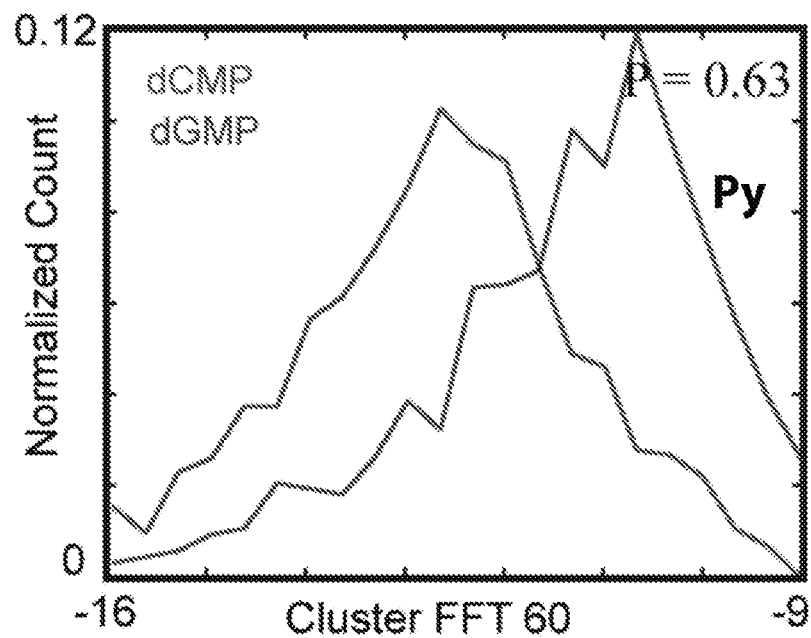
Figure 10H:
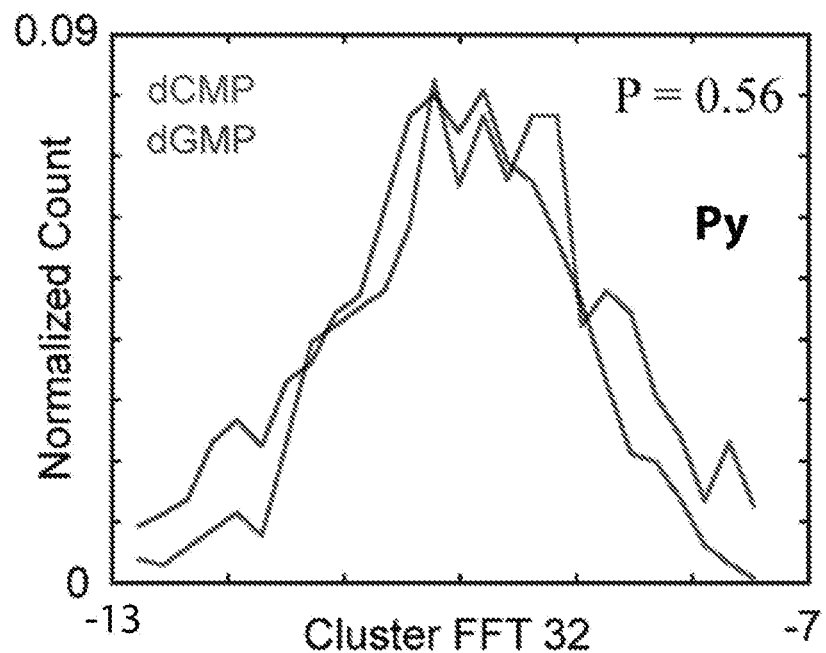
Figure 10I:
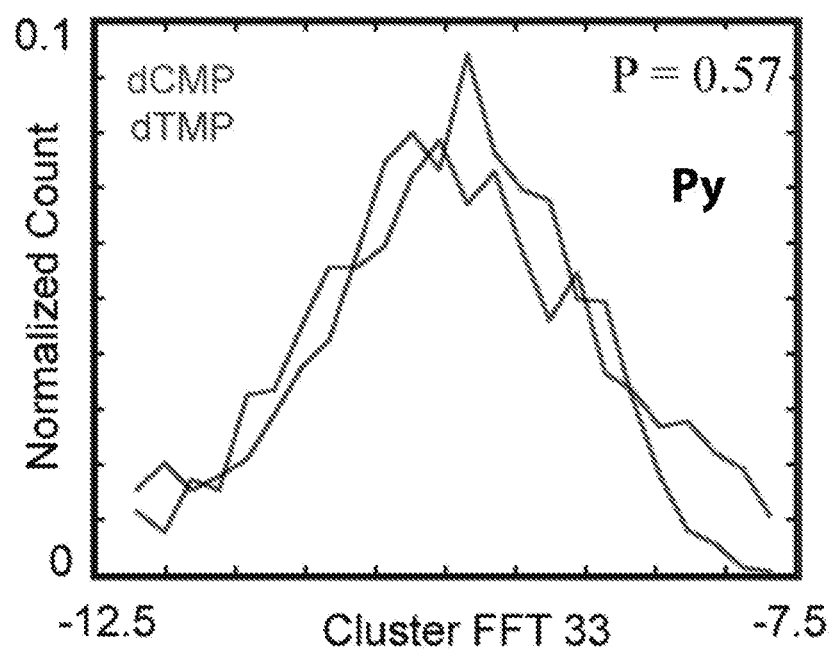
Figure 10J:
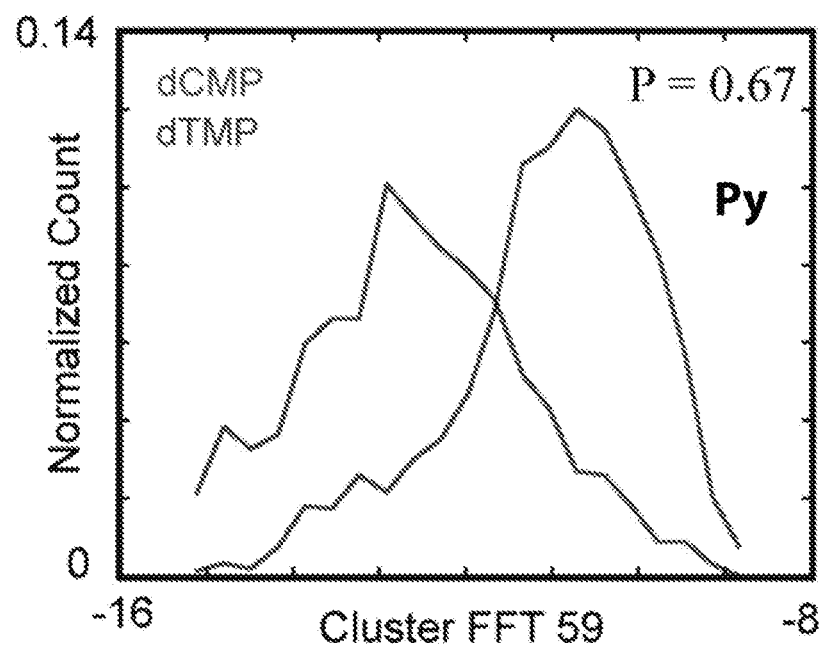
Figure 10K:
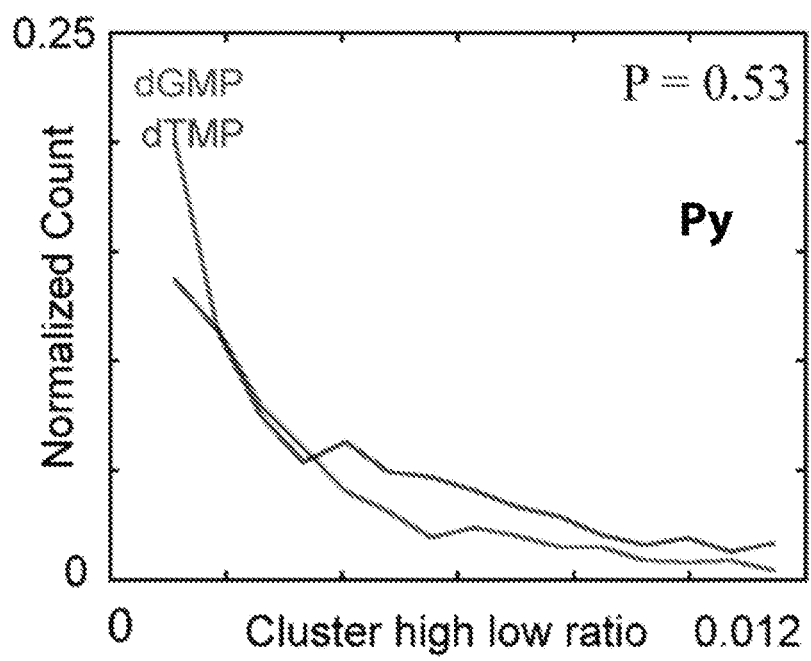
Figure 10L:
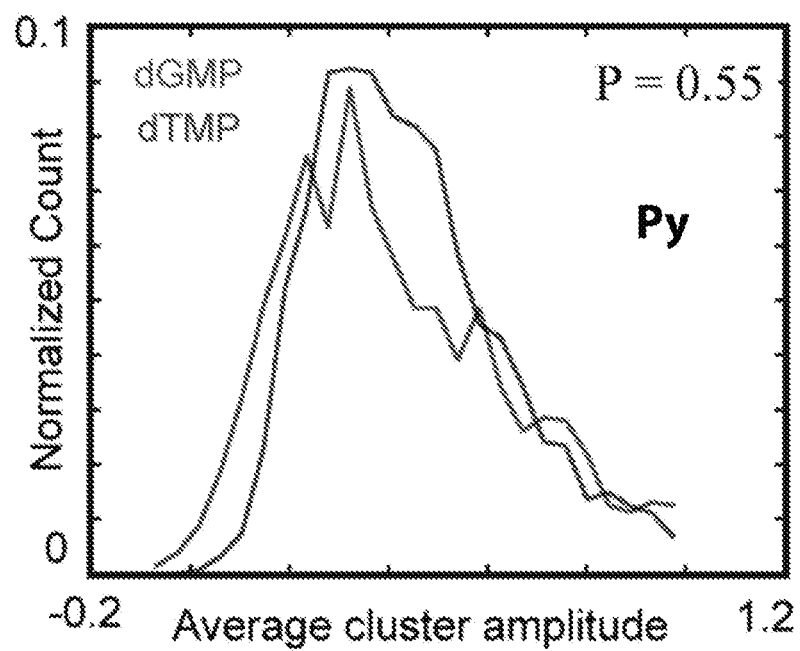
Figure 10M:
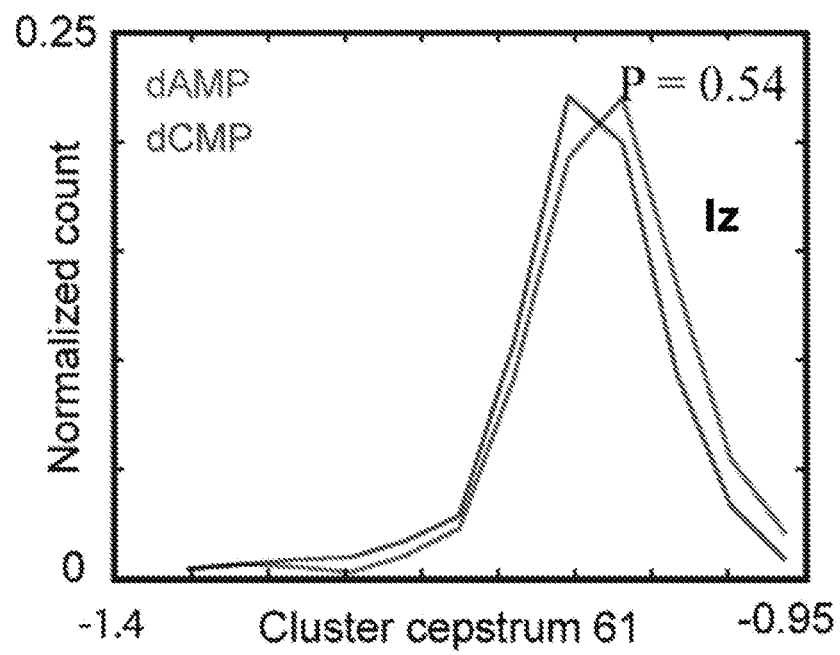
Figure 10N:
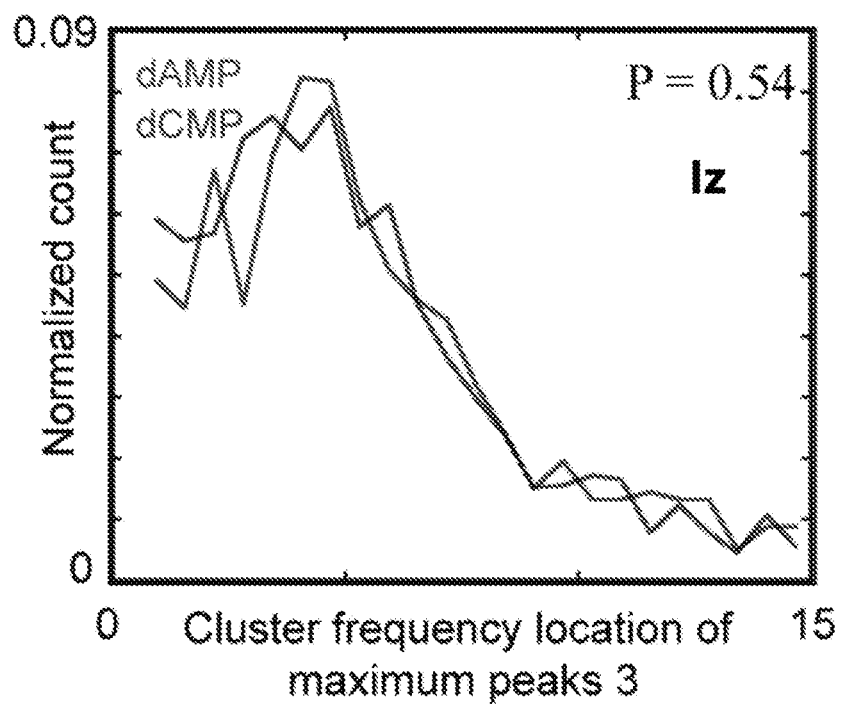
Figure 10O:
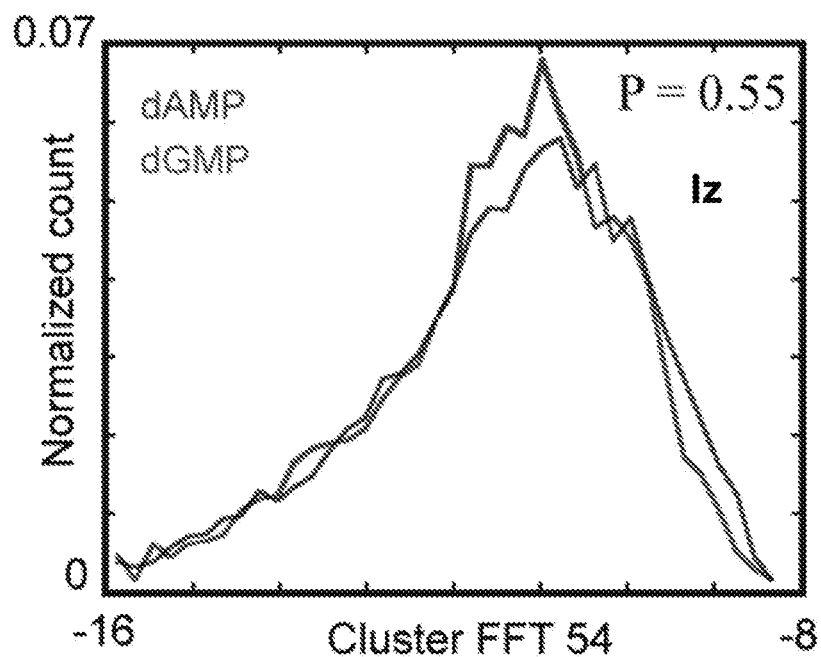
Figure 10P:
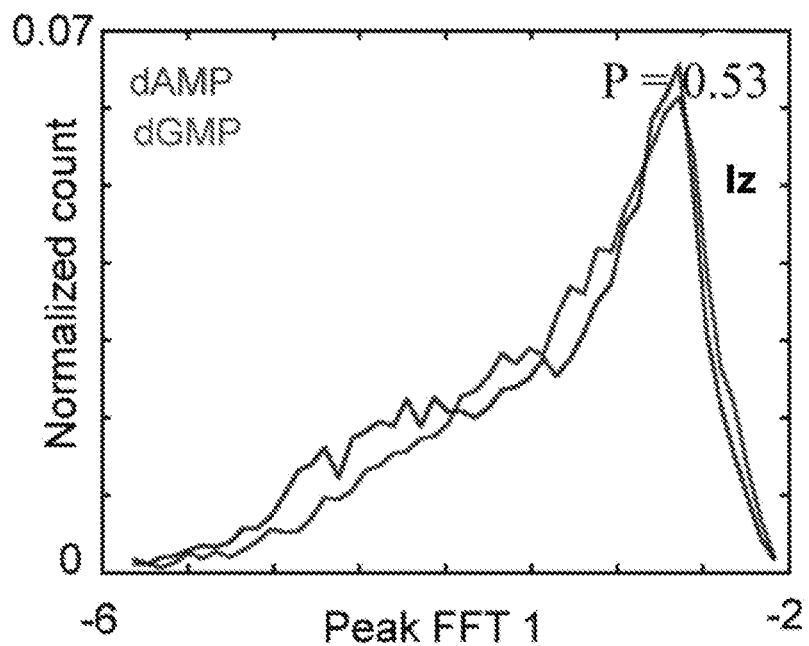
Figure 10Q:
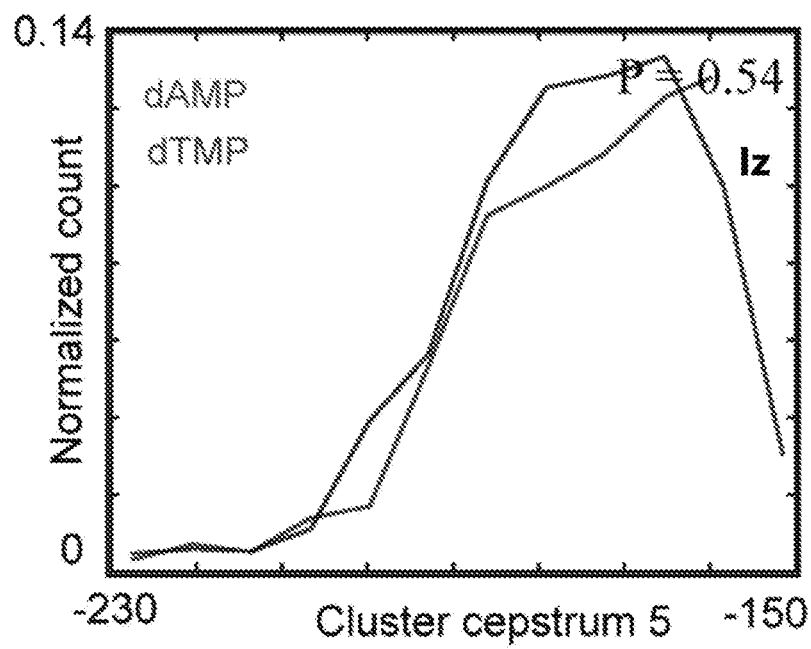
Figure 10R:
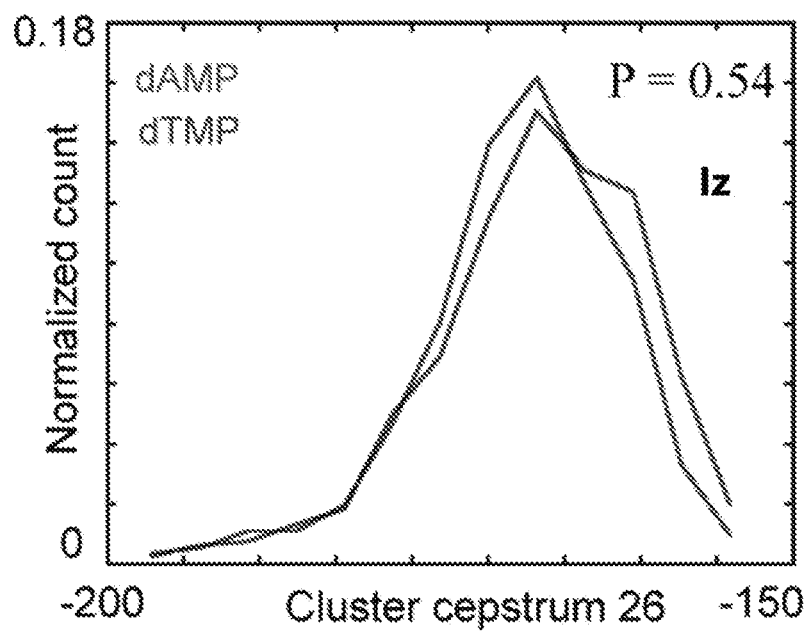
Figure 10S:
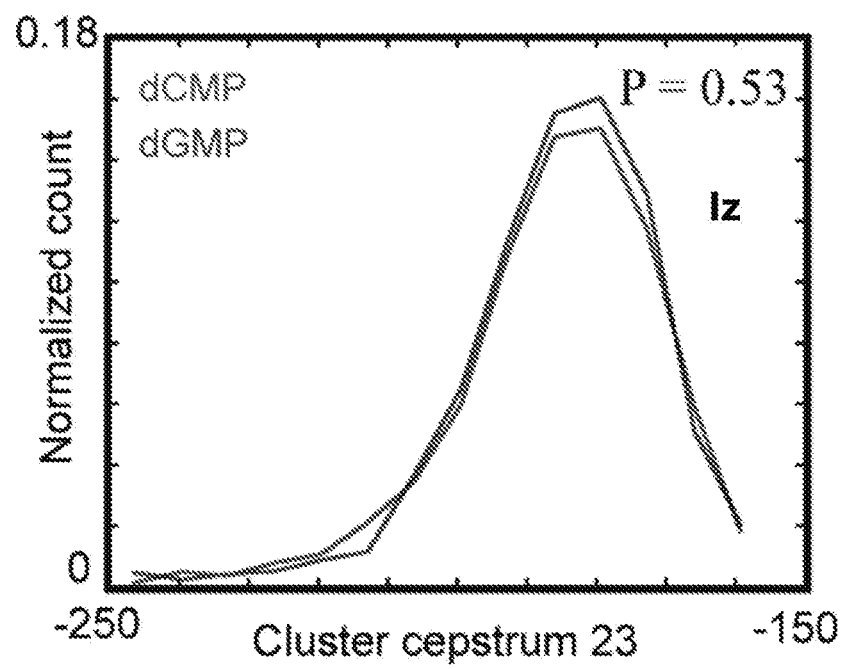
Figure 10T:
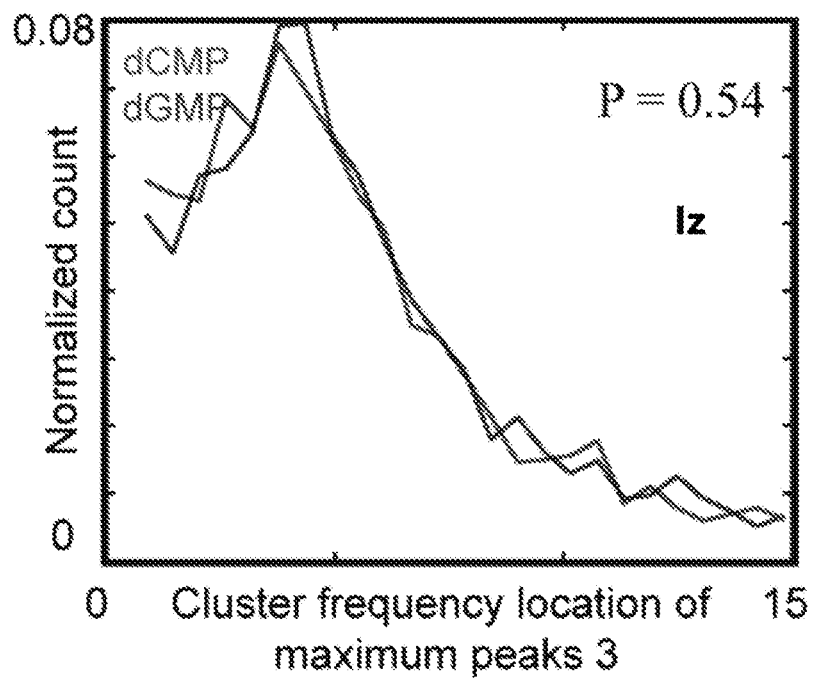
Figure 10U:
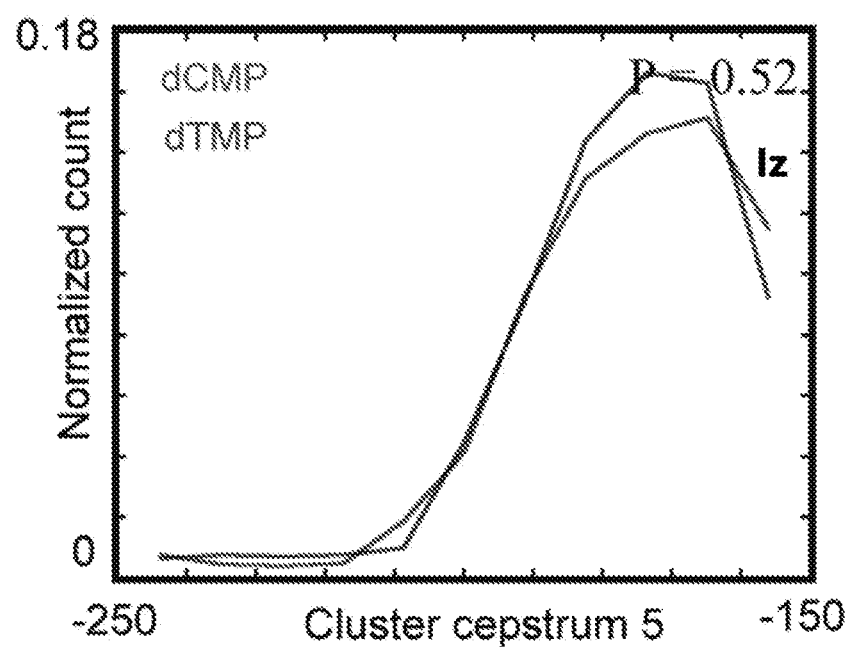
Figure 10V:
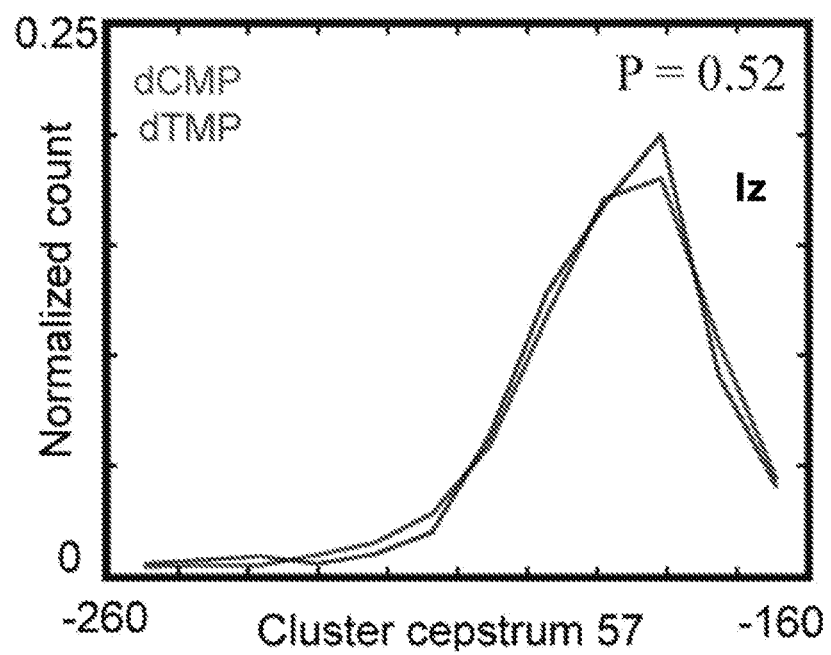
Figure 10W:
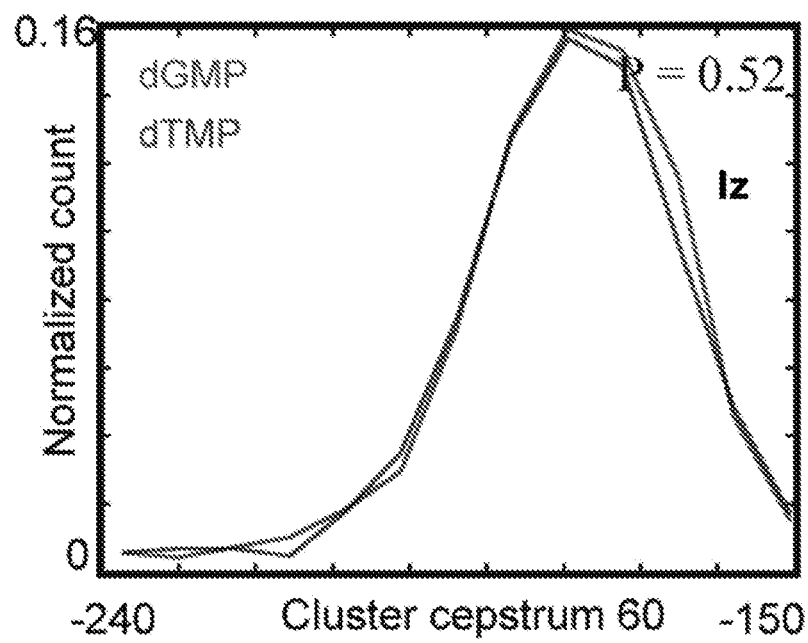
Figure 10X:
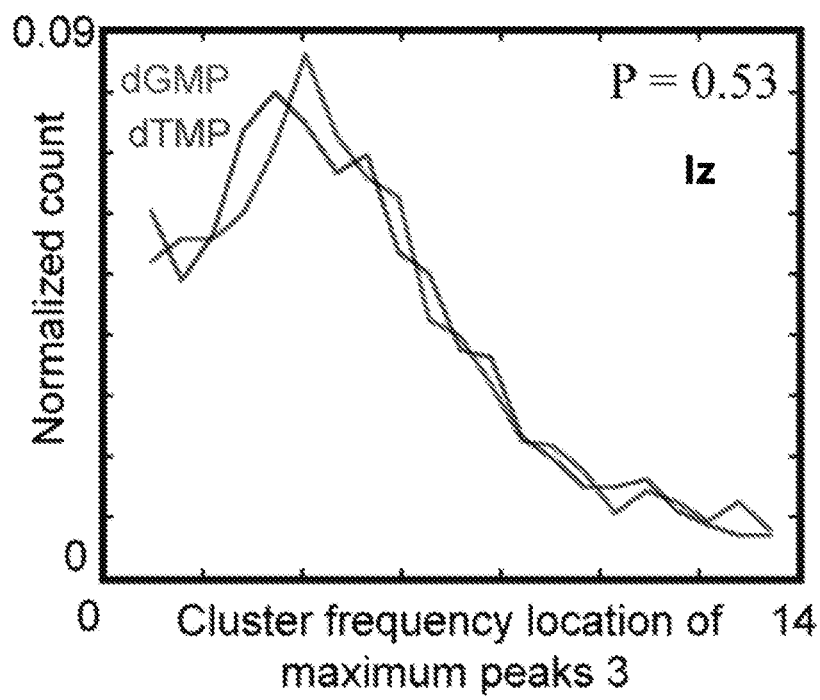
Figure 12A:
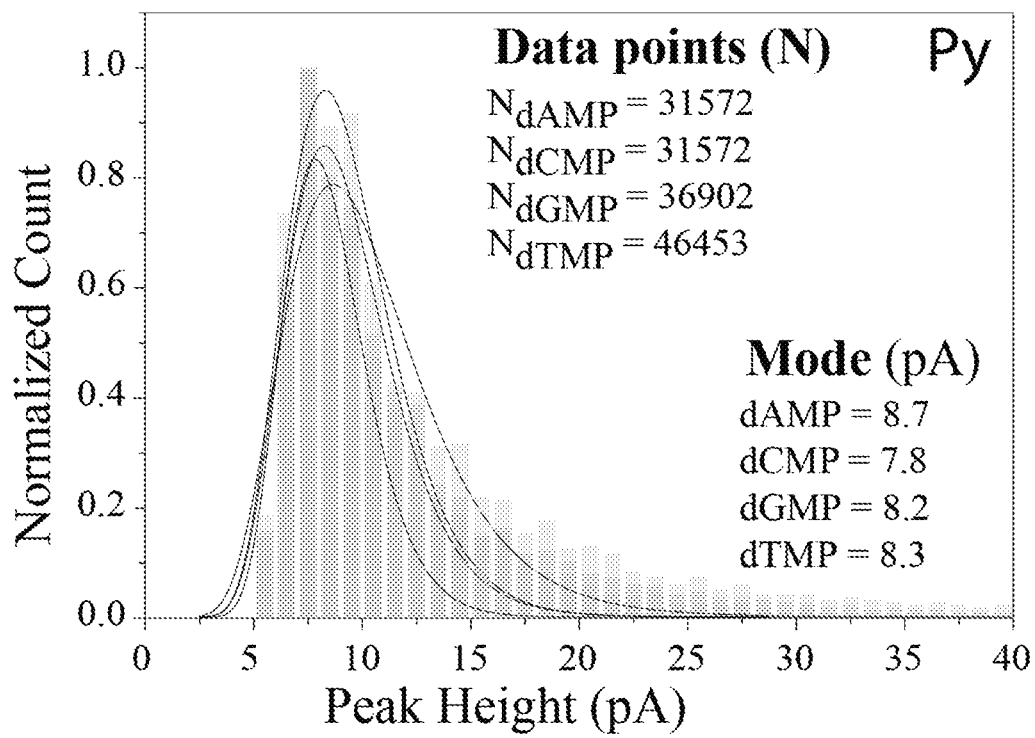
FIG. 12A-FIG. 12F show histograms of peak height (FIG. 12A and FIG. 12D), averaged amplitude (FIG. 12B and FIG. 12E), peak width (FIG. 12C and FIG. 12F), and their fitting curves of current spikes from recognition of DNA nucleotides by Py at the set point of 0.5 V and 2 pA; and by Iz at the set point of 0.5 V and 4 pA.
Figure 12B:
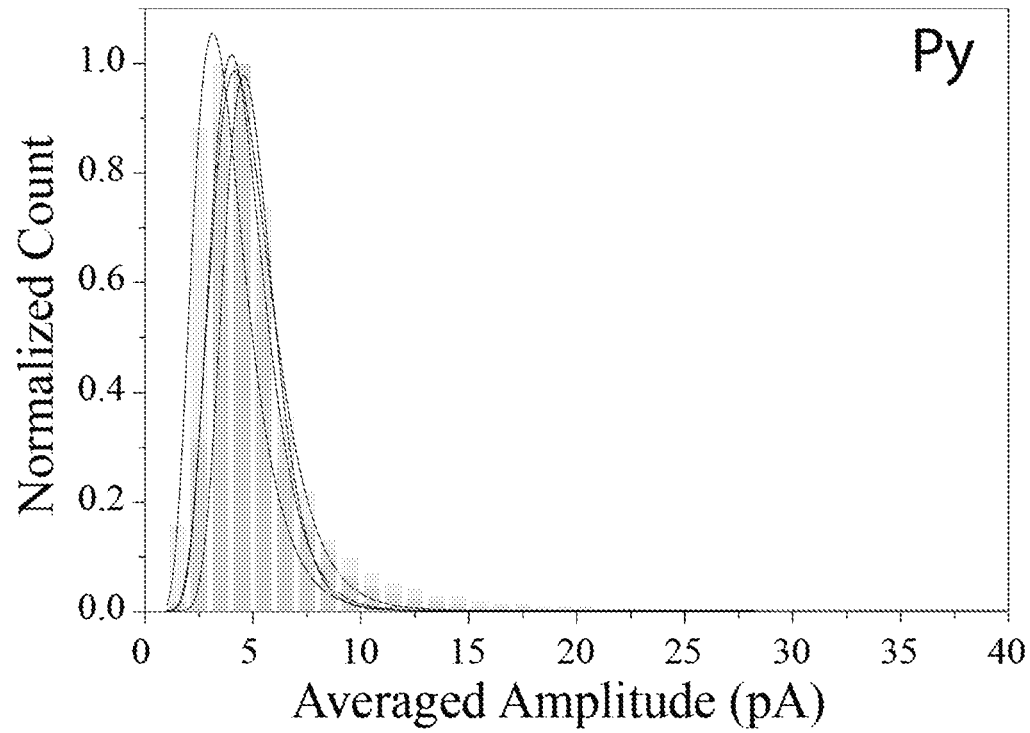
Figure 12C:
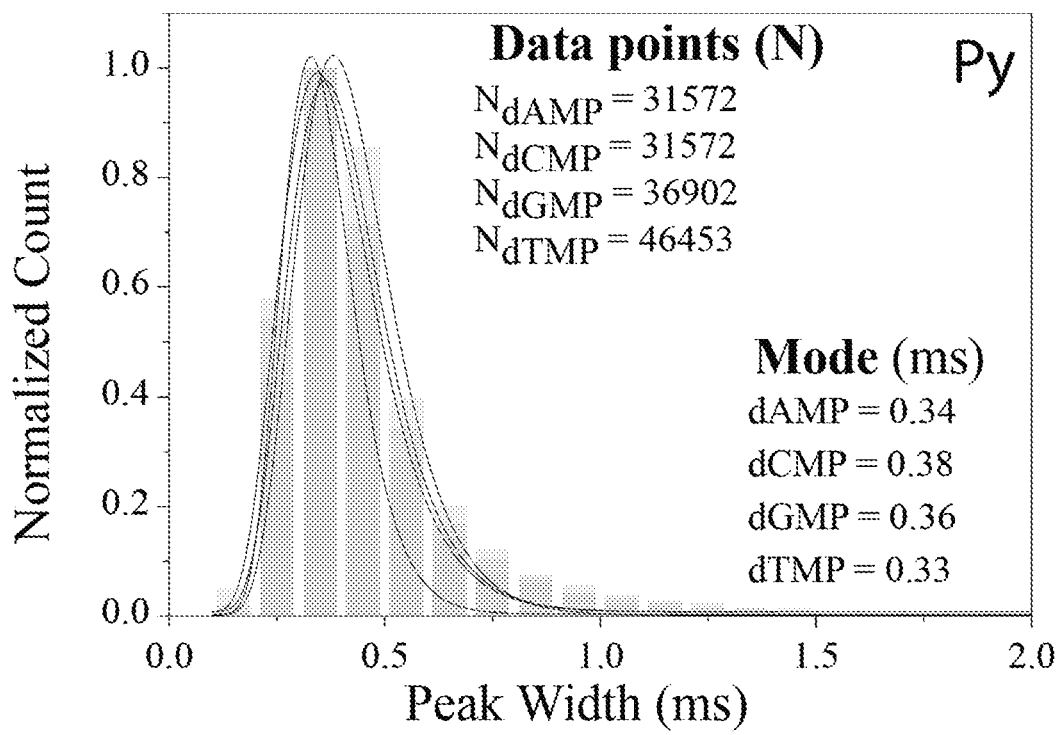
Figure 12D:
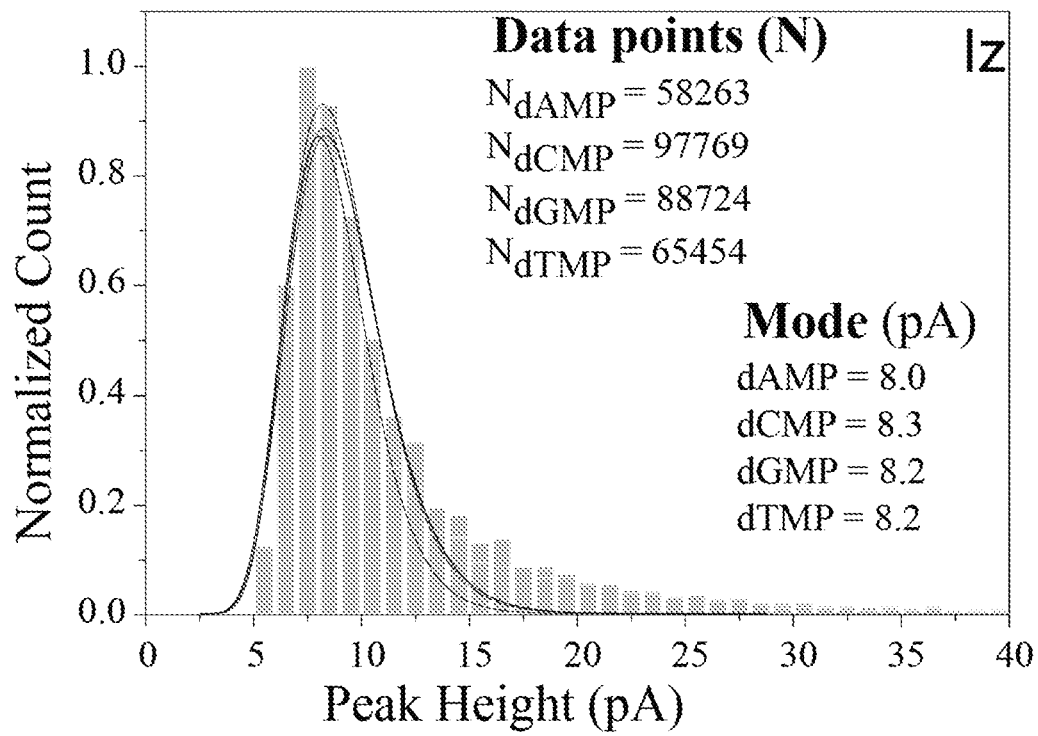
Figure 12E:
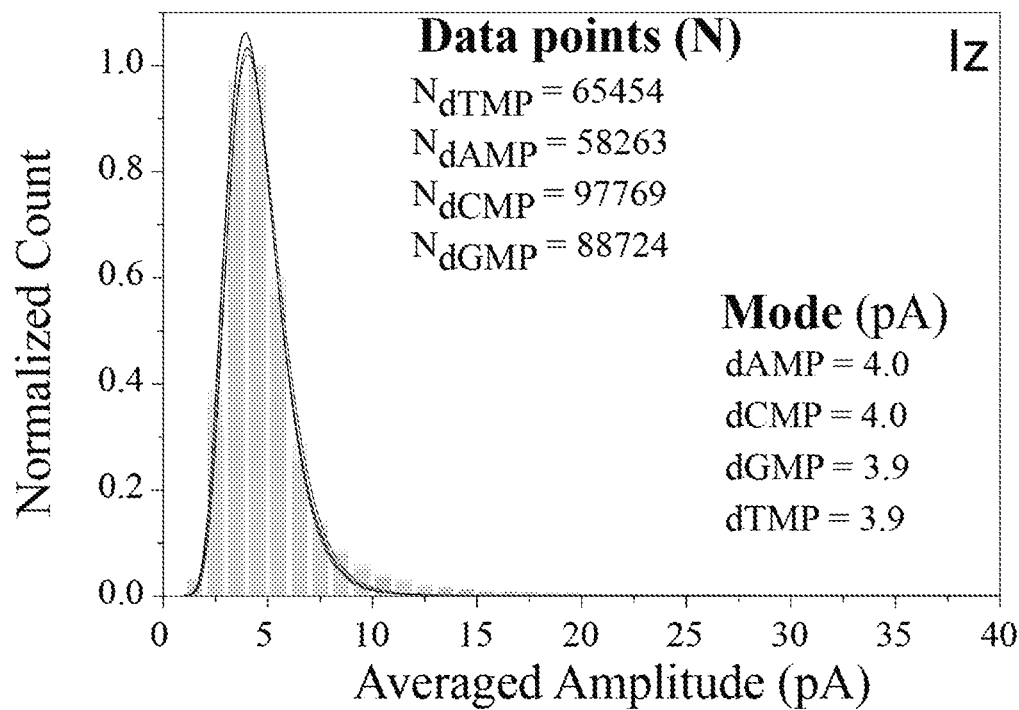
Figure 12F:
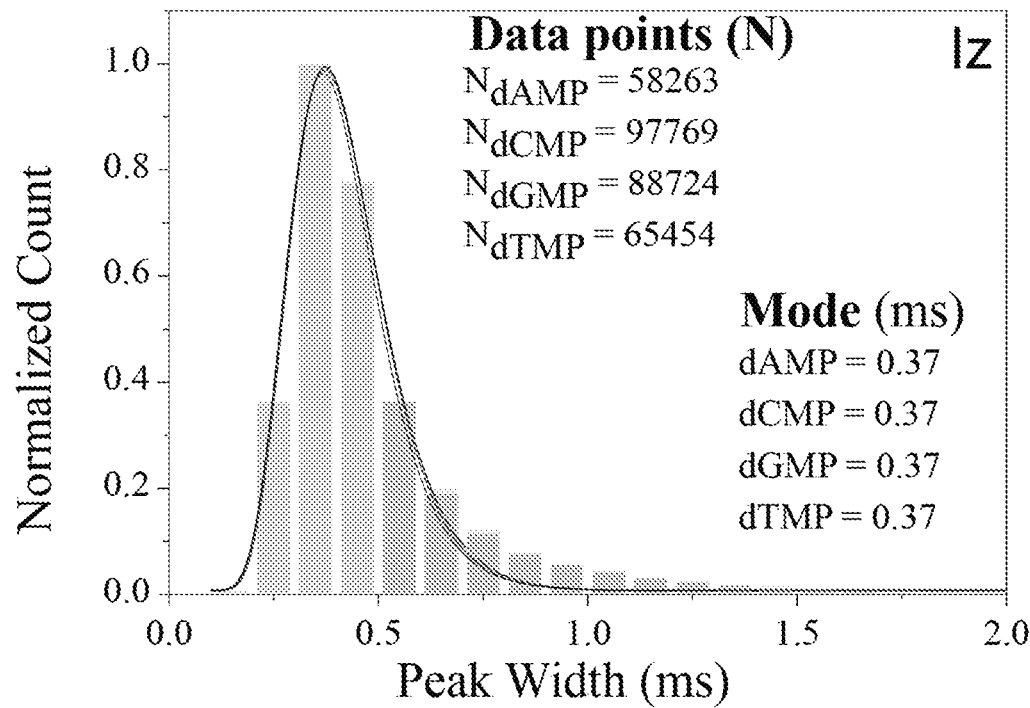

In order to call DNA nucleotides from the tunneling current data, the RT spectra were subjected to Fourier transform and cepstrum conversion (Example 5.4.2 and FIG. 9A-FIG. 9C), which resulted in 264 features (listed in Table 6). As shown in FIG. 10A-FIG. 10X, no single feature has a capability to distinguish two DNA nucleotides from each other. However, the probability that any particular pair of signal feature values occur together is much more effective in separating analytes. A two-dimensional plot of "Peak FFT whole 41" and "Cluster roughness" for dAMP and dCMP can be assigned with 77% accuracy using the pair-wise features (data not shown). While possible combinations of other features have been tested (data not shown), only the two just above mentioned gave the best separation between dAMP and dCMP. It is significantly larger than a random case of no separation with a value of P=0.5 (or 50%). Overall, Py can distinguish well between two analytes in any of six possible pairs consisted of four DNA nucleotides with accuracy of ~82% on average (data not shown). In comparison, Iz can only distiguish between dAMP and dCMP with accuracy of 66% (data not shown), ~10% lower than Py. In the best case, Py can achieve ~89% separation with the two features alone for dCMP and dTMP, whereas Iz can only achieve 70% for the two nucleotides of dAMP and dGMP (data not shown).

As mentioned above, a 2-D plot was used to illustrate a more general and harder to visualize multi-dimensional (≥4D) analysis of feature ensembles to attain much higher accuracy. To do this, a Support Vector Machine (SVM), a machine-learning algorithm, was used to analyze the tunneling data.[22] In brief, the SVM was first trained using a combination of randomly selected 10% subsets of the four data pools generated from the feature extraction for each nucleotide. The process iteratively reduced the 264 available signal features (see Example 5.4.3) to a range of smaller numbers that maintains a 100% separation for the training data (see FIG. 13A and FIG. 13B for training accuracy curves). As a result, the best 94 features were generated for Py and 55 for Iz (listed in Tables 8 and 9) to identify DNA nucleotides in the remaining 90% of the data.

TABLE 8

Independent features of Py for SVM to assign DNA nucleotides

| | |
|---|---|
| 1. | Peak Max Amplitude |
| 2. | Peak Average Amplitude |
| 3. | Peak Top Average |
| 4. | Peak Width |
| 5. | Peak Total Power |
| 6. | Peak FFT 3 |
| 7. | Peak FFT 6 |
| 8. | Peak FFT 7 |
| 9. | Peak FFT 8 |
| 10. | Peak High Low Ratio |
| 11. | Peak FFT Whole 4 |
| 12. | Peak FFT Whole 5 |
| 13. | Peak FFT Whole 6 |
| 14. | Peak FFT Whole 7 |
| 15. | Peak FFT Whole 8 |
| 16. | Peak FFT Whole 9 |
| 17. | Peak FFT Whole 48 |
| 18. | Peak FFT Whole 49 |
| 19. | Cluster Average Amplitude |
| 20. | Cluster Roughness |
| 21. | Cluster Total Power |
| 22. | Cluster FFT Low |
| 23. | Cluster FFT High |
| 24. | Cluster FFT 1 |
| 25. | Cluster FFT 2 |
| 26. | Cluster FFT 3 |
| 27. | Cluster FFT 11 |
| 28. | Cluster FFT 12 |
| 29. | Cluster FFT 13 |
| 30. | Cluster FFT 14 |
| 31. | Cluster FFT 15 |
| 32. | Cluster FFT 16 |
| 33. | Cluster FFT 17 |
| 34. | Cluster FFT 18 |
| 35. | Cluster FFT 23 |
| 36. | Cluster FFT 25 |
| 37. | Cluster FFT 26 |
| 38. | Cluster FFT 27 |
| 39. | Cluster FFT 28 |
| 40. | Cluster FFT 29 |
| 41. | Cluster FFT 30 |
| 42. | Cluster FFT 31 |
| 43. | Cluster FFT 32 |
| 44. | Cluster FFT 38 |
| 45. | Cluster FFT 39 |
| 46. | Cluster FFT 40 |
| 47. | Cluster FFT 41 |
| 48. | Cluster FFT 42 |
| 49. | Cluster FFT 43 |
| 50. | Cluster FFT 44 |
| 51. | Cluster FFT 47 |
| 52. | Cluster FFT 48 |
| 53. | Cluster FFT 49 |
| 54. | Cluster FFT 50 |
| 55. | Cluster FFT 51 |
| 56. | Cluster FFT 52 |
| 57. | Cluster FFT 53 |
| 58. | Cluster FFT 54 |
| 59. | Cluster FFT 55 |
| 60. | Cluster FFT 56 |
| 61. | Cluster FFT 57 |
| 62. | Cluster FFT 58 |
| 63. | Cluster FFT 59 |

TABLE 8-continued

Independent features of Py for SVM to assign DNA nucleotides

| | |
|---|---|
| 64. | Cluster FFT 60 |
| 65. | Cluster FFT 61 |
| 66. | Cluster High Low |
| 67. | Cluster Freq. Maximum Peaks 1 |
| 68. | Cluster Freq. Maximum Peaks 2 |
| 69. | Cluster FFT Whole 1 |
| 70. | Cluster FFT Whole 16 |
| 71. | Cluster FFT Whole 17 |
| 72. | Cluster FFT Whole 18 |
| 73. | Cluster FFT Whole 19 |
| 74. | Cluster FFT Whole 20 |
| 75. | Cluster FFT Whole 21 |
| 76. | Cluster FFT Whole 22 |
| 77. | Cluster FFT Whole 23 |
| 78. | Cluster FFT Whole 24 |
| 79. | Cluster FFT Whole 30 |
| 80. | Cluster FFT Whole 31 |
| 81. | Cluster FFT Whole 32 |
| 82. | Cluster FFT Whole 33 |
| 83. | Cluster FFT Whole 34 |
| 84.. | Cluster FFT Whole 35 |
| 85. | Cluster FFT Whole 36 |
| 86. | Cluster FFT Whole 37 |
| 87. | Cluster FFT Whole 38 |
| 88. | Cluster FFT Whole 39 |
| 89. | Cluster FFT Whole 40 |
| 90. | Cluster FFT Whole 41 |
| 91. | Cluster FFT Whole 42 |
| 92. | Cluster FFT Whole 47 |
| 93. | Cluster FFT Whole 48 |
| 94. | Cluster FFT Whole 49 |

TABLE 9

Independent features of Iz for SVM to assign DNA nucleotides

| | |
|---|---|
| 1. | Peak Odd Even Ratio |
| 2. | Cluster Average Amplitude |
| 3. | Cluster Top Average |
| 4. | Cluster Cepstrum 3 |
| 5. | Cluster Cepstrum 4 |
| 6. | Cluster Cepstrum 5 |
| 7. | Cluster Cepstrum 6 |
| 8. | Cluster Cepstrum 7 |
| 9. | Cluster Cepstrum 8 |
| 10. | Cluster Cepstrum 9 |
| 11. | Cluster Cepstrum 10 |
| 12. | Cluster Cepstrum 11 |
| 13. | Cluster Cepstrum 12 |
| 14. | Cluster Cepstrum 13 |
| 15. | Cluster Cepstrum 14 |
| 16. | Cluster Cepstrum 15 |
| 17. | Cluster Cepstrum 16 |
| 18. | Cluster Cepstrum 17 |
| 19. | Cluster Cepstrum 18 |
| 20. | Cluster Cepstrum 19 |
| 21. | Cluster Cepstrum 20 |
| 22. | Cluster Cepstrum 21 |
| 23. | Cluster Cepstrum 22 |
| 24. | Cluster Cepstrum 23 |
| 25. | Cluster Cepstrum 24 |
| 26. | Cluster Cepstrum 25 |
| 27. | Cluster Cepstrum 26 |
| 28. | Cluster Cepstrum 27 |
| 29. | Cluster Cepstrum 28 |
| 30. | Cluster Cepstrum 29 |
| 31. | Cluster Cepstrum 30 |
| 32. | Cluster Cepstrum 31 |
| 33. | Cluster Cepstrum 32 |
| 34. | Cluster Cepstrum 33 |
| 35. | Cluster Cepstrum 34 |
| 36. | Cluster Cepstrum 35 |
| 37. | Cluster Cepstrum 36 |
| 38. | Cluster Cepstrum 37 |
| 39. | Cluster Cepstrum 38 |
| 40. | Cluster Cepstrum 39 |
| 41. | Cluster Cepstrum 40 |
| 42. | Cluster Cepstrum 41 |
| 43. | Cluster Cepstrum 42 |
| 44. | Cluster Cepstrum 43 |
| 45. | Cluster Cepstrum 44 |
| 46. | Cluster Cepstrum 45 |
| 47. | Cluster Cepstrum 46 |
| 48. | Cluster Cepstrum 47 |
| 49. | Cluster Cepstrum 49 |
| 50. | Cluster Cepstrum 52 |
| 51. | Cluster Cepstrum 53 |
| 52. | Cluster Cepstrum 54 |
| 53. | Cluster Cepstrum 55 |
| 54. | Cluster Cepstrum 56 |
| 55. | Cluster Cepstrum 58 |

Figure 13A:
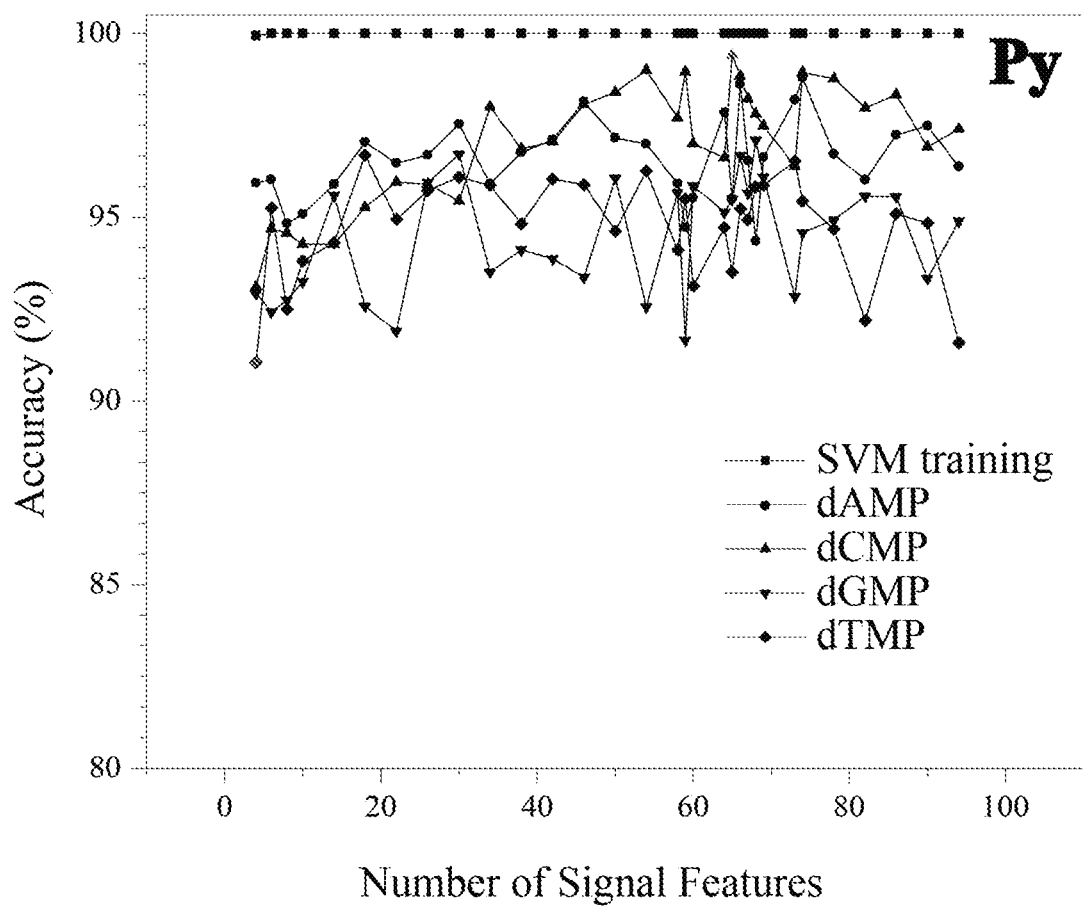
FIG. 13A and FIG. 13B show a plot for nucleotide calling accuracy vs number of used signal features with Py (FIG. 13A) and with Iz (FIG. 13B).
Figure 13B:
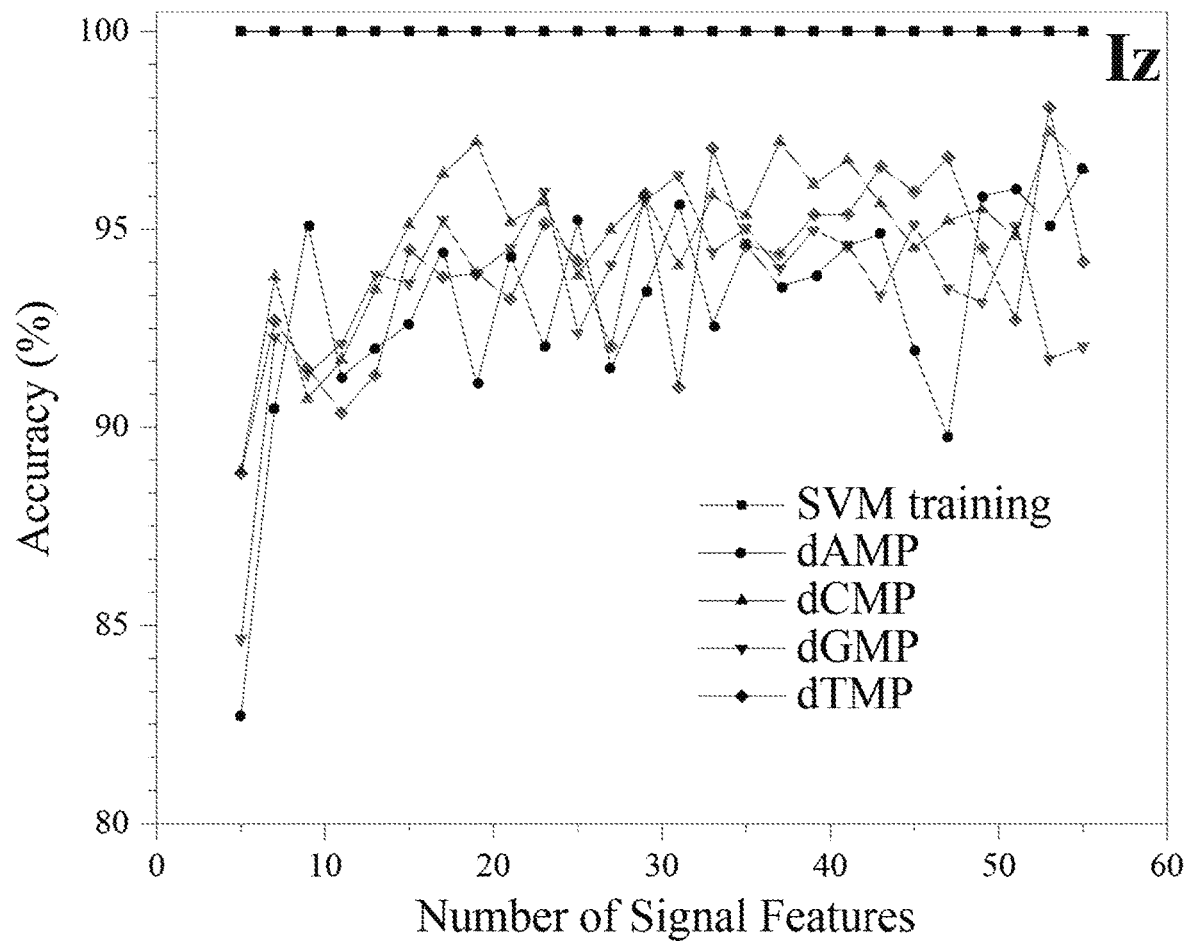

The SVM first removed those signals common to all the data obtained from different samples owing to contamination, capture events that were insensitive to chemical variation and noise spikes generated by the STM electronics and servo control, which amounted to about 30% of signal spikes, and then assigned the remaining signals to individual DNA nucleotides with the trained features (see Example 5.4.4). Such a method of training on a subset of all four data sets (collected with four microscopically-different tunnel junctions) sets an upper limit on accuracy (called the "optimistic" accuracy) of identifying an analyte. Practically, it can be achieved by calibrating the RT device with a standard solution prior to testing the real sample. As shown in FIG. 13A and FIG. 13B, the final accuracies fluctuate, depending on different combinations of those features. Table 10 lists the highest optimistic accuracy achieved by the SVM for identifying each individual DNA nucleotide in the plot.

TABLE 10

The accuracy (%) of both Py and Iz achieved in determining individual DNA nucleotides by RT

| | | dAMP | dCMP | dGMP | dTMP | Mean ± σ |
|---|---|---|---|---|---|---|
| Py | Optimistic | 98.8 | 99.4 | 97.1 | 96.7 | 98.0 ± 1.3 |
| | Predictive | 76.3 | 89.0 | 93.4 | 83.6 | 85.6 ± 7.4 |
| Iz | Optimistic | 96.5 | 97.4 | 96.4 | 98.1 | 97.1 ± 0.8 |
| | Predictive | 94.6 | 75.3 | 40.3 | 44.1 | 63.6 ± 26.0 |

With the Py reader, the four DNA nucleotides can be identified with accuracies ranging from 99.4% to 96.7, on average 98.0%, whereas Iz can read the DNA nucleotides with accuracy from 98.1% to 96.4, on average 97.1%. There is a ~1% improvement to the optimistic accuracy from Iz to Py. Importantly, even a 0.1% improvement to accuracy is of great significance for sequencing of large genomes such as the human genome especially when the focus is on cancer mutations. This is because misidentification of 1 out of 1,000 nucleotides would result in about 3,000,000 false calls over a human genome that is composed of ~3 billion of base pairs. It is challenging to confirm a single nucleotide variant (SNV) generated by NGS either owing to a true biological variant or a technical error.[3, 37] The RT technology directly reads DNA bases from their intrinsic properties, providing a method to reduce the uncertainties in detection of SNVs.

More interesting is the "predictive" accuracy, which was generated by training the SVM on data from three tunnel junctions and then using it to analyze data from the fourth junction. Py can read the four DNA nucleotides with its predictive accuracies ranging from 76% to 93%, on average of ~86%, whereas Iz from 40% to 95%, on average of ~64% with a much larger standard deviation (Table 10). These data manifest Py as a better reader molecule than Iz. Although the predictive accuracy of Py is modest, it can be improved by measuring the same sample with multiple times since the RT process is a stochastic. With the predictive capability, RT can be used to identify unknown samples that contain analytes that are already built in a RT database.

Figure 14:
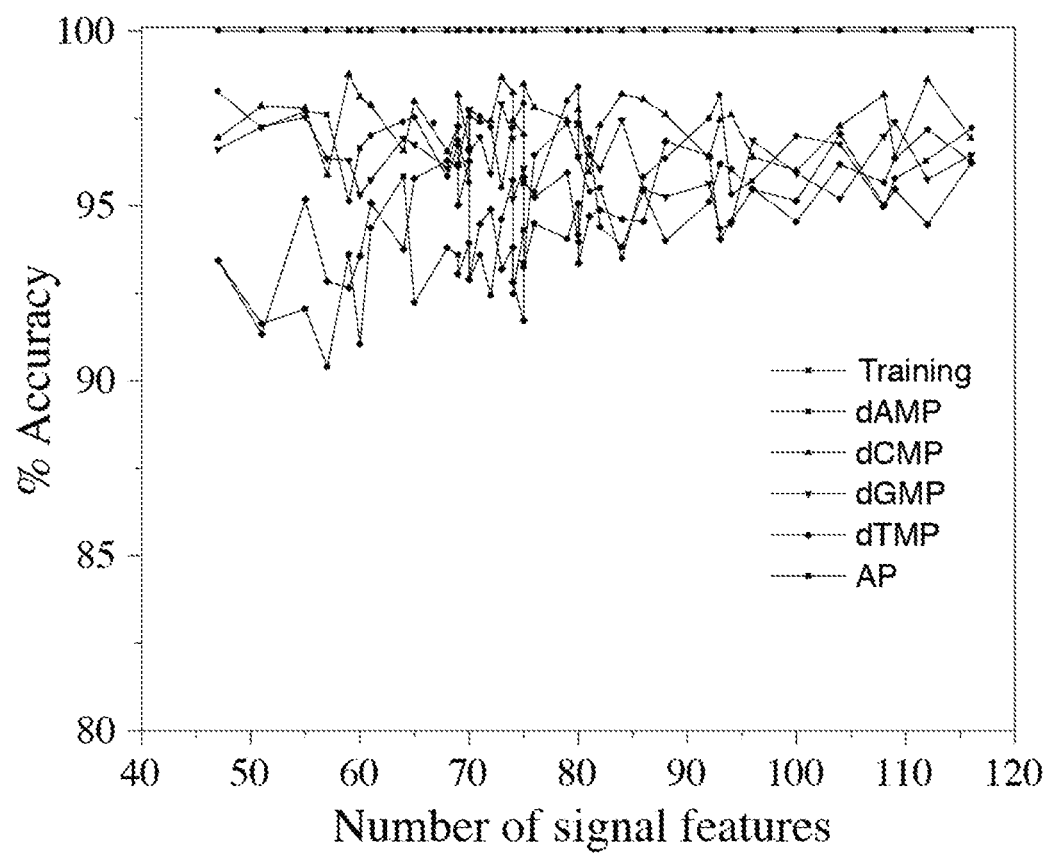
FIG. 14 shows a plot of accuracy determined by SVM analysis of AP (read with Iz) and four DNA nucleotides (read with Py).

In conclusion, π-π stacking interaction can be used to identify DNA bases in the tunnel gap. Compared to Iz, the pyrene reader is not only more specific, but also more accurate to reading those canonical DNA bases. Interestingly, Iz recognizes the abasic site, which may be used to identify the depurination and depyrimidination in genomes when a comparison is run with data generated by Py. Preliminary analysis shows that the RT data of AP can be separated from those of DNA nucleotides generated by Py with optimistic accuracy of ~95% (see Example 5.5, FIG. 14, and Table 7), but not from those generated by Iz. Thus, the RT sequencing with both Py and Iz should collect more comprehensive information on genomic sequences, for example damages of DNA bases, which is lost in NGS due to the use of polymerases that can incorporate dAMP into the opposite of an abasic site ("A rule"[38]) or cause a frameshift.[39]

REFERENCES

The following references are hereby incorporated by reference in their entireties:

1. Goodwin S, McPherson J D, McCombie W R. Coming of age: ten years of next-generation sequencing technologies. *Nat Rev Genet* 17, 333-351 (2016).
2. Liu L, et al. Comparison of next-generation sequencing systems. *J Biomed Biotechnol* 2012, 251364 (2012).
3. Qi Y, et al. Reproducibility of Variant Calls in Replicate Next Generation Sequencing Experiments. *PLoS One* 10, e0119230 (2015).
4. Huang H, Keohavong P. Fidelity and predominant mutations produced by deep vent wild-type and exonuclease-deficient DNA polymerases during in vitro DNA amplification. *DNA Cell Biol* 15, 589-594 (1996).
5. Paez J G, et al. Genome coverage and sequence fidelity of phi29 polymerase-based multiple strand displacement whole genome amplification. *Nucleic Acids Res* 32, e71 (2004).
6. Martincorena Ii, Campbell P J. Somatic mutation in cancer and normal cells. *Science* 349, 1483-1489 (2015).
7. Treangen T J, Salzberg S L. Repetitive DNA and next-generation sequencing: computational challenges and solutions. *Nat Rev Genet* 13, 36-46 (2012).
8. Mukhopadhyay R. DNA sequencers: the next generation. *Anal Chem* 81, 1736-1740 (2009).
9. layer T, et al. Assessing the performance of the Oxford Nanopore Technologies MinION. *Biomolecular Detection and Quantification* 3, 1-8 (2015).
10. Szalay T, Golovchenko J A. De novo sequencing and variant calling with nanopores using PoreSeq. *Nat Biotechnol* 33, 1087-1091 (2015).
11. Jain M, Fiddes I T, Miga K H, Olsen H E, Paten B, Akeson M. Improved data analysis for the MinION nanopore sequencer. *Nat Methods* 12, 351-356 (2015).
12. Laszlo A H, et al. Decoding long nanopore sequencing reads of natural DNA. *Nat Biotechnol* 32, 829-833 (2014).
13. Manrao E A, et al. Reading DNA at single-nucleotide resolution with a mutant MspA nanopore and phi29 DNA polymerase. *Nat Biotechnol* 30, 349-353 (2012).
14. Lindsay S. The promises and challenges of solid-state sequencing. *Nat Nanotechnol* 11, 109-111 (2016).
15. Zwolak M, Ventra M D. Electronic Signature of DNA Nucleotides via Transverse Transport. *Nano Lett* 5, 421-424 (2005).
16. Tsutsui M, Taniguchi M, Yokota K, Kawai T. Identifying single nucleotides by tunnelling current. *Nat Nanotechnol* 5, 286-290 (2010).
17. Ohshiro T, Matsubara K, Tsutsui M, Furuhashi M, Taniguchi M, Kawai T. Single-molecule electrical random resequencing of DNA and RNA. *Sci Rep* 2, 501 (2012).
18. Erdmann M, David R, Fornof A R, Gaub H E. Electrically induced bonding of DNA to gold. *Nat Chem* 2, 745-749 (2010).
19. Bano F, Sluysmans D, Wislez A, Duwez A S. Unraveling the complexity of the interactions of DNA nucleotides with gold by single molecule force spectroscopy. *Nanoscale* 7, 19528-19533 (2015).
20. Kimura-Suda H, Petrovykh D Y, Tarlov M J, Whitman U. Base-Dependent Competitive Adsorption of Single-Stranded DNA on Gold. *J Am Chem Soc* 125, 9014-9015 (2003).
21. Liang F, Li S, Lindsay S, Zhang P. Synthesis, Physicochemical Properties, and Hydrogen Bonding of 4(5)-Substituted-1H-imidazole-2-carboxamide, A Potential Universal Reader for DNA Sequencing by Recognition Tunneling. *Chemistry—a European Journal* 18, 5998-6007 (2012).
22. Chang S, et al. Chemical recognition and binding kinetics in a functionalized tunnel junction. *Nanotechnology* 23, 235101 (2012).
23. Zhao Y, et al. Single-molecule spectroscopy of amino acids and peptides by recognition tunnelling. *Nature Nanotechnology* 9, 466-473 (2014).
24. Im J, et al. Electronic Single Molecule Identification of Carbohydrate Isomers by Recognition Tunneling. *arXiv*, 1601.04221 (2016).
25. Petersheimf M, Turner D H. Base-Stacking and Base-Pairing Contributions to Helix Stability: Thermodynamics of Double-Helix Formation with CCGG, CCGGp, CCGGAp, ACCGGp, CCGGUp, and ACCGGUp. *Biochemistry* 22, 256-263 (1983).
26. Yakovchuk P, Protozanova E, Frank-Kamenetskii M D. Base-stacking and base-pairing contributions into thermal stability of the DNA double helix. *Nucleic Acids Res* 34, 564-574 (2006).
27. Riley K E, Hobza P H. On the Importance and Origin of Aromatic Interactions in Chemistry and Biodisciplines. *ACCOUNTS OF CHEMICAL RESEARCH* 46, 927-936 (2013).
28. Kelley S O, Barton J K. Electron Transfer Between Bases in Double Helical DNA. *Science* 283, 375-381 (1999).
29. Xu B, Zhang P, Li X, Tao N. Direct Conductance Measurement of Single DNA Molecules in Aqueous Solution. *Nano letters* 4, 1105-1108 (2004).
30. Guckian K M, Schweitzer B A, Ren R X-F, Sheils C J, Tahmassebi D C, Kool E T. Factors Contributing to Aromatic Stacking in Water: Evaluation in the Context of DNA. *J Am Chem Soc* 122, 2213-2222 (2000).
31. Swart M, van der Wijst T, Fonseca Guerra C, Bickelhaupt F M. Pi-pi stacking tackled with density functional theory. *J Mol Model* 13, 1245-1257 (2007).

32. Lai J S, Qu J, Kool E T. Fluorinated DNA bases as probes of electrostatic effects in DNA base stacking. *Angew Chem Int Ed Engl* 42, 5973-5977 (2003).
33. Liang F, Li S, Lindsay S, Zhang P. Synthesis, physicochemical properties, and hydrogen bonding of 4(5)-substituted 1-H-imidazole-2-carboxamide, a potential universal reader for DNA sequencing by recognition tunneling. *Chemistry (Easton)* 18, 5998-6007 (2012).
34. Chang S, et al. Palladium electrodes for molecular tunnel junctions. *Nanotechnology* 23, 425202 (2012).
35. Chang S, He J, Zhang P, Gyarfas B, Lindsay S. Gap distance and interactions in a molecular tunnel junction. *J Am Chem Soc* 133, 14267-14269 (2011).
36. Grimme S. Do special noncovalent pi-pi stacking interactions really exist? *Angew Chem Int Ed Engl* 47, 3430-3434 (2008).
37. Robasky K, Lewis N E, Church G M. The role of replicates for error mitigation in next-generation sequencing. *Nat Rev Genet* 15, 56-62 (2014).
38. Strauss B S. The "A" rule revisited: polymerases as determinants of mutational specificity. *DNA Repair* 1, 125-135 (2002).
39. Patra A, Zhang Q, Lei L, Su Y, Egli M, Guengerich F P. Structural and kinetic analysis of nucleoside triphosphate incorporation opposite an abasic site by human translesion DNA polymerase eta. *J Biol Chem* 290, 8028-8038 (2015).

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present invention is not limited to the specific embodiments illustrated herein, but is limited only by the following claims.

What is claimed is:

1. An apparatus for analyzing a nucleic acid sequence in a sample, the apparatus comprising a chamber, wherein the chamber comprises:
    (a) a first and a second electrode that form a tunnel gap through which the nucleic acid sequence can pass;
    (b) a first reagent attached to the first electrode and a second reagent attached to the second electrode, wherein the first and the second reagent are capable of selectively interacting with a nucleobase of the nucleic acid sequence via π-π interactions,
    wherein a detectable signal is produced when the nucleobase interacts with the first and second reagent via the π-π interactions and the first and second reagent are each an aromatic compound selected from pyrene, benzene, anthracene, benzo[e]pyrene, 2-(phenylethynyl)pyrene, 2-phenyl pyrene, 3-nitro-1H-pyrrole and 5-nitro-1H-indole, wherein the aromatic compound is unsubstituted or substituted with a substituent selected from nitro, phenyl, $(C_1-C_6)$alkyl substituted with phenyl, $(C_2-C_6)$alkenyl substituted with phenyl or $(C_2-C_6)$alkynyl substituted with phenyl or wherein the aromatic compound is a pyrene substituted with $(C_1-C_6)$mercaptoalkyl.

2. The apparatus according to claim 1, wherein the first and/or second electrode comprise a metal selected from the group consisting of palladium, gold, graphene, carbon nanotube, and molybdenum disulphide.

3. The apparatus according to claim 1, wherein the first and second reagent are the same.

4. The apparatus according to claim 1, wherein the aromatic compound is a pyrene.

5. The apparatus according to claim 1, wherein the aromatic compound is 1-(2-mercaptoethyl)pyrene.

6. The apparatus according to claim 1, wherein the tunnel gap has a width of about 1.0 nm to about 5.0 nm.

7. The apparatus according to claim 1, further comprising a detector for measuring the detectable signal.

8. The apparatus according to claim 1, further comprising a system for introducing and removing buffer and the sample into the chamber.

9. The apparatus according to claim 1, further comprising a system for analyzing the detectable signal.

10. The apparatus according to claim 1, wherein the sample is a biological sample.

11. The apparatus according to claim 1, wherein the nucleic acid is DNA, RNA, PNA, XNA or unnatural bases.

12. A method of determining the sequence of a nucleic acid, the method comprising
    (a) providing an apparatus according to claim 1;
    (b) passing a nucleic acid through the tunnel gap;
    (c) detecting the signal produced when a nucleobase of the nucleic acid interacts with the first and second reagent, wherein detecting comprises detecting an electrical current;
    (d) from the signal detected in (c), identifying the nucleobase of the nucleic acid; and
    (e) repeating steps (b) through (d);
    (f) from the nucleobases identified in (d), determining the sequence of the nucleic acid.

13. The apparatus of claim 1, wherein the first reagent and/or the second reagent further comprise a functional group selected from thiol, disulfide, or amine for selective attachment to the first electrode and/or the second electrode, respectively.

* * * * *